United States Patent
Luu

(10) Patent No.: US 11,344,424 B2
(45) Date of Patent: May 31, 2022

(54) EXPANDABLE INTERVERTEBRAL IMPLANT AND RELATED METHODS

(71) Applicant: Medos International Sarl, LeLocle (CH)

(72) Inventor: Phat Luu, New Bedford, MA (US)

(73) Assignee: Medos International Sarl

( * ) Notice: Subject to any disclaimer, the term of this patent is extended or adjusted under 35 U.S.C. 154(b) by 39 days.

(21) Appl. No.: 15/995,550

(22) Filed: Jun. 1, 2018

(65) Prior Publication Data

US 2018/0360616 A1 Dec. 20, 2018

Related U.S. Application Data

(60) Provisional application No. 62/519,470, filed on Jun. 14, 2017.

(51) Int. Cl.
 *A61F 2/44* (2006.01)
 *A61F 2/30* (2006.01)

(52) U.S. Cl.
 CPC ............ *A61F 2/4425* (2013.01); *A61F 2/447* (2013.01); *A61F 2/4455* (2013.01);
 (Continued)

(58) Field of Classification Search
 CPC ...................................... A61F 2/44–2002/4495
 See application file for complete search history.

(56) References Cited

U.S. PATENT DOCUMENTS

| 1,802,560 | A | 4/1931 | Kerwin |
| 1,924,695 | A | 8/1933 | Olson |

(Continued)

FOREIGN PATENT DOCUMENTS

| AU | 2006279558 A1 | 2/2007 |
| AU | 2005314079 B2 | 7/2012 |

(Continued)

OTHER PUBLICATIONS

Zucherman, "A Multicenter, Prospective, Randomized Trial Evaluating the X STOP Interspinous Process Decompression System for the Treatment of Neurogenic Intermittent Claudication", Spine, vol. 30, No. 12, pp. 1351-1358, 2005.

(Continued)

*Primary Examiner* — Zade Coley
(74) *Attorney, Agent, or Firm* — BakerHostetler

(57) ABSTRACT

An expandable implant includes a first plate and a second plate spaced from each other along a first direction. The first plate defines a first bone-contacting surface configured to contact a superior vertebral body and the second plate defines a second bone-contacting surface opposed to the first bone contacting surface along the first direction. The second bone contacting surface is configured to contact an inferior vertebral body. The implant includes an actuation member at least partially disposed between the first and second plates with respect to the first direction. The actuation member defines a first axis, a first end and a second end spaced from the first end along a second direction along the first axis. The second direction is perpendicular to the first direction. The implant includes first and second wedge members carried by the actuation member and in engagement with the first and second plates, and also includes a drive member defining a second axis, a proximal end and a distal end spaced from the proximal end along a third direction along the second axis. The third direction is perpendicular to the first direction and offset from the second direction. The drive member is configured to communicate a driving force to the actuation member so as to cause the actuation member to rotate about the first axis, and at least one of the first and second wedge members is configured to translate along the second direction in response to rotation of the actuation member about (Continued)

the first axis so as to move at least one of the first and second plates with respect to the other of the first and second plates along the first direction.

12 Claims, 11 Drawing Sheets

(52) U.S. Cl.
CPC .............. *A61F 2002/30387* (2013.01); *A61F 2002/30405* (2013.01); *A61F 2002/30411* (2013.01); *A61F 2002/30433* (2013.01); *A61F 2002/30507* (2013.01); *A61F 2002/30523* (2013.01); *A61F 2002/30537* (2013.01); *A61F 2002/30538* (2013.01); *A61F 2002/30556* (2013.01); *A61F 2002/443* (2013.01)

(56) References Cited

U.S. PATENT DOCUMENTS

| | | |
|---|---|---|
| 1,965,653 A | 7/1934 | Kennedy |
| 2,077,804 A | 4/1937 | Morrison |
| 2,115,250 A | 4/1938 | Bruson |
| 2,121,193 A | 6/1938 | Hanicke |
| 2,170,111 A | 8/1939 | Bruson |
| 2,173,655 A | 9/1939 | Neracher et al. |
| 2,229,024 A | 1/1941 | Bruson |
| 2,243,717 A | 5/1941 | Moreira |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,570,465 A | 10/1951 | Lundholm |
| 2,677,369 A | 5/1954 | Knowles |
| 2,706,701 A | 4/1955 | Hans et al. |
| 2,710,277 A | 6/1955 | Shelanski et al. |
| 2,826,532 A | 3/1958 | Hosmer |
| 2,900,305 A | 8/1959 | Siggia |
| 2,977,315 A | 3/1961 | Scheib et al. |
| 3,091,237 A | 5/1963 | Skinner |
| 3,112,743 A | 12/1963 | Cochran et al. |
| 3,115,804 A | 12/1963 | Johnson |
| 3,228,828 A | 1/1966 | Romano |
| 3,312,139 A | 4/1967 | Di Cristina |
| 3,486,505 A | 12/1969 | Morrison |
| 3,489,143 A | 1/1970 | Halloran |
| 3,648,294 A | 3/1972 | Shahrestani |
| 3,698,391 A | 10/1972 | Mahony |
| 3,717,655 A | 2/1973 | Godefroi et al. |
| 3,760,802 A | 9/1973 | Fischer et al. |
| 3,800,788 A | 4/1974 | White |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,855,638 A | 12/1974 | Pilliar |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,175,555 A | 11/1979 | Herbert |
| 4,236,512 A | 12/1980 | Aginsky |
| 4,249,435 A | 2/1981 | Smith et al. |
| 4,262,665 A | 4/1981 | Roalstad et al. |
| 4,262,676 A | 4/1981 | Jamshidi |
| 4,274,163 A | 6/1981 | Malcom et al. |
| 4,275,717 A | 6/1981 | Bolesky |
| 4,312,337 A | 1/1982 | Donohue |
| 4,312,353 A | 1/1982 | Shahbabian |
| 4,313,434 A | 2/1982 | Segal |
| 4,341,206 A | 7/1982 | Perrett et al. |
| 4,349,921 A | 9/1982 | Kuntz |
| 4,350,151 A | 9/1982 | Scott |
| 4,351,069 A | 9/1982 | Ballintyn et al. |
| 4,352,883 A | 10/1982 | Lim |
| 4,369,790 A | 1/1983 | McCarthy |
| 4,399,814 A | 8/1983 | Pratt et al. |
| 4,401,112 A | 8/1983 | Rezaian |
| 4,401,433 A | 8/1983 | Luther |
| 4,409,974 A | 10/1983 | Freedland |
| 4,440,921 A | 4/1984 | Allcock et al. |
| 4,449,532 A | 5/1984 | Storz |
| 4,451,256 A | 5/1984 | Weikl et al. |
| 4,456,005 A | 6/1984 | Lichty |
| 4,462,394 A | 7/1984 | Jacobs |
| 4,463,753 A | 8/1984 | Gustilo |
| 4,466,435 A | 8/1984 | Murray |
| 4,467,479 A | 8/1984 | Brody |
| 4,488,543 A | 12/1984 | Tornier |
| 4,488,549 A | 12/1984 | Lee et al. |
| 4,494,535 A | 1/1985 | Haig |
| 4,495,174 A | 1/1985 | Allcock et al. |
| 4,532,660 A | 8/1985 | Field |
| 4,537,185 A | 8/1985 | Stednitz |
| 4,538,612 A | 9/1985 | Patrick, Jr. |
| 4,542,539 A | 9/1985 | Rowe et al. |
| 4,545,374 A | 10/1985 | Jacobson |
| 4,562,598 A | 1/1986 | Kranz |
| 4,573,448 A | 3/1986 | Kambin |
| 4,595,006 A | 6/1986 | Burke et al. |
| 4,601,710 A | 7/1986 | Moll |
| 4,625,722 A | 12/1986 | Murray |
| 4,625,725 A | 12/1986 | Davison et al. |
| 4,627,434 A | 12/1986 | Murray |
| 4,628,945 A | 12/1986 | Johnson, Jr. |
| 4,629,450 A | 12/1986 | Suzuki et al. |
| 4,630,616 A | 12/1986 | Tretinyak |
| 4,632,101 A | 12/1986 | Freedland |
| 4,640,271 A | 2/1987 | Lower |
| 4,641,640 A | 2/1987 | Griggs |
| 4,645,503 A | 2/1987 | Lin et al. |
| 4,646,741 A | 3/1987 | Smith |
| 4,651,717 A | 3/1987 | Jakubczak |
| 4,653,489 A | 3/1987 | Tronzo |
| 4,665,906 A | 5/1987 | Jervis |
| 4,667,663 A | 5/1987 | Miyata |
| 4,686,973 A | 8/1987 | Frisch |
| 4,686,984 A | 8/1987 | Bonnet |
| 4,688,561 A | 8/1987 | Reese |
| 4,697,584 A | 10/1987 | Haynes |
| 4,706,670 A | 11/1987 | Andersen et al. |
| 4,714,469 A | 12/1987 | Kenna |
| 4,714,478 A | 12/1987 | Fischer |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,772,287 A | 9/1988 | Ray et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,834,069 A | 5/1989 | Umeda |
| 4,834,757 A | 5/1989 | Brantigan |
| 4,838,282 A | 6/1989 | Strasser et al. |
| 4,856,950 A | 8/1989 | Bushnell |
| 4,858,601 A | 8/1989 | Glisson |
| 4,862,891 A | 9/1989 | Smith |
| 4,863,476 A | 9/1989 | Shepperd |
| 4,870,153 A | 9/1989 | Matzner et al. |
| 4,871,366 A | 10/1989 | Von et al. |
| 4,873,976 A | 10/1989 | Schreiber |
| 4,878,915 A | 11/1989 | Brantigan |
| 4,880,622 A | 11/1989 | Allcock et al. |
| 4,888,022 A | 12/1989 | Huebsch |

(56) References Cited

U.S. PATENT DOCUMENTS

| | | |
|---|---|---|
| 4,888,024 A | 12/1989 | Powlan |
| 4,889,119 A | 12/1989 | Jamiolkowski et al. |
| 4,892,550 A | 1/1990 | Huebsch |
| 4,896,662 A | 1/1990 | Noble |
| 4,898,186 A | 2/1990 | Ikada et al. |
| 4,898,577 A | 2/1990 | Badger et al. |
| 4,903,692 A | 2/1990 | Reese |
| 4,904,261 A | 2/1990 | Dove et al. |
| 4,911,718 A | 3/1990 | Lee et al. |
| 4,917,554 A | 4/1990 | Bronn |
| 4,932,969 A | 6/1990 | Frey et al. |
| 4,940,467 A | 7/1990 | Tronzo |
| 4,941,466 A | 7/1990 | Romano |
| 4,946,378 A | 8/1990 | Hirayama et al. |
| 4,959,064 A | 9/1990 | Engelhardt |
| 4,961,740 A | 10/1990 | Ray et al. |
| 4,963,144 A | 10/1990 | Huene |
| 4,966,587 A | 10/1990 | Baumgart |
| 4,968,317 A | 11/1990 | Toermaelae et al. |
| 4,969,888 A | 11/1990 | Scholten et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 4,995,200 A | 2/1991 | Eberhart |
| 5,002,557 A | 3/1991 | Hasson |
| 5,006,121 A | 4/1991 | Hafeli |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,019,082 A | 5/1991 | Frey et al. |
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,719 A | 7/1992 | Winston |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Lazarus |
| 5,163,939 A | 11/1992 | Winston |
| 5,163,989 A | 11/1992 | Campbell et al. |
| 5,167,663 A | 12/1992 | Brumfield |
| 5,167,664 A | 12/1992 | Hodorek |
| 5,169,400 A | 12/1992 | Muehling et al. |
| 5,169,402 A | 12/1992 | Elloy |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,475 A | 6/1993 | Kuber |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,250,061 A | 10/1993 | Michelson |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,320,644 A | 6/1994 | Baumgartner |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |

(56) References Cited

U.S. PATENT DOCUMENTS

| | | |
|---|---|---|
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,815 A | 10/1995 | Geisser et al. |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka et al. |
| 5,462,563 A | 10/1995 | Shearer et al. |
| 5,464,427 A | 11/1995 | Curtis et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,601,556 A | 2/1997 | Pisharodi |
| 5,601,561 A | 2/1997 | Ferry et al. |
| 5,601,572 A | 2/1997 | Middleman et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,700,239 A | 12/1997 | Yoon |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,531 A | 3/1998 | Shapiro |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,788,703 A | 8/1998 | Mittelmeier et al. |
| 5,792,044 A | 8/1998 | Foley et al. |
| 5,800,549 A | 9/1998 | Bao et al. |
| 5,807,275 A | 9/1998 | Jamshidi |
| 5,807,327 A | 9/1998 | Green et al. |

(56) References Cited

U.S. PATENT DOCUMENTS

| | | |
|---|---|---|
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,857,995 A | 1/1999 | Thomas et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,916,228 A | 6/1999 | Ripich et al. |
| 5,916,267 A | 6/1999 | Prakit |
| 5,919,235 A | 7/1999 | Husson et al. |
| 5,925,056 A | 7/1999 | Thomas et al. |
| 5,925,074 A | 7/1999 | Gingras et al. |
| 5,928,235 A | 7/1999 | Friedl |
| 5,928,244 A | 7/1999 | Tovey et al. |
| 5,928,422 A | 7/1999 | Uchiyama et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao et al. |
| 5,976,187 A | 11/1999 | Richelsoph |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,508 A | 1/2000 | Bradley |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Schoenhoeffer |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,053,922 A | 4/2000 | Krause et al. |
| 6,053,935 A | 4/2000 | Brenneman et al. |
| 6,056,763 A | 5/2000 | Parsons |
| 6,063,121 A | 5/2000 | Xavier et al. |
| 6,066,142 A | 5/2000 | Serbousek et al. |
| 6,066,154 A | 5/2000 | Reiley et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,158 A | 6/2000 | Lin |
| 6,080,193 A | 6/2000 | Hochschuler et al. |
| 6,083,225 A | 7/2000 | Winslow et al. |
| 6,083,244 A | 7/2000 | Lubbers et al. |
| 6,090,112 A | 7/2000 | Zucherman et al. |
| 6,090,143 A | 7/2000 | Meriwether et al. |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,508 A | 9/2000 | Gruenig et al. |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,558 A | 10/2000 | Wagner |

(56) References Cited

U.S. PATENT DOCUMENTS

| | | |
|---|---|---|
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Espinosa |
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,235,043 B1 | 5/2001 | Reiley et al. |
| 6,238,397 B1 | 5/2001 | Zucherman et al. |
| 6,238,491 B1 | 5/2001 | Davidson et al. |
| 6,241,733 B1 | 6/2001 | Nicholson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Toermaelae et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,258,093 B1 | 7/2001 | Edwards et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,644 B1 | 10/2001 | Saurat et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| D450,676 S | 11/2001 | Huttner |
| 6,312,443 B1 | 11/2001 | Stone |
| 6,319,252 B1 | 11/2001 | McDevitt et al. |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,374,971 B1 | 4/2002 | Siciliano et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,398,793 B1 | 6/2002 | McGuire |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,436,101 B1 | 8/2002 | Hamada |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,518 B1 | 9/2002 | Krause et al. |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |

(56) References Cited

U.S. PATENT DOCUMENTS

| | | |
|---|---|---|
| 6,454,806 B1 | 9/2002 | Cohen et al. |
| 6,454,807 B1 | 9/2002 | Jackson |
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul et al. |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Lambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,320 B1 | 6/2003 | Gauchet et al. |
| 6,579,321 B1 | 6/2003 | Gordon et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,066 B2 | 8/2003 | Dinger et al. |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,629,998 B1 | 10/2003 | Lin |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,060 B2 | 10/2003 | Hanson et al. |
| 6,635,362 B2 | 10/2003 | Zheng |
| RE38,335 E | 11/2003 | Aust et al. |
| D482,787 S | 11/2003 | Reiss |
| 6,641,564 B1 | 11/2003 | Kraus |
| 6,641,582 B1 | 11/2003 | Hanson et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,004 B2 | 12/2003 | Barker et al. |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,679,915 B1 | 1/2004 | Cauthen |
| 6,682,535 B2 | 1/2004 | Hoogland |
| 6,682,561 B2 | 1/2004 | Songer et al. |
| 6,682,562 B2 | 1/2004 | Viart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |

(56) References Cited

U.S. PATENT DOCUMENTS

| | | |
|---|---|---|
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,837 B2 | 6/2004 | Ebner |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,847 B2 | 7/2004 | Maguire |
| 6,758,861 B2 | 7/2004 | Ralph et al. |
| 6,758,862 B2 | 7/2004 | Berry et al. |
| 6,761,720 B1 | 7/2004 | Senegas |
| 6,764,491 B2 | 7/2004 | Frey et al. |
| 6,764,514 B1 | 7/2004 | Li et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B1 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,941 B2 | 1/2005 | Rogers et al. |
| 6,840,944 B2 | 1/2005 | Suddaby |
| 6,852,126 B2 | 2/2005 | Ahlgren |
| 6,852,127 B2 | 2/2005 | Varga et al. |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,878,167 B2 | 4/2005 | Ferree |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | Von et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,949,108 B2 | 9/2005 | Holmes |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,966,912 B2 | 11/2005 | Michelson |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |
| 7,060,073 B2 | 6/2006 | Frey et al. |

(56) References Cited

U.S. PATENT DOCUMENTS

| | | |
|---|---|---|
| 7,063,701 B2 | 6/2006 | Michelson |
| 7,063,702 B2 | 6/2006 | Michelson |
| 7,063,703 B2 | 6/2006 | Reo |
| 7,063,725 B2 | 6/2006 | Foley |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,053 B2 | 8/2006 | Vanney |
| 7,087,055 B2 | 8/2006 | Lim et al. |
| 7,087,083 B2 | 8/2006 | Pasquet et al. |
| 7,089,063 B2 | 8/2006 | Lesh et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,125,424 B2 | 10/2006 | Banick et al. |
| 7,128,760 B2 * | 10/2006 | Michelson .............. A61F 2/446 623/17.15 |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,156,877 B2 | 1/2007 | Lotz et al. |
| 7,163,558 B2 | 1/2007 | Senegas et al. |
| 7,166,107 B2 | 1/2007 | Anderson |
| 7,172,612 B2 | 2/2007 | Ishikawa |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,282,061 B2 | 10/2007 | Sharkey et al. |
| 7,291,173 B2 | 11/2007 | Richelsoph et al. |
| 7,306,628 B2 | 12/2007 | Zucherman et al. |
| 7,309,357 B2 | 12/2007 | Kim |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,351,262 B2 | 4/2008 | Bindseil et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,406,775 B2 | 8/2008 | Funk et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,637 B2 | 11/2008 | Taylor |
| 7,470,273 B2 | 12/2008 | Dougherty-Shah |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,074 B2 | 8/2009 | Eisermann et al. |
| 7,572,279 B2 | 8/2009 | Jackson |
| 7,575,580 B2 | 8/2009 | Lim et al. |
| 7,575,599 B2 | 8/2009 | Villiers et al. |
| 7,578,820 B2 | 8/2009 | Moore et al. |
| 7,588,574 B2 | 9/2009 | Assell et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,377 B2 | 12/2009 | Veldhuizen et al. |
| 7,625,378 B2 | 12/2009 | Foley |
| 7,625,394 B2 | 12/2009 | Molz et al. |
| 7,637,905 B2 | 12/2009 | Saadat et al. |
| 7,641,657 B2 | 1/2010 | Cragg |
| 7,641,670 B2 | 1/2010 | Davison et al. |
| 7,641,692 B2 | 1/2010 | Bryan et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,186 B2 | 2/2010 | Harp |
| 7,666,266 B2 | 2/2010 | Izawa et al. |
| 7,670,354 B2 | 3/2010 | Davison et al. |
| 7,670,374 B2 | 3/2010 | Schaller |
| 7,674,265 B2 | 3/2010 | Smith et al. |
| 7,674,273 B2 | 3/2010 | Davison et al. |
| 7,682,370 B2 | 3/2010 | Pagliuca et al. |
| 7,682,400 B2 | 3/2010 | Zwirkoski |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,704,280 B2 | 4/2010 | Lechmann et al. |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,731,751 B2 | 6/2010 | Butler et al. |
| 7,740,633 B2 | 6/2010 | Assell et al. |
| 7,744,599 B2 | 6/2010 | Cragg |

(56) References Cited

U.S. PATENT DOCUMENTS

| | | | |
|---|---|---|---|
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth |
| 7,763,028 B2 | 7/2010 | Lim et al. |
| 7,763,038 B2 | 7/2010 | O'Brien |
| 7,763,055 B2 | 7/2010 | Foley |
| 7,766,930 B2 | 8/2010 | DiPoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2* | 9/2010 | Michelson | A61F 2/442 623/17.16 |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | McKinley |
| 7,799,083 B2 | 9/2010 | Smith et al. |
| 7,803,161 B2 | 9/2010 | Foley et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | LeHuec et al. |
| 7,837,734 B2* | 11/2010 | Zucherman | A61F 2/4425 623/17.15 |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,909,874 B2 | 3/2011 | Zielinski |
| 7,918,874 B2 | 4/2011 | Siegal |
| 7,922,719 B2 | 4/2011 | Ralph et al. |
| 7,922,729 B2 | 4/2011 | Michelson |
| 7,931,674 B2 | 4/2011 | Zucherman et al. |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,967 B1 | 6/2011 | Woods |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 7,998,176 B2 | 8/2011 | Culbert |
| 8,007,535 B2 | 8/2011 | Hudgins et al. |
| 8,012,212 B2 | 9/2011 | Link et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,034,110 B2 | 10/2011 | Garner et al. |
| 8,038,703 B2 | 10/2011 | Dobak et al. |
| 8,043,293 B2 | 10/2011 | Warnick |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2* | 1/2012 | Olmos | A61F 2/4611 623/17.15 |
| 8,109,972 B2 | 2/2012 | Zucherman et al. |
| 8,109,977 B2 | 2/2012 | Culbert et al. |
| 8,118,871 B2 | 2/2012 | Gordon |
| 8,128,700 B2 | 3/2012 | Delurio et al. |
| 8,128,702 B2 | 3/2012 | Zucherman et al. |
| 8,133,232 B2 | 3/2012 | Levy et al. |
| 8,147,549 B2 | 4/2012 | Metcalf et al. |
| 8,177,812 B2 | 5/2012 | Sankaran |
| 8,187,327 B2 | 5/2012 | Edidin et al. |
| 8,187,332 B2* | 5/2012 | McLuen | A61F 2/4455 623/17.16 |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,216,317 B2 | 7/2012 | Thibodeau |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,675 B2 | 7/2012 | Rhoda |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,241,364 B2 | 8/2012 | Hansell et al. |
| 8,246,622 B2 | 8/2012 | Siegal et al. |
| 8,257,440 B2 | 9/2012 | Gordon et al. |
| 8,257,442 B2* | 9/2012 | Edie | A61F 2/44 623/17.11 |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |
| 8,343,222 B2 | 1/2013 | Cope |
| 8,353,961 B2 | 1/2013 | McClintock et al. |
| 8,361,154 B2 | 1/2013 | Reo |
| 8,366,777 B2 | 2/2013 | Matthis et al. |
| 8,377,098 B2 | 2/2013 | Landry et al. |
| 8,377,133 B2 | 2/2013 | Yuan et al. |
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2* | 3/2013 | Weiman | A61F 2/44 623/17.16 |
| 8,403,990 B2 | 3/2013 | Dryer et al. |
| 8,409,282 B2 | 4/2013 | Kim |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,425,559 B2 | 4/2013 | Tebbe et al. |
| 8,435,298 B2 | 5/2013 | Weiman |
| 8,454,617 B2 | 6/2013 | Schaller et al. |
| 8,454,698 B2 | 6/2013 | De et al. |

(56) References Cited

U.S. PATENT DOCUMENTS

| | | | |
|---|---|---|---|
| 8,465,524 B2 | 6/2013 | Siegal | |
| 8,470,043 B2 | 6/2013 | Schaller et al. | |
| 8,480,715 B2 | 7/2013 | Gray | |
| 8,480,742 B2 | 7/2013 | Pisharodi | |
| 8,480,748 B2 | 7/2013 | Poulos | |
| 8,486,109 B2 | 7/2013 | Siegal | |
| 8,486,148 B2 | 7/2013 | Butler et al. | |
| 8,491,591 B2 | 7/2013 | Fuerderer | |
| 8,491,653 B2 | 7/2013 | Zucherman et al. | |
| 8,491,657 B2 | 7/2013 | Attia et al. | |
| 8,491,659 B2 | 7/2013 | Weiman | |
| 8,506,635 B2 | 8/2013 | Palmatier et al. | |
| 8,518,087 B2 * | 8/2013 | Lopez | A61F 2/447 606/279 |
| 8,518,120 B2 | 8/2013 | Glerum et al. | |
| 8,523,909 B2 | 9/2013 | Hess | |
| 8,523,944 B2 | 9/2013 | Jimenez et al. | |
| 8,535,380 B2 | 9/2013 | Greenhalgh et al. | |
| 8,545,567 B1 | 10/2013 | Krueger | |
| 8,551,092 B2 | 10/2013 | Morgan et al. | |
| 8,551,173 B2 | 10/2013 | Lechmann et al. | |
| 8,556,978 B2 | 10/2013 | Schaller | |
| 8,556,979 B2 | 10/2013 | Glerum et al. | |
| 8,568,481 B2 * | 10/2013 | Olmos | A61F 2/4657 623/17.15 |
| 8,579,977 B2 | 11/2013 | Fabian | |
| 8,579,981 B2 | 11/2013 | Lim et al. | |
| 8,591,583 B2 | 11/2013 | Schaller et al. | |
| 8,591,585 B2 | 11/2013 | McLaughlin et al. | |
| 8,597,330 B2 | 12/2013 | Siegal | |
| 8,597,333 B2 | 12/2013 | Morgenstern et al. | |
| 8,597,360 B2 * | 12/2013 | McLuen | A61F 2/4455 623/17.16 |
| 8,603,168 B2 | 12/2013 | Gordon et al. | |
| 8,603,170 B2 | 12/2013 | Cipoletti et al. | |
| 8,603,177 B2 | 12/2013 | Gray | |
| 8,610,091 B2 | 12/2013 | Matsumoto | |
| 8,623,091 B2 | 1/2014 | Suedkamp et al. | |
| 8,628,576 B2 | 1/2014 | Triplett et al. | |
| 8,628,577 B1 | 1/2014 | Jimenez | |
| 8,628,578 B2 | 1/2014 | Miller et al. | |
| 8,632,595 B2 | 1/2014 | Weiman | |
| 8,636,746 B2 | 1/2014 | Jimenez et al. | |
| 8,641,764 B2 | 2/2014 | Gately | |
| 8,663,329 B2 * | 3/2014 | Ernst | A61F 2/4465 623/17.15 |
| 8,663,331 B2 | 3/2014 | McClellan et al. | |
| 8,668,740 B2 | 3/2014 | Rhoda et al. | |
| 8,672,977 B2 | 3/2014 | Siegal et al. | |
| 8,679,161 B2 | 3/2014 | Malandain et al. | |
| 8,679,183 B2 | 3/2014 | Glerum et al. | |
| 8,685,095 B2 | 4/2014 | Miller et al. | |
| 8,685,098 B2 | 4/2014 | Glerum et al. | |
| 8,696,751 B2 | 4/2014 | Ashley et al. | |
| 8,702,757 B2 | 4/2014 | Thommen et al. | |
| 8,702,798 B2 | 4/2014 | Matthis et al. | |
| 8,709,086 B2 | 4/2014 | Glerum | |
| 8,709,088 B2 | 4/2014 | Kleiner et al. | |
| 8,715,351 B1 | 5/2014 | Pinto | |
| 8,721,723 B2 | 5/2014 | Hansell et al. | |
| 8,728,160 B2 | 5/2014 | Globerman et al. | |
| 8,728,166 B2 | 5/2014 | Schwab | |
| 8,740,954 B2 | 6/2014 | Ghobrial et al. | |
| 8,753,398 B2 | 6/2014 | Gordon et al. | |
| 8,758,349 B2 | 6/2014 | Germain et al. | |
| 8,758,441 B2 | 6/2014 | Hovda et al. | |
| 8,764,806 B2 | 7/2014 | Abdou | |
| 8,771,360 B2 | 7/2014 | Jimenez et al. | |
| 8,777,993 B2 | 7/2014 | Siegal et al. | |
| 8,778,025 B2 | 7/2014 | Ragab et al. | |
| 8,795,366 B2 | 8/2014 | Varela | |
| 8,795,374 B2 | 8/2014 | Chee | |
| 8,801,787 B2 | 8/2014 | Schaller | |
| 8,801,792 B2 | 8/2014 | De et al. | |
| 8,808,376 B2 | 8/2014 | Schaller | |
| 8,828,085 B1 | 9/2014 | Jensen | |
| 8,845,638 B2 | 9/2014 | Siegal et al. | |
| 8,845,728 B1 | 9/2014 | Abdou | |
| 8,845,731 B2 | 9/2014 | Weiman | |
| 8,845,732 B2 | 9/2014 | Weiman | |
| 8,845,733 B2 | 9/2014 | O'Neil et al. | |
| 8,845,734 B2 | 9/2014 | Weiman | |
| 8,852,242 B2 | 10/2014 | Morgenstern et al. | |
| 8,852,243 B2 | 10/2014 | Morgenstern et al. | |
| 8,852,279 B2 | 10/2014 | Weiman | |
| 8,864,833 B2 | 10/2014 | Glerum et al. | |
| 8,888,853 B2 | 11/2014 | Glerum et al. | |
| 8,888,854 B2 | 11/2014 | Glerum et al. | |
| 8,900,235 B2 | 12/2014 | Siegal | |
| 8,900,307 B2 | 12/2014 | Hawkins et al. | |
| 8,906,098 B2 | 12/2014 | Siegal | |
| 8,920,506 B2 | 12/2014 | McGuckin, Jr. | |
| 8,926,704 B2 | 1/2015 | Glerum et al. | |
| 8,936,641 B2 | 1/2015 | Cain | |
| 8,940,049 B1 | 1/2015 | Jimenez et al. | |
| 8,940,050 B2 | 1/2015 | Laurence et al. | |
| 8,940,052 B2 | 1/2015 | Lechmann et al. | |
| 8,961,609 B2 | 2/2015 | Schaller | |
| 8,968,408 B2 | 3/2015 | Schaller et al. | |
| 8,974,508 B2 | 3/2015 | Stephan et al. | |
| 8,979,929 B2 | 3/2015 | Schaller | |
| 8,986,387 B1 | 3/2015 | To et al. | |
| 8,986,388 B2 | 3/2015 | Siegal et al. | |
| 8,986,389 B2 | 3/2015 | Lim et al. | |
| 9,005,291 B2 | 4/2015 | Loebl et al. | |
| 9,017,408 B2 | 4/2015 | Siegal et al. | |
| 9,017,413 B2 | 4/2015 | Siegal et al. | |
| 9,039,767 B2 | 5/2015 | Raymond et al. | |
| 9,039,771 B2 | 5/2015 | Glerum et al. | |
| 9,044,334 B2 | 6/2015 | Siegal et al. | |
| 9,044,338 B2 | 6/2015 | Schaller | |
| 9,060,876 B1 | 6/2015 | To et al. | |
| 9,066,808 B2 | 6/2015 | Schaller | |
| 9,078,767 B1 | 7/2015 | McLean | |
| 9,089,428 B2 | 7/2015 | Bertele et al. | |
| 9,095,446 B2 | 8/2015 | Landry et al. | |
| 9,095,447 B2 | 8/2015 | Barreiro et al. | |
| 9,101,488 B2 | 8/2015 | Malandain | |
| 9,101,489 B2 | 8/2015 | Protopsaltis et al. | |
| 9,101,491 B2 | 8/2015 | Rodgers et al. | |
| 9,101,492 B2 | 8/2015 | Mangione et al. | |
| 9,107,766 B1 | 8/2015 | McLean et al. | |
| 9,119,730 B2 | 9/2015 | Glerum | |
| 9,237,956 B1 | 1/2016 | Jensen | |
| 9,254,138 B2 | 2/2016 | Siegal et al. | |
| 9,259,326 B2 | 2/2016 | Schaller | |
| 9,271,846 B2 | 3/2016 | Lim et al. | |
| 9,277,928 B2 | 3/2016 | Morgenstern Lopez | |
| 9,282,979 B2 | 3/2016 | O'Neil et al. | |
| 9,283,092 B2 | 3/2016 | Siegal et al. | |
| 9,295,562 B2 | 3/2016 | Lechmann et al. | |
| 9,314,348 B2 | 4/2016 | Emstad | |
| 9,326,866 B2 | 5/2016 | Schaller et al. | |
| 9,333,091 B2 | 5/2016 | Dimauro | |
| 9,387,087 B2 | 7/2016 | Tyber | |
| 9,402,732 B2 | 8/2016 | Gabelberger | |
| 9,402,739 B2 | 8/2016 | Weiman et al. | |
| 9,408,712 B2 | 8/2016 | Siegal et al. | |
| 9,414,923 B2 | 8/2016 | Studer et al. | |
| 9,414,934 B2 | 8/2016 | Cain | |
| 9,414,936 B2 | 8/2016 | Miller et al. | |
| 9,433,510 B2 | 9/2016 | Lechmann et al. | |
| 9,439,776 B2 | 9/2016 | Dimauro et al. | |
| 9,439,777 B2 | 9/2016 | Dimauro | |
| 9,445,825 B2 | 9/2016 | Belaney et al. | |
| 9,445,918 B1 | 9/2016 | Lin et al. | |
| 9,445,919 B2 | 9/2016 | Palmatier et al. | |
| 9,463,099 B2 | 10/2016 | Levy et al. | |
| 9,474,623 B2 | 10/2016 | Cain | |
| 9,492,288 B2 * | 11/2016 | Wagner | A61F 2/4455 |
| 9,510,954 B2 | 12/2016 | Glerum et al. | |
| 9,532,884 B2 | 1/2017 | Siegal et al. | |
| 9,566,165 B2 | 2/2017 | Lee et al. | |
| 9,566,167 B2 | 2/2017 | Barrus et al. | |

(56) References Cited

U.S. PATENT DOCUMENTS

| | | |
|---|---|---|
| 9,579,215 B2 | 2/2017 | Suedkamp et al. |
| 9,592,129 B2 | 3/2017 | Slivka et al. |
| 9,597,197 B2 | 3/2017 | Lechmann et al. |
| 9,662,223 B2 | 5/2017 | Matthis et al. |
| 9,662,224 B2 | 5/2017 | Weiman |
| 9,675,470 B2 | 6/2017 | Packer et al. |
| 9,724,207 B2 | 8/2017 | Dimauro et al. |
| 9,730,803 B2 | 8/2017 | Dimauro et al. |
| 9,750,552 B2 | 9/2017 | Stephan et al. |
| 9,750,618 B1 | 9/2017 | Daffinson et al. |
| 9,788,962 B2 | 10/2017 | Gabelberger |
| 9,788,963 B2 | 10/2017 | Aquino et al. |
| 9,788,971 B1 | 10/2017 | Stein |
| 9,801,639 B2 | 10/2017 | O'Neil et al. |
| 9,801,640 B2 | 10/2017 | O'Neil et al. |
| 9,801,729 B2 | 10/2017 | Dimauro et al. |
| 9,801,734 B1 | 10/2017 | Stein et al. |
| 9,808,351 B2 | 11/2017 | Kelly et al. |
| 9,808,353 B2 | 11/2017 | Suddaby et al. |
| 9,814,589 B2 | 11/2017 | Dimauro |
| 9,814,590 B2 | 11/2017 | Serhan et al. |
| 9,833,334 B2 | 12/2017 | Voellmicke et al. |
| 9,839,528 B2 | 12/2017 | Weiman |
| 9,839,530 B2 | 12/2017 | Hawkins et al. |
| 9,848,991 B2 | 12/2017 | Boehm et al. |
| 9,872,779 B2 | 1/2018 | Miller et al. |
| 9,907,670 B2 | 3/2018 | Deridder et al. |
| 9,918,851 B2 | 3/2018 | Willis et al. |
| 9,924,978 B2 | 3/2018 | Thommen et al. |
| 9,925,060 B2 | 3/2018 | Dimauro et al. |
| 9,931,223 B2 | 4/2018 | Cain |
| 9,931,226 B2 | 4/2018 | Kurtaliaj et al. |
| 9,937,053 B2 | 4/2018 | Melkent et al. |
| 9,949,769 B2 | 4/2018 | Serhan et al. |
| 9,962,272 B1 | 5/2018 | Daffinson et al. |
| 9,974,664 B2 | 5/2018 | Emerick et al. |
| 9,980,823 B2 | 5/2018 | Matthis et al. |
| 9,987,142 B2 | 6/2018 | McConnell |
| 9,993,350 B2 | 6/2018 | Cain |
| 10,004,607 B2 | 6/2018 | Weiman et al. |
| 10,058,433 B2 | 8/2018 | Lechmann et al. |
| 10,085,843 B2 | 10/2018 | Dimauro |
| 10,092,417 B2 | 10/2018 | Weiman et al. |
| 10,137,009 B2 | 11/2018 | Weiman et al. |
| 10,143,569 B2 | 12/2018 | Weiman et al. |
| 10,166,117 B1 | 1/2019 | Daffinson et al. |
| 10,219,915 B1 | 3/2019 | Stein |
| 10,238,500 B2 | 3/2019 | Rogers et al. |
| 10,265,191 B2 | 4/2019 | Lim et al. |
| 10,307,254 B2 | 6/2019 | Levy et al. |
| 10,363,142 B2 | 7/2019 | McClintock et al. |
| 10,376,372 B2 | 8/2019 | Serhan et al. |
| 10,398,563 B2 | 9/2019 | Engstrom |
| 10,398,566 B2 | 9/2019 | Olmos et al. |
| 10,405,986 B2 | 9/2019 | Kelly et al. |
| 10,405,989 B2 | 9/2019 | O'Neil et al. |
| 10,420,651 B2 | 9/2019 | Serhan et al. |
| 10,433,971 B2 | 10/2019 | Dimauro et al. |
| 10,433,974 B2 | 10/2019 | O'Neil |
| 10,433,977 B2 | 10/2019 | Lechmann et al. |
| 10,449,056 B2 | 10/2019 | Cain |
| 10,449,058 B2 | 10/2019 | Lechmann et al. |
| 10,470,894 B2 | 11/2019 | Foley et al. |
| 10,492,918 B2 | 12/2019 | Dimauro |
| 10,492,924 B2 | 12/2019 | Stein et al. |
| 10,512,489 B2 | 12/2019 | Serhan et al. |
| 10,537,436 B2 | 1/2020 | Maguire et al. |
| 10,548,741 B2 | 2/2020 | Suedkamp et al. |
| 10,555,817 B2 | 2/2020 | Dimauro et al. |
| 10,575,959 B2 | 3/2020 | Dimauro et al. |
| 10,583,013 B2 | 3/2020 | Dimauro et al. |
| 10,583,015 B2 | 3/2020 | Olmos et al. |
| 10,639,164 B2 | 5/2020 | Dimauro et al. |
| 10,639,166 B2 | 5/2020 | Weiman |
| 10,682,241 B2 | 6/2020 | Glerum et al. |
| 10,743,914 B2 | 8/2020 | Lopez et al. |
| 10,842,644 B2 | 11/2020 | Weiman et al. |
| 10,888,433 B2 | 1/2021 | Frasier et al. |
| 10,966,840 B2 | 4/2021 | Voellmicke et al. |
| 10,973,652 B2 | 4/2021 | Hawkins et al. |
| 11,051,954 B2 | 7/2021 | Greenhalgh et al. |
| 2001/0011174 A1 | 8/2001 | Reiley et al. |
| 2001/0012950 A1 | 8/2001 | Nishtala et al. |
| 2001/0016741 A1 | 8/2001 | Burkus et al. |
| 2001/0016775 A1 | 8/2001 | Scarborough et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0039453 A1 | 11/2001 | Gresser et al. |
| 2001/0049529 A1 | 12/2001 | Cachia et al. |
| 2001/0049530 A1 | 12/2001 | Culbert et al. |
| 2001/0049531 A1 | 12/2001 | Reiley et al. |
| 2001/0056302 A1 | 12/2001 | Boyer |
| 2002/0001476 A1 | 1/2002 | Nagamine et al. |
| 2002/0010070 A1 | 1/2002 | Cales et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045904 A1 | 4/2002 | Fuss et al. |
| 2002/0045942 A1 | 4/2002 | Ham |
| 2002/0045943 A1 | 4/2002 | Uk |
| 2002/0055740 A1 | 5/2002 | Lieberman |
| 2002/0055781 A1 | 5/2002 | Sazy |
| 2002/0058947 A1 | 5/2002 | Hochschuler et al. |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0072801 A1 | 6/2002 | Michelson |
| 2002/0077700 A1 | 6/2002 | Varga et al. |
| 2002/0077701 A1 | 6/2002 | Kuslich |
| 2002/0082584 A1 | 6/2002 | Rosenman et al. |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0091387 A1 | 7/2002 | Hoogland |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0128713 A1 | 9/2002 | Ferree |
| 2002/0128715 A1 | 9/2002 | Bryan et al. |
| 2002/0128716 A1 | 9/2002 | Cohen et al. |
| 2002/0138078 A1 | 9/2002 | Chappuis |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2002/0151976 A1 | 10/2002 | Foley et al. |
| 2002/0156482 A1 | 10/2002 | Scribner et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014113 A1 | 1/2003 | Ralph et al. |

(56) References Cited

U.S. PATENT DOCUMENTS

| | | |
|---|---|---|
| 2003/0014116 A1 | 1/2003 | Ralph et al. |
| 2003/0018390 A1 | 1/2003 | Husson |
| 2003/0023305 A1 | 1/2003 | McKay |
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0045939 A1 | 3/2003 | Casutt |
| 2003/0050644 A1 | 3/2003 | Boucher et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074063 A1 | 4/2003 | Gerbec et al. |
| 2003/0074075 A1 | 4/2003 | Thomas et al. |
| 2003/0078667 A1 | 4/2003 | Manasas et al. |
| 2003/0083642 A1 | 5/2003 | Boyd et al. |
| 2003/0083688 A1 | 5/2003 | Simonson |
| 2003/0108588 A1 | 6/2003 | Chen et al. |
| 2003/0130664 A1 | 7/2003 | Boucher et al. |
| 2003/0130739 A1 | 7/2003 | Gerbec et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0153874 A1 | 8/2003 | Tal |
| 2003/0171812 A1 | 9/2003 | Grunberg et al. |
| 2003/0187431 A1 | 10/2003 | Simonson |
| 2003/0187445 A1 | 10/2003 | Keith et al. |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0191531 A1 | 10/2003 | Berry et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin |
| 2003/0204261 A1 | 10/2003 | Eisermann et al. |
| 2003/0208122 A1 | 11/2003 | Melkent et al. |
| 2003/0208136 A1 | 11/2003 | Mark et al. |
| 2003/0208220 A1 | 11/2003 | Worley et al. |
| 2003/0208270 A9 | 11/2003 | Michelson |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0002761 A1 | 1/2004 | Rogers et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034343 A1 | 2/2004 | Gillespie et al. |
| 2004/0034429 A1 | 2/2004 | Lambrecht et al. |
| 2004/0049190 A1 | 3/2004 | Biedermann et al. |
| 2004/0049203 A1 | 3/2004 | Scribner et al. |
| 2004/0049223 A1 | 3/2004 | Nishtala et al. |
| 2004/0049270 A1 | 3/2004 | Gewirtz |
| 2004/0054412 A1 | 3/2004 | Gerbec et al. |
| 2004/0059333 A1 | 3/2004 | Carl et al. |
| 2004/0059337 A1 | 3/2004 | Hanson et al. |
| 2004/0059339 A1 | 3/2004 | Roehm et al. |
| 2004/0059350 A1 | 3/2004 | Gordon et al. |
| 2004/0059418 A1 | 3/2004 | McKay et al. |
| 2004/0064144 A1 | 4/2004 | Johnson et al. |
| 2004/0068269 A1 | 4/2004 | Bonati et al. |
| 2004/0073308 A1 | 4/2004 | Kuslich et al. |
| 2004/0073310 A1 | 4/2004 | Moumene et al. |
| 2004/0082953 A1 | 4/2004 | Petit |
| 2004/0083000 A1 | 4/2004 | Keller et al. |
| 2004/0087947 A1 | 5/2004 | Lim et al. |
| 2004/0088055 A1 | 5/2004 | Hanson |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0093083 A1 | 5/2004 | Branch |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0102784 A1 | 5/2004 | Pasquet et al. |
| 2004/0102846 A1 | 5/2004 | Keller et al. |
| 2004/0106925 A1 | 6/2004 | Culbert |
| 2004/0106940 A1 | 6/2004 | Shaolian et al. |
| 2004/0111161 A1 | 6/2004 | Trieu |
| 2004/0116997 A1 | 6/2004 | Taylor et al. |
| 2004/0117019 A1 | 6/2004 | Trieu et al. |
| 2004/0117022 A1 | 6/2004 | Marnay et al. |
| 2004/0127906 A1 | 7/2004 | Culbert et al. |
| 2004/0127990 A1 | 7/2004 | Bartish et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147129 A1 | 7/2004 | Rolfson |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153065 A1 | 8/2004 | Lim |
| 2004/0153115 A1 | 8/2004 | Reiley et al. |
| 2004/0153156 A1* | 8/2004 | Cohen ............... A61F 2/442 623/17.13 |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0172134 A1 | 9/2004 | Berry |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193271 A1 | 9/2004 | Fraser et al. |
| 2004/0193277 A1 | 9/2004 | Long et al. |
| 2004/0199162 A1 | 10/2004 | Von et al. |
| 2004/0210231 A1 | 10/2004 | Boucher et al. |
| 2004/0210310 A1 | 10/2004 | Trieu |
| 2004/0215343 A1 | 10/2004 | Hochschuler et al. |

(56) References Cited

U.S. PATENT DOCUMENTS

| | | |
|---|---|---|
| 2004/0215344 A1 | 10/2004 | Hochschuler et al. |
| 2004/0220580 A1 | 11/2004 | Johnson et al. |
| 2004/0220668 A1 | 11/2004 | Eisermann et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro et al. |
| 2004/0243229 A1 | 12/2004 | Vidlund et al. |
| 2004/0243239 A1 | 12/2004 | Taylor |
| 2004/0243241 A1 | 12/2004 | Istephanous et al. |
| 2004/0249377 A1 | 12/2004 | Kaes et al. |
| 2004/0249461 A1 | 12/2004 | Ferree |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254643 A1 | 12/2004 | Jackson |
| 2004/0254644 A1 | 12/2004 | Taylor |
| 2004/0260297 A1 | 12/2004 | Padget et al. |
| 2004/0260300 A1 | 12/2004 | Gorensek et al. |
| 2004/0260397 A1 | 12/2004 | Lambrecht et al. |
| 2004/0266257 A1 | 12/2004 | Ries et al. |
| 2004/0267271 A9 | 12/2004 | Scribner et al. |
| 2004/0267367 A1 | 12/2004 | O'Neil |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0021041 A1 | 1/2005 | Michelson |
| 2005/0033289 A1 | 2/2005 | Warren et al. |
| 2005/0033295 A1 | 2/2005 | Wisnewski |
| 2005/0033434 A1 | 2/2005 | Berry |
| 2005/0033440 A1 | 2/2005 | Lambrecht et al. |
| 2005/0038431 A1 | 2/2005 | Bartish et al. |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0043800 A1 | 2/2005 | Paul et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080443 A1 | 4/2005 | Fallin et al. |
| 2005/0080488 A1 | 4/2005 | Schultz |
| 2005/0085912 A1 | 4/2005 | Arnin et al. |
| 2005/0090443 A1 | 4/2005 | Michael John |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0096745 A1 | 5/2005 | Andre et al. |
| 2005/0102202 A1 | 5/2005 | Linden et al. |
| 2005/0107880 A1 | 5/2005 | Shimp et al. |
| 2005/0113916 A1 | 5/2005 | Branch, Jr. |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125061 A1 | 6/2005 | Zucherman et al. |
| 2005/0125062 A1 | 6/2005 | Biedermann et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131536 A1 | 6/2005 | Eisermann et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0137602 A1 | 6/2005 | Assell et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149030 A1 | 7/2005 | Serhan et al. |
| 2005/0149034 A1 | 7/2005 | Assell et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0165398 A1 | 7/2005 | Reiley |
| 2005/0165406 A1 | 7/2005 | Assell et al. |
| 2005/0165420 A1 | 7/2005 | Cha |
| 2005/0165484 A1 | 7/2005 | Ferree |
| 2005/0165485 A1 | 7/2005 | Trieu |
| 2005/0171539 A1 | 8/2005 | Braun et al. |
| 2005/0171541 A1 | 8/2005 | Boehm et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177173 A1 | 8/2005 | Aebi et al. |
| 2005/0177235 A1 | 8/2005 | Baynham et al. |
| 2005/0177240 A1 | 8/2005 | Blain |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Culbert |
| 2005/0216081 A1 | 9/2005 | Taylor |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |

(56) References Cited

U.S. PATENT DOCUMENTS

| | | |
|---|---|---|
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde, Jr. |
| 2005/0278029 A1 | 12/2005 | Trieu |
| 2005/0283238 A1 | 12/2005 | Reiley |
| 2005/0283244 A1 | 12/2005 | Gordon et al. |
| 2005/0287071 A1 | 12/2005 | Wenz |
| 2006/0004326 A1 | 1/2006 | Collins et al. |
| 2006/0004456 A1 | 1/2006 | McKay |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0020284 A1 | 1/2006 | Foley et al. |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0036241 A1 | 2/2006 | Siegal |
| 2006/0036244 A1 | 2/2006 | Spitler et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036273 A1 | 2/2006 | Siegal |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0064101 A1 | 3/2006 | Arramon |
| 2006/0064102 A1 | 3/2006 | Ebner |
| 2006/0064171 A1 | 3/2006 | Trieu |
| 2006/0064172 A1 | 3/2006 | Trieu |
| 2006/0069436 A1 | 3/2006 | Sutton et al. |
| 2006/0069439 A1 | 3/2006 | Zucherman et al. |
| 2006/0069440 A1 | 3/2006 | Zucherman et al. |
| 2006/0074429 A1 | 4/2006 | Ralph et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0084988 A1 | 4/2006 | Kim |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100622 A1 | 5/2006 | Jackson |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111715 A1 | 5/2006 | Jackson |
| 2006/0111728 A1 | 5/2006 | Abdou |
| 2006/0111785 A1 | 5/2006 | O'Neil |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | Dinello et al. |
| 2006/0136064 A1 | 6/2006 | Sherman |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149229 A1 | 7/2006 | Kwak et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0149385 A1 | 7/2006 | McKay |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167547 A1 | 7/2006 | Suddaby |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0212118 A1 | 9/2006 | Abernathie |
| 2006/0217711 A1 | 9/2006 | Stevens et al. |
| 2006/0229627 A1 | 10/2006 | Hunt et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241643 A1 | 10/2006 | Lim et al. |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0253120 A1 | 11/2006 | Anderson et al. |
| 2006/0253201 A1* | 11/2006 | McLuen ............... A61F 2/447 623/17.15 |
| 2006/0254784 A1 | 11/2006 | Hartmann et al. |
| 2006/0264896 A1 | 11/2006 | Palmer |
| 2006/0264939 A1 | 11/2006 | Zucherman et al. |
| 2006/0264945 A1 | 11/2006 | Edidin et al. |

(56) References Cited

U.S. PATENT DOCUMENTS

| | | |
|---|---|---|
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0016191 A1 | 1/2007 | Culbert et al. |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055264 A1 | 3/2007 | Parmigiani |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093897 A1 | 4/2007 | Gerbec et al. |
| 2007/0093899 A1 | 4/2007 | Dutoit et al. |
| 2007/0093901 A1 | 4/2007 | Grotz et al. |
| 2007/0093906 A1 | 4/2007 | Hudgins et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0123986 A1 | 5/2007 | Schaller |
| 2007/0129730 A1 | 6/2007 | Woods et al. |
| 2007/0135922 A1 | 6/2007 | Trieu |
| 2007/0142843 A1 | 6/2007 | Dye |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0161992 A1 | 7/2007 | Kwak et al. |
| 2007/0162005 A1 | 7/2007 | Peterson et al. |
| 2007/0162127 A1 | 7/2007 | Peterman et al. |
| 2007/0162132 A1 | 7/2007 | Messerli |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213826 A1 | 9/2007 | Smith et al. |
| 2007/0219634 A1 | 9/2007 | Greenhalgh et al. |
| 2007/0225706 A1 | 9/2007 | Clark et al. |
| 2007/0225726 A1 | 9/2007 | Dye et al. |
| 2007/0225807 A1 | 9/2007 | Phan et al. |
| 2007/0225815 A1 | 9/2007 | Keith et al. |
| 2007/0233074 A1 | 10/2007 | Anderson et al. |
| 2007/0233076 A1 | 10/2007 | Trieu |
| 2007/0233083 A1 | 10/2007 | Abdou |
| 2007/0233089 A1 | 10/2007 | Dipoto et al. |
| 2007/0233130 A1 | 10/2007 | Suddaby |
| 2007/0233244 A1 | 10/2007 | Lopez et al. |
| 2007/0260245 A1 | 11/2007 | Malandain et al. |
| 2007/0260255 A1 | 11/2007 | Haddock et al. |
| 2007/0260314 A1 | 11/2007 | Biyani |
| 2007/0270823 A1 | 11/2007 | Trieu et al. |
| 2007/0270954 A1 | 11/2007 | Wu |
| 2007/0270957 A1 | 11/2007 | Heinz |
| 2007/0270968 A1 | 11/2007 | Baynham et al. |
| 2007/0276373 A1 | 11/2007 | Malandain |
| 2007/0276375 A1 | 11/2007 | Rapp |
| 2007/0276497 A1 | 11/2007 | Anderson |
| 2007/0282443 A1 | 12/2007 | Globerman et al. |
| 2007/0282449 A1 | 12/2007 | De et al. |
| 2007/0288091 A1 | 12/2007 | Braddock et al. |
| 2007/0299521 A1 | 12/2007 | Glenn et al. |
| 2008/0009877 A1 | 1/2008 | Sankaran et al. |
| 2008/0015694 A1 | 1/2008 | Tribus |
| 2008/0015701 A1 | 1/2008 | Garcia et al. |
| 2008/0021556 A1 | 1/2008 | Edie |
| 2008/0021557 A1 | 1/2008 | Trieu |
| 2008/0021558 A1 | 1/2008 | Thramann |
| 2008/0021559 A1 | 1/2008 | Thramann |
| 2008/0027437 A1 | 1/2008 | Johnson et al. |
| 2008/0027438 A1 | 1/2008 | Abdou |
| 2008/0027453 A1 | 1/2008 | Johnson et al. |

(56) References Cited

U.S. PATENT DOCUMENTS

| | | |
|---|---|---|
| 2008/0027454 A1 | 1/2008 | Johnson et al. |
| 2008/0027544 A1 | 1/2008 | Melkent |
| 2008/0027550 A1 | 1/2008 | Link et al. |
| 2008/0033440 A1 | 2/2008 | Moskowitz et al. |
| 2008/0045966 A1 | 2/2008 | Buttermann et al. |
| 2008/0051890 A1 | 2/2008 | Waugh et al. |
| 2008/0051897 A1 | 2/2008 | Lopez et al. |
| 2008/0051902 A1 | 2/2008 | Dwyer |
| 2008/0058598 A1 | 3/2008 | Ries et al. |
| 2008/0058937 A1 | 3/2008 | Malandain et al. |
| 2008/0058944 A1 | 3/2008 | Duplessis et al. |
| 2008/0065082 A1 | 3/2008 | Chang et al. |
| 2008/0065219 A1 | 3/2008 | Dye |
| 2008/0071356 A1 | 3/2008 | Greenhalgh et al. |
| 2008/0071380 A1 | 3/2008 | Sweeney |
| 2008/0077148 A1 | 3/2008 | Ries et al. |
| 2008/0077150 A1 | 3/2008 | Nguyen |
| 2008/0077241 A1 | 3/2008 | Nguyen |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0097454 A1 | 4/2008 | Deridder et al. |
| 2008/0097611 A1 | 4/2008 | Mastrorio et al. |
| 2008/0103601 A1 | 5/2008 | Biro et al. |
| 2008/0108990 A1 | 5/2008 | Mitchell et al. |
| 2008/0108996 A1 | 5/2008 | Padget et al. |
| 2008/0119935 A1 | 5/2008 | Alvarez |
| 2008/0125865 A1 | 5/2008 | Abdelgany |
| 2008/0132934 A1 | 6/2008 | Reiley et al. |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147129 A1 | 6/2008 | Biedermann et al. |
| 2008/0147193 A1 | 6/2008 | Matthis et al. |
| 2008/0154379 A1 | 6/2008 | Steiner et al. |
| 2008/0161927 A1 | 7/2008 | Savage et al. |
| 2008/0167657 A1 | 7/2008 | Greenhalgh |
| 2008/0177306 A1 | 7/2008 | Lamborne et al. |
| 2008/0177312 A1 | 7/2008 | Perez-Cruet et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208255 A1 | 8/2008 | Siegal |
| 2008/0208344 A1 | 8/2008 | Kilpela et al. |
| 2008/0221586 A1 | 9/2008 | Garcia-Bengochea et al. |
| 2008/0221687 A1 | 9/2008 | Viker |
| 2008/0228225 A1 | 9/2008 | Trautwein et al. |
| 2008/0229597 A1 | 9/2008 | Malandain |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243251 A1 | 10/2008 | Stad et al. |
| 2008/0243254 A1 | 10/2008 | Butler |
| 2008/0249622 A1 | 10/2008 | Gray |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2008/0312743 A1 | 12/2008 | Vila et al. |
| 2008/0319477 A1 | 12/2008 | Justis et al. |
| 2009/0005870 A1 | 1/2009 | Hawkins et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054898 A1 | 2/2009 | Gleason |
| 2009/0054911 A1 | 2/2009 | Mueller et al. |
| 2009/0054988 A1 | 2/2009 | Hess |
| 2009/0054991 A1 | 2/2009 | Biyani et al. |
| 2009/0062807 A1 | 3/2009 | Song |
| 2009/0069813 A1 | 3/2009 | Von et al. |
| 2009/0069895 A1 | 3/2009 | Gittings et al. |
| 2009/0076607 A1 | 3/2009 | Aalsma et al. |
| 2009/0076610 A1 | 3/2009 | Afzal |
| 2009/0088789 A1 | 4/2009 | O'Neil et al. |
| 2009/0099568 A1 | 4/2009 | Lowry et al. |
| 2009/0105745 A1 | 4/2009 | Culbert |
| 2009/0112217 A1 | 4/2009 | Hester |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192613 A1 | 7/2009 | Wing et al. |
| 2009/0192614 A1 | 7/2009 | Beger et al. |
| 2009/0216234 A1 | 8/2009 | Farr et al. |
| 2009/0221967 A1 | 9/2009 | Thommen et al. |
| 2009/0222043 A1 | 9/2009 | Altarac et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234389 A1 | 9/2009 | Chuang et al. |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276049 A1 | 11/2009 | Weiland |
| 2009/0276051 A1 | 11/2009 | Arramon et al. |
| 2009/0292361 A1 | 11/2009 | Lopez |
| 2009/0299479 A1 | 12/2009 | Jones et al. |
| 2010/0016905 A1 | 1/2010 | Greenhalgh et al. |
| 2010/0016968 A1 | 1/2010 | Moore |
| 2010/0030217 A1 | 2/2010 | Mitusina |
| 2010/0040332 A1 | 2/2010 | Van et al. |
| 2010/0042218 A1 | 2/2010 | Nebosky et al. |
| 2010/0049324 A1 | 2/2010 | Valdevit et al. |
| 2010/0070036 A1 | 3/2010 | Implicito |
| 2010/0076492 A1 | 3/2010 | Warner et al. |
| 2010/0076502 A1 | 3/2010 | Guyer et al. |
| 2010/0076559 A1 | 3/2010 | Bagga et al. |
| 2010/0082109 A1 | 4/2010 | Greenhalgh et al. |
| 2010/0094422 A1 | 4/2010 | Hansell et al. |
| 2010/0094424 A1 | 4/2010 | Woodburn et al. |
| 2010/0094426 A1 | 4/2010 | Grohowski et al. |
| 2010/0100098 A1 | 4/2010 | Norton et al. |
| 2010/0100183 A1 | 4/2010 | Prewett et al. |
| 2010/0106191 A1 | 4/2010 | Yue et al. |
| 2010/0114147 A1 | 5/2010 | Biyani |
| 2010/0125334 A1 | 5/2010 | Krueger |
| 2010/0174314 A1 | 7/2010 | Mirkovic et al. |
| 2010/0179594 A1 | 7/2010 | Theofilos et al. |
| 2010/0185290 A1 | 7/2010 | Compton et al. |
| 2010/0185292 A1 | 7/2010 | Hochschuler et al. |
| 2010/0191241 A1 | 7/2010 | McCormack et al. |
| 2010/0191334 A1 | 7/2010 | Keller |
| 2010/0191336 A1 | 7/2010 | Greenhalgh |
| 2010/0204795 A1 | 8/2010 | Greenhalgh |
| 2010/0204796 A1 | 8/2010 | Bae et al. |
| 2010/0211107 A1 | 8/2010 | Muhanna |
| 2010/0211176 A1 | 8/2010 | Greenhalgh |
| 2010/0211182 A1 | 8/2010 | Zimmermann |
| 2010/0217269 A1 | 8/2010 | Landes |
| 2010/0222884 A1 | 9/2010 | Greenhalgh |
| 2010/0234849 A1 | 9/2010 | Bouadi |
| 2010/0234956 A1 | 9/2010 | Attia et al. |

(56) References Cited

U.S. PATENT DOCUMENTS

| | | |
|---|---|---|
| 2010/0241231 A1 | 9/2010 | Marino et al. |
| 2010/0256768 A1 | 10/2010 | Lim et al. |
| 2010/0262240 A1 | 10/2010 | Chavatte et al. |
| 2010/0268231 A1 | 10/2010 | Kuslich et al. |
| 2010/0274358 A1 | 10/2010 | Mueller et al. |
| 2010/0286777 A1 | 11/2010 | Errico et al. |
| 2010/0286783 A1 | 11/2010 | Lechmann et al. |
| 2010/0292700 A1 | 11/2010 | Ries |
| 2010/0292796 A1 | 11/2010 | Greenhalgh et al. |
| 2010/0298938 A1 | 11/2010 | Humphreys et al. |
| 2010/0305700 A1 | 12/2010 | Ben-Arye et al. |
| 2010/0305704 A1 | 12/2010 | Messerli et al. |
| 2010/0324607 A1 | 12/2010 | Davis |
| 2010/0324683 A1 | 12/2010 | Reichen et al. |
| 2010/0331845 A1 | 12/2010 | Foley et al. |
| 2010/0331891 A1 | 12/2010 | Culbert et al. |
| 2011/0004216 A1 | 1/2011 | Amendola et al. |
| 2011/0004308 A1 | 1/2011 | Marino et al. |
| 2011/0004310 A1 | 1/2011 | Michelson |
| 2011/0009970 A1 | 1/2011 | Puno |
| 2011/0015747 A1 | 1/2011 | McManus et al. |
| 2011/0029082 A1 | 2/2011 | Hall |
| 2011/0029083 A1 | 2/2011 | Hynes et al. |
| 2011/0029085 A1 | 2/2011 | Hynes et al. |
| 2011/0029086 A1 | 2/2011 | Glazer et al. |
| 2011/0035011 A1 | 2/2011 | Cain |
| 2011/0040332 A1 | 2/2011 | Culbert et al. |
| 2011/0046674 A1 | 2/2011 | Calvosa et al. |
| 2011/0054538 A1 | 3/2011 | Zehavi et al. |
| 2011/0066186 A1 | 3/2011 | Boyer et al. |
| 2011/0071527 A1 | 3/2011 | Nelson et al. |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098818 A1 | 4/2011 | Brodke et al. |
| 2011/0112586 A1 | 5/2011 | Guyer et al. |
| 2011/0130835 A1 | 6/2011 | Ashley et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160773 A1 | 6/2011 | Aschmann et al. |
| 2011/0160861 A1 * | 6/2011 | Jimenez ................ A61F 2/4465 623/17.16 |
| 2011/0160866 A1 | 6/2011 | Laurence et al. |
| 2011/0172716 A1 | 7/2011 | Glerum |
| 2011/0172774 A1 | 7/2011 | Varela |
| 2011/0190816 A1 | 8/2011 | Sheffer et al. |
| 2011/0190891 A1 | 8/2011 | Suh et al. |
| 2011/0230971 A1 | 9/2011 | Donner et al. |
| 2011/0238072 A1 | 9/2011 | Tyndall |
| 2011/0251690 A1 | 10/2011 | Berger et al. |
| 2011/0270261 A1 | 11/2011 | Mast et al. |
| 2011/0270401 A1 | 11/2011 | Mckay |
| 2011/0276142 A1 | 11/2011 | Niemiec et al. |
| 2011/0282453 A1 | 11/2011 | Greenhalgh et al. |
| 2011/0282459 A1 | 11/2011 | McClellan et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2011/0319899 A1 | 12/2011 | O'Neil et al. |
| 2011/0319997 A1 * | 12/2011 | Glerum ................ A61F 2/442 623/17.15 |
| 2011/0319998 A1 | 12/2011 | O'Neil et al. |
| 2011/0320000 A1 | 12/2011 | O'Neil |
| 2012/0004726 A1 | 1/2012 | Greenhalgh et al. |
| 2012/0004732 A1 | 1/2012 | Goel et al. |
| 2012/0006361 A1 | 1/2012 | Miyagi et al. |
| 2012/0010715 A1 | 1/2012 | Spann |
| 2012/0022654 A1 | 1/2012 | Farris et al. |
| 2012/0029636 A1 | 2/2012 | Ragab et al. |
| 2012/0029637 A1 | 2/2012 | Ragab et al. |
| 2012/0029639 A1 | 2/2012 | Blackwell et al. |
| 2012/0035730 A1 | 2/2012 | Spann |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083887 A1 | 4/2012 | Purcell et al. |
| 2012/0083889 A1 | 4/2012 | Purcell et al. |
| 2012/0109319 A1 | 5/2012 | Perisic |
| 2012/0123546 A1 | 5/2012 | Medina |
| 2012/0136443 A1 | 5/2012 | Wenzel |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0191204 A1 | 7/2012 | Bae et al. |
| 2012/0197299 A1 | 8/2012 | Fabian, Jr. |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0209383 A1 | 8/2012 | Tsuang et al. |
| 2012/0215262 A1 | 8/2012 | Culbert et al. |
| 2012/0215315 A1 | 8/2012 | Hochschuler et al. |
| 2012/0215316 A1 | 8/2012 | Mohr et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0253395 A1 | 10/2012 | Linares |
| 2012/0253406 A1 | 10/2012 | Bae et al. |
| 2012/0265309 A1 | 10/2012 | Glerum et al. |
| 2012/0277795 A1 | 11/2012 | Von et al. |
| 2012/0277869 A1 | 11/2012 | Siccardi et al. |
| 2012/0277877 A1 | 11/2012 | Smith et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | Dimauro et al. |
| 2012/0323327 A1 | 12/2012 | McAfee |
| 2012/0323328 A1 | 12/2012 | Weiman |
| 2012/0323329 A1 * | 12/2012 | Jimenez ............... F16H 25/2056 623/17.16 |
| 2012/0330421 A1 | 12/2012 | Weiman |
| 2012/0330422 A1 | 12/2012 | Weiman |
| 2013/0006361 A1 | 1/2013 | Glerum et al. |
| 2013/0006362 A1 | 1/2013 | Biedermann et al. |
| 2013/0023937 A1 | 1/2013 | Biedermann et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0030544 A1 | 1/2013 | Studer |
| 2013/0053966 A1 | 2/2013 | Jimenez et al. |
| 2013/0060337 A1 | 3/2013 | Petersheim et al. |
| 2013/0073044 A1 | 3/2013 | Gamache |
| 2013/0079790 A1 | 3/2013 | Stein et al. |
| 2013/0085572 A1 | 4/2013 | Glerum et al. |
| 2013/0085574 A1 | 4/2013 | Sledge |
| 2013/0109925 A1 | 5/2013 | Horton et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0144391 A1 | 6/2013 | Siegal et al. |
| 2013/0150906 A1 | 6/2013 | Kerboul |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |

(56) References Cited

U.S. PATENT DOCUMENTS

| | | | |
|---|---|---|---|
| 2013/0197642 A1* | 8/2013 | Ernst | A61F 2/442 623/17.16 |
| 2013/0197647 A1 | 8/2013 | Wolters et al. | |
| 2013/0204371 A1 | 8/2013 | McLuen et al. | |
| 2013/0211525 A1 | 8/2013 | McLuen et al. | |
| 2013/0211526 A1 | 8/2013 | Alheidt et al. | |
| 2013/0218276 A1 | 8/2013 | Fiechter et al. | |
| 2013/0231747 A1 | 9/2013 | Olmos et al. | |
| 2013/0238006 A1 | 9/2013 | O'Neil et al. | |
| 2013/0253585 A1 | 9/2013 | Garcia et al. | |
| 2013/0261746 A1 | 10/2013 | Linares et al. | |
| 2013/0261747 A1 | 10/2013 | Geisert | |
| 2013/0268077 A1 | 10/2013 | You et al. | |
| 2013/0274883 A1 | 10/2013 | McLuen et al. | |
| 2013/0310937 A1 | 11/2013 | Pimenta | |
| 2013/0310939 A1 | 11/2013 | Fabian et al. | |
| 2013/0325128 A1 | 12/2013 | Perloff et al. | |
| 2014/0018816 A1 | 1/2014 | Fenn et al. | |
| 2014/0025169 A1 | 1/2014 | Lechmann et al. | |
| 2014/0039622 A1 | 2/2014 | Glerum et al. | |
| 2014/0039626 A1 | 2/2014 | Mitchell | |
| 2014/0046333 A1 | 2/2014 | Johnson et al. | |
| 2014/0046446 A1 | 2/2014 | Robinson | |
| 2014/0052259 A1 | 2/2014 | Garner et al. | |
| 2014/0058512 A1 | 2/2014 | Petersheim | |
| 2014/0058513 A1 | 2/2014 | Gahman et al. | |
| 2014/0067073 A1 | 3/2014 | Hauck | |
| 2014/0081267 A1 | 3/2014 | Orsak et al. | |
| 2014/0086962 A1 | 3/2014 | Jin et al. | |
| 2014/0094916 A1 | 4/2014 | Glerum et al. | |
| 2014/0094917 A1 | 4/2014 | Salerni | |
| 2014/0100662 A1 | 4/2014 | Patterson | |
| 2014/0107790 A1 | 4/2014 | Combrowski | |
| 2014/0114414 A1 | 4/2014 | Abdou et al. | |
| 2014/0114423 A1 | 4/2014 | Suedkamp et al. | |
| 2014/0121774 A1 | 5/2014 | Glerum et al. | |
| 2014/0128977 A1 | 5/2014 | Glerum et al. | |
| 2014/0128980 A1 | 5/2014 | Kirschman | |
| 2014/0135934 A1 | 5/2014 | Hansell et al. | |
| 2014/0142706 A1 | 5/2014 | Hansell et al. | |
| 2014/0148904 A1 | 5/2014 | Robinson | |
| 2014/0163682 A1 | 6/2014 | Lott et al. | |
| 2014/0163683 A1 | 6/2014 | Seifert et al. | |
| 2014/0172105 A1 | 6/2014 | Frasier et al. | |
| 2014/0172106 A1 | 6/2014 | To et al. | |
| 2014/0180421 A1 | 6/2014 | Glerum et al. | |
| 2014/0188225 A1 | 7/2014 | Dmuschewsky | |
| 2014/0228959 A1 | 8/2014 | Niemiec et al. | |
| 2014/0236296 A1 | 8/2014 | Wagner et al. | |
| 2014/0243892 A1 | 8/2014 | Choinski | |
| 2014/0243981 A1 | 8/2014 | Davenport et al. | |
| 2014/0243982 A1 | 8/2014 | Miller | |
| 2014/0249629 A1 | 9/2014 | Moskowitz et al. | |
| 2014/0249630 A1 | 9/2014 | Weiman | |
| 2014/0257484 A1 | 9/2014 | Flower et al. | |
| 2014/0257486 A1 | 9/2014 | Alheidt | |
| 2014/0257494 A1 | 9/2014 | Thorwarth et al. | |
| 2014/0277139 A1 | 9/2014 | Vrionis et al. | |
| 2014/0277204 A1 | 9/2014 | Sandhu | |
| 2014/0277464 A1 | 9/2014 | Richter et al. | |
| 2014/0277473 A1 | 9/2014 | Perrow | |
| 2014/0277474 A1 | 9/2014 | Robinson et al. | |
| 2014/0277476 A1 | 9/2014 | McLean et al. | |
| 2014/0277481 A1 | 9/2014 | Lee et al. | |
| 2014/0277507 A1 | 9/2014 | Baynham | |
| 2014/0296983 A1 | 10/2014 | Fauth et al. | |
| 2014/0303731 A1 | 10/2014 | Glerum | |
| 2014/0303732 A1 | 10/2014 | Rhoda et al. | |
| 2014/0324171 A1 | 10/2014 | Glerum et al. | |
| 2014/0336764 A1 | 11/2014 | Masson et al. | |
| 2014/0336771 A1 | 11/2014 | Zambiasi et al. | |
| 2014/0343678 A1 | 11/2014 | Suddaby et al. | |
| 2015/0012097 A1 | 1/2015 | Ibarra et al. | |
| 2015/0012098 A1 | 1/2015 | Eastlack et al. | |
| 2015/0045894 A1 | 2/2015 | Hawkins et al. | |
| 2015/0057755 A1 | 2/2015 | Suddaby et al. | |
| 2015/0066145 A1 | 3/2015 | Rogers et al. | |
| 2015/0088256 A1 | 3/2015 | Ballard | |
| 2015/0094610 A1 | 4/2015 | Morgenstern et al. | |
| 2015/0094812 A1 | 4/2015 | Cain | |
| 2015/0094813 A1 | 4/2015 | Lechmann et al. | |
| 2015/0094814 A1 | 4/2015 | Emerick et al. | |
| 2015/0100128 A1 | 4/2015 | Glerum et al. | |
| 2015/0112398 A1 | 4/2015 | Morgenstern et al. | |
| 2015/0112437 A1 | 4/2015 | Davis et al. | |
| 2015/0112438 A1 | 4/2015 | McLean | |
| 2015/0164655 A1 | 6/2015 | Dimauro | |
| 2015/0173914 A1 | 6/2015 | Dimauro et al. | |
| 2015/0173916 A1 | 6/2015 | Cain | |
| 2015/0182347 A1 | 7/2015 | Robinson | |
| 2015/0190242 A1 | 7/2015 | Blain et al. | |
| 2015/0196400 A1 | 7/2015 | Dace | |
| 2015/0196401 A1 | 7/2015 | Dimauro et al. | |
| 2015/0202052 A1 | 7/2015 | Dimauro | |
| 2015/0216671 A1 | 8/2015 | Cain | |
| 2015/0216672 A1 | 8/2015 | Cain | |
| 2015/0216673 A1 | 8/2015 | Dimauro | |
| 2015/0223946 A1 | 8/2015 | Weiman | |
| 2015/0230929 A1 | 8/2015 | Lorio | |
| 2015/0230932 A1 | 8/2015 | Schaller | |
| 2015/0238324 A1 | 8/2015 | Nebosky et al. | |
| 2015/0250606 A1 | 9/2015 | McLean | |
| 2015/0272743 A1 | 10/2015 | Jimenez et al. | |
| 2015/0305881 A1 | 10/2015 | Bal et al. | |
| 2015/0320571 A1 | 11/2015 | Lechmann et al. | |
| 2016/0000577 A1 | 1/2016 | Dimauro | |
| 2016/0016309 A1 | 1/2016 | Swift et al. | |
| 2016/0022437 A1 | 1/2016 | Kelly et al. | |
| 2016/0022438 A1 | 1/2016 | Lamborne et al. | |
| 2016/0038301 A1 | 2/2016 | Wickham | |
| 2016/0038304 A1 | 2/2016 | Aquino et al. | |
| 2016/0045333 A1 | 2/2016 | Baynham | |
| 2016/0051373 A1 | 2/2016 | Faulhaber | |
| 2016/0051374 A1 | 2/2016 | Faulhaber | |
| 2016/0051376 A1 | 2/2016 | Serhan et al. | |
| 2016/0058573 A1 | 3/2016 | Dimauro et al. | |
| 2016/0067055 A1 | 3/2016 | Hawkins et al. | |
| 2016/0074170 A1 | 3/2016 | Rogers et al. | |
| 2016/0074175 A1 | 3/2016 | O'Neil | |
| 2016/0081814 A1 | 3/2016 | Baynham | |
| 2016/0089247 A1 | 3/2016 | Nichols et al. | |
| 2016/0100954 A1 | 4/2016 | Rumi et al. | |
| 2016/0106551 A1 | 4/2016 | Grimberg et al. | |
| 2016/0113776 A1* | 4/2016 | Capote | A61F 2/447 623/17.15 |
| 2016/0120660 A1 | 5/2016 | Melkent et al. | |
| 2016/0120662 A1 | 5/2016 | Schaller | |
| 2016/0128843 A1 | 5/2016 | Tsau et al. | |
| 2016/0199195 A1 | 7/2016 | Hauck et al. | |
| 2016/0199196 A1 | 7/2016 | Serhan et al. | |
| 2016/0206440 A1 | 7/2016 | Deridder et al. | |
| 2016/0228258 A1 | 8/2016 | Schaller et al. | |
| 2016/0235455 A1 | 8/2016 | Wahl | |
| 2016/0242929 A1 | 8/2016 | Voellmicke et al. | |
| 2016/0256291 A1 | 9/2016 | Miller | |
| 2016/0310296 A1 | 10/2016 | Dimauro et al. | |
| 2016/0317313 A1 | 11/2016 | Dimauro | |
| 2016/0317317 A1 | 11/2016 | Marchek et al. | |
| 2016/0317714 A1 | 11/2016 | Dimauro et al. | |
| 2016/0331541 A1 | 11/2016 | Dimauro et al. | |
| 2016/0331546 A1 | 11/2016 | Lechmann et al. | |
| 2016/0331548 A1 | 11/2016 | Dimauro et al. | |
| 2016/0338854 A1 | 11/2016 | Serhan et al. | |
| 2016/0367265 A1 | 12/2016 | Morgenstern Lopez | |
| 2016/0367380 A1 | 12/2016 | Dimauro | |
| 2016/0374821 A1 | 12/2016 | Dimauro et al. | |
| 2017/0000622 A1 | 1/2017 | Thommen et al. | |
| 2017/0035578 A1 | 2/2017 | Dimauro et al. | |
| 2017/0056179 A1 | 3/2017 | Lorio | |
| 2017/0071756 A1 | 3/2017 | Slivka et al. | |
| 2017/0100177 A1 | 4/2017 | Kim | |
| 2017/0100255 A1* | 4/2017 | Hleihil | A61F 2/447 |
| 2017/0100260 A1 | 4/2017 | Duffield et al. | |
| 2017/0119542 A1 | 5/2017 | Logan et al. | |

(56) References Cited

U.S. PATENT DOCUMENTS

| | | |
|---|---|---|
| 2017/0128226 A1 | 5/2017 | Faulhaber |
| 2017/0209284 A1 | 7/2017 | Overes et al. |
| 2017/0216045 A1 | 8/2017 | Dewey et al. |
| 2017/0266015 A1 | 9/2017 | Overes et al. |
| 2017/0290674 A1 | 10/2017 | Olmos et al. |
| 2017/0290675 A1 | 10/2017 | Olmos et al. |
| 2017/0290677 A1 | 10/2017 | Olmos et al. |
| 2017/0296352 A1 | 10/2017 | Richerme et al. |
| 2017/0304074 A1 | 10/2017 | Dimauro et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0028200 A1 | 2/2018 | O'Neil et al. |
| 2018/0036141 A1 | 2/2018 | Oneil et al. |
| 2018/0055649 A1 | 3/2018 | Kelly et al. |
| 2018/0071111 A1 | 3/2018 | Sharifi-Mehr et al. |
| 2018/0078379 A1 | 3/2018 | Serhan et al. |
| 2018/0116811 A1 | 5/2018 | Bernard et al. |
| 2018/0161171 A1 | 6/2018 | Frasier et al. |
| 2018/0161175 A1 | 6/2018 | Frasier et al. |
| 2018/0193164 A1 | 7/2018 | Shoshtaev |
| 2018/0256360 A1 | 9/2018 | Cain |
| 2018/0256362 A1 | 9/2018 | Slivka et al. |
| 2019/0008654 A1 | 1/2019 | Thommen |
| 2019/0021868 A1 | 1/2019 | Ludwig et al. |
| 2019/0083276 A1 | 3/2019 | Dimauro |
| 2019/0105171 A1 | 4/2019 | Rogers et al. |
| 2019/0117409 A1 | 4/2019 | Shoshtaev |
| 2019/0133785 A1 | 5/2019 | Georges |
| 2019/0142602 A1 | 5/2019 | Olmos et al. |
| 2019/0269521 A1 | 9/2019 | Shoshtaev |
| 2019/0336301 A1 | 11/2019 | Engstrom |
| 2019/0388238 A1 | 12/2019 | Lechmann et al. |
| 2020/0008950 A1 | 1/2020 | Serhan et al. |
| 2020/0015982 A1 | 1/2020 | O'Neil |
| 2020/0030114 A1 | 1/2020 | Cain |
| 2020/0060843 A1 | 2/2020 | Evans et al. |
| 2020/0078192 A1 | 3/2020 | Marchek et al. |
| 2020/0129308 A1 | 4/2020 | Suedkamp et al. |
| 2020/0297506 A1 | 9/2020 | Olmos et al. |
| 2020/0375754 A1 | 12/2020 | Cain |
| 2020/0375755 A1 | 12/2020 | Cain |
| 2020/0383799 A1 | 12/2020 | Cain |
| 2020/0405497 A1 | 12/2020 | Olmos et al. |
| 2020/0405500 A1 | 12/2020 | Cain |
| 2021/0000160 A1 | 1/2021 | Olmos et al. |
| 2021/0177619 A1 | 6/2021 | Voellmicke et al. |
| 2021/0353427 A1 | 11/2021 | Butler et al. |

FOREIGN PATENT DOCUMENTS

| | | |
|---|---|---|
| CA | 2617872 A1 | 2/2007 |
| CN | 1177918 A | 4/1998 |
| CN | 1383790 A | 12/2002 |
| CN | 1819805 A | 8/2006 |
| CN | 101031260 A | 9/2007 |
| CN | 101087566 A | 12/2007 |
| CN | 101185594 A | 5/2008 |
| CN | 101631516 A | 1/2010 |
| CN | 101909548 A | 12/2010 |
| CN | 102164552 A | 8/2011 |
| CN | 103620249 A | 3/2014 |
| CN | 104023674 A | 9/2014 |
| CN | 104023675 A | 9/2014 |
| CN | 104042366 A | 9/2014 |
| CN | 104822332 A | 8/2015 |
| CN | 104921848 A | 9/2015 |
| CN | 104939876 A | 9/2015 |
| CN | 105025846 A | 11/2015 |
| CN | 105188582 A | 12/2015 |
| CN | 204971722 U | 1/2016 |
| CN | 105769391 A | 7/2016 |
| CN | 105769392 A | 7/2016 |
| CN | 107205829 A | 9/2017 |
| DE | 2804936 A1 | 8/1979 |
| DE | 3023353 A1 | 4/1981 |
| DE | 3801459 A1 | 8/1989 |
| DE | 3911610 A1 | 10/1990 |
| DE | 4012622 C1 | 7/1991 |
| DE | 9407806 U1 | 7/1994 |
| DE | 19710392 C1 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| DE | 10357960 B4 | 9/2015 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0509084 A1 | 10/1992 |
| EP | 0525352 A1 | 2/1993 |
| EP | 0529275 A2 | 3/1993 |
| EP | 0609084 A2 | 8/1994 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0853929 A2 | 7/1998 |
| EP | 1046376 A1 | 10/2000 |
| EP | 1157676 A1 | 11/2001 |
| EP | 1283026 A2 | 2/2003 |
| EP | 1290985 A2 | 3/2003 |
| EP | 1308132 A2 | 5/2003 |
| EP | 1374784 A1 | 1/2004 |
| EP | 1378205 A1 | 1/2004 |
| EP | 1405602 A1 | 4/2004 |
| EP | 1532949 A1 | 5/2005 |
| EP | 1541096 A1 | 6/2005 |
| EP | 1605836 A1 | 12/2005 |
| EP | 1385449 B1 | 7/2006 |
| EP | 1683593 A2 | 7/2006 |
| EP | 1698305 A1 | 9/2006 |
| EP | 1829486 A1 | 9/2007 |
| EP | 1843723 A1 | 10/2007 |
| EP | 1845874 A1 | 10/2007 |
| EP | 1924227 A2 | 5/2008 |
| EP | 1925272 | 5/2008 |
| EP | 2331023 A2 | 6/2011 |
| EP | 2368529 A1 | 9/2011 |
| EP | 2237748 B1 | 9/2012 |
| EP | 2641571 A1 | 9/2013 |
| EP | 2705809 A1 | 3/2014 |
| EP | 2764851 A1 | 8/2014 |
| EP | 2777633 | 9/2014 |
| EP | 2645965 B1 | 8/2016 |
| EP | 3263072 A1 | 1/2018 |
| EP | 3366263 A1 | 8/2018 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2913331 A1 | 9/2008 |
| FR | 2948277 | 1/2011 |
| FR | 3026294 | 4/2016 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 07-213533 A | 8/1995 |
| JP | 10-085232 A | 4/1998 |
| JP | 11-089854 A | 4/1999 |

(56) References Cited

FOREIGN PATENT DOCUMENTS

| | | |
|---|---|---|
| JP | 2003-010197 A | 1/2003 |
| JP | 2003-126266 A | 5/2003 |
| JP | 2003-526457 A | 9/2003 |
| JP | 2006-501901 A | 1/2006 |
| JP | 2006-516456 | 7/2006 |
| JP | 2007-054666 A | 3/2007 |
| JP | 2007-530243 A | 11/2007 |
| JP | 2008-507363 A | 3/2008 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 2012-508048 A | 4/2012 |
| JP | 4988203 B2 | 8/2012 |
| JP | 2013-508031 | 3/2013 |
| JP | 5164571 B2 | 3/2013 |
| JP | 2013-516206 A | 5/2013 |
| JP | 2014-502867 A | 2/2014 |
| JP | 2015-500707 A | 1/2015 |
| JP | 2015-525652 A | 9/2015 |
| JP | 2017-505196 A | 2/2017 |
| WO | 91/09572 A1 | 7/1991 |
| WO | 92/04423 A2 | 3/1992 |
| WO | 92/07594 A1 | 5/1992 |
| WO | 92/14423 A1 | 9/1992 |
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 95/31158 | 11/1995 |
| WO | 96/28100 A1 | 9/1996 |
| WO | 97/00054 A1 | 1/1997 |
| WO | 97/26847 A1 | 7/1997 |
| WO | 98/34552 A1 | 8/1998 |
| WO | 98/34568 A1 | 8/1998 |
| WO | 99/02214 A1 | 1/1999 |
| WO | 99/26562 A1 | 6/1999 |
| WO | 99/42062 A1 | 8/1999 |
| WO | 99/52478 A1 | 10/1999 |
| WO | 99/53871 A1 | 10/1999 |
| WO | 99/60956 A1 | 12/1999 |
| WO | 99/62417 A1 | 12/1999 |
| WO | 00/12033 | 3/2000 |
| WO | 00/13620 A1 | 3/2000 |
| WO | 00/24343 A1 | 5/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/10316 A1 | 2/2001 |
| WO | 01/12054 A2 | 2/2001 |
| WO | 01/17464 A1 | 3/2001 |
| WO | 01/80751 A1 | 11/2001 |
| WO | 01/95838 A1 | 12/2001 |
| WO | 02/03870 A1 | 1/2002 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/45627 A1 | 6/2002 |
| WO | 02/47563 A1 | 6/2002 |
| WO | 02/71921 A2 | 9/2002 |
| WO | 02/85250 A2 | 10/2002 |
| WO | 03/02021 A2 | 1/2003 |
| WO | 03/05937 A1 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 03/03951 A1 | 6/2003 |
| WO | 2003/101308 A1 | 12/2003 |
| WO | 2004/008949 A2 | 1/2004 |
| WO | 03/59180 A2 | 3/2004 |
| WO | 2004/030582 A2 | 4/2004 |
| WO | 2004/034924 A2 | 4/2004 |
| WO | 2004/062505 A1 | 7/2004 |
| WO | 2004/064603 A2 | 8/2004 |
| WO | 2004/069033 A2 | 8/2004 |
| WO | 2004/073563 A2 | 9/2004 |
| WO | 2004/078220 A2 | 9/2004 |
| WO | 2004/078221 A2 | 9/2004 |
| WO | 2004/080316 A1 | 9/2004 |
| WO | 2004/082526 A2 | 9/2004 |
| WO | 2004/098420 A2 | 11/2004 |
| WO | 2004/098453 A2 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/094297 A2 | 10/2005 |
| WO | 2005/112834 A2 | 12/2005 |
| WO | 2005/112835 A2 | 12/2005 |
| WO | 2005/115261 A1 | 12/2005 |
| WO | 2006/017507 A2 | 2/2006 |
| WO | 2006/044920 A2 | 4/2006 |
| WO | 2006/047587 A2 | 5/2006 |
| WO | 2006/047645 A2 | 5/2006 |
| WO | 2006/058079 A2 | 6/2006 |
| WO | 2006/058281 A2 | 6/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/081843 A1 | 8/2006 |
| WO | 2006/108067 A2 | 10/2006 |
| WO | 2006/118944 A1 | 11/2006 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2007/119212 A2 | 10/2007 |
| WO | 2007/124130 A2 | 11/2007 |
| WO | 2008/005627 A2 | 1/2008 |
| WO | 2008/011378 A1 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/011348 A1 | 1/2010 |
| WO | 2010/068725 A2 | 6/2010 |
| WO | 2010/075451 A1 | 7/2010 |
| WO | 2010/075555 A1 | 7/2010 |
| WO | 2010/088766 A1 | 8/2010 |
| WO | 2010/121002 A1 | 10/2010 |
| WO | 2010/136170 A1 | 12/2010 |
| WO | 2010/148112 A1 | 12/2010 |
| WO | 2011/013047 A2 | 2/2011 |
| WO | 2011/046459 A1 | 4/2011 |
| WO | 2011/046460 A1 | 4/2011 |
| WO | 2011/060087 A1 | 5/2011 |
| WO | 2011/079910 A2 | 7/2011 |
| WO | 2011/119617 A1 | 9/2011 |
| WO | 2011/142761 A1 | 11/2011 |
| WO | 2011/150350 A1 | 12/2011 |

(56) References Cited

FOREIGN PATENT DOCUMENTS

| | | |
|---|---|---|
| WO | 2012/009152 A1 | 1/2012 |
| WO | 2012/027490 A2 | 3/2012 |
| WO | 2012/028182 A1 | 3/2012 |
| WO | 2012/030331 A1 | 3/2012 |
| WO | 2012/089317 A1 | 7/2012 |
| WO | 2012/103254 A2 | 8/2012 |
| WO | 2012/122294 A1 | 9/2012 |
| WO | 2012/129197 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/148176 A1 | 10/2013 |
| WO | 2013/149611 A1 | 10/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/004660 A1 | 1/2015 |
| WO | 2015/013479 A2 | 1/2015 |
| WO | 2015/022039 A1 | 2/2015 |
| WO | 2015/048997 A1 | 4/2015 |
| WO | 2016/069796 A1 | 5/2016 |
| WO | 2016/118246 A1 | 7/2016 |
| WO | 2016/127139 A1 | 8/2016 |
| WO | 2017/040881 A1 | 3/2017 |
| WO | 2017/136620 A1 | 8/2017 |
| WO | 2018/078148 A1 | 5/2018 |

OTHER PUBLICATIONS

U.S. Appl. No. 60/942,998, Method and Apparatus for Spinal Stabilization, filed Jun. 8, 2007.
U.S. Appl. No. 61/675,975, Expandable Implant, filed Jul. 26, 2012.
U.S. Appl. No. 60/397,588, Method and apparatus for spinal fixation, filed Jul. 19, 2002.
U.S. Appl. No. 60/794,171, Method and apparatus for spinal fixation, filed Apr. 21, 2006.
U.S. Appl. No. 60/424,055, filed Nov. 5, 2002, entitled Method and apparatus for spinal fixation.
Talwar "Insertion loads of the X STOP interspinous process distraction system designed to treat neurogenic intermittent claudication", Eur Spine J. (2006) 15: pp. 908-912.
Spine Solutions Brochure—Prodisc 2001, 16 pages.
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Shin, "Posterior Lumbar Interbody Fusion via a Unilateral Approach", Yonsei Medical Journal, 2006, pp. 319-325, vol. 47(3).
ProMap TM EMG Navigation Probe. Technical Brochure Spineology Inc, Dated May 2009.
Polikeit, "The Importance of the Endplate for Interbody Cages in the Lumbar Spine", Eur. Spine J., 2003, pp. 556-561, vol. 12.
Paul D. Fuchs, "The use of an interspinous implant in conjunction with a graded facetectomy procedure", Spine vol. 30, No. 11, pp. 1266-1272, 2005.
Niosi, "Biomechanical Characterization of the three-dimentional kinematic behavior of the dynesys dynamic stabilization system: an in vitro study", Eur Spine J. (2006), 15: pp. 913-922.
Morgenstern R; "Transforaminal Endoscopic Stenosis Surgery—A Comparative Study of Laser and Reamed Foraminoplasty", in European Musculoskeletal Review, Issue 1, 2009.

Medco Forum, "Percutaneous Lumbar Fixation via PERPOS System From Interventional Spine", Oct. 2007, vol. 14, No. 49.
Medco Forum, "Percutaneous Lumbar Fixation Via PERPOS PLS System Interventional Spine", Sep. 2008, vol. 15, No. 37.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Link SB Charite Brochure—Intervertebral Prosthesis 1988, 29 pages.
Krbec, "Replacement of the Vertebral Body with an Expansion Implant (Synex)", Acta Chir Orthop Traumatol Cech, 2002, pp. 158-162, vol. 69(3).
King, M.D., Don, "Internal Fixation for Lumbosacral Fusion", The Journal of Bone and Joint Surgery, J. Bone Joint Surg Am., 1948; 30: 560-578.
Kambin et al., "Percutaneous Lateral Discectomy of the Lumbar Spine: A Preliminary Report", Clin. Orthop,: 1983, 174: 127-132.
Iprenburg et al., "Transforaminal Endocopic Surgery in Lumbar Disc Herniation in an Economic crises—The Tessys Method", US Musculoskeletal, 2008, pp. 47-49.
Hunt, "Expandable Cage Placement Via a Posterolateral Approach in Lumbar Spine Reconstructions", Journal of Neurosurgery: Spine, Sep. 2006, pp. 271-274, vol. 5.
Hoogland et al., "Total Lumar Intervertebral Disc Replacement: Testing a New Articulating Space in Human Cadaver Spines—241", Annual ORS, Dallas, TX, Feb. 21-23, 1978, 8 pages.
Grays Anatomy, Crown Publishers, Inc., 1977, pp. 33-54.
Gore, "Technique of Cervical Interbody Fusion", Clinical Orthopaedics and Related Research, Sep. 1984, pp. 191-195, No. 188.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Chin, "Early Results of the Triage Medical Percutaneous Transfacet Pedicular BONE-LOK Compression Device for Lumbar Fusion", Accessed online Jul. 10, 2017, 10 pages.
Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.
Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.
Brochure for PERPOS PLS System Surgical Technique by Interventional Spine, 2008, 8 pages.
Alfen et al., "Developments in the area of Endoscopic Spine Surgery", European Musculoskeletal Review 2006, pp. 23-24, Thessys(Trademark), Transforaminal Endoscopic Spine Systems, joi max Medical Solutions.
Barakat et al., Macromolecular engineering of polylactone and polylactide. XXI. Controlled synthesis of low molecular weight polylactide macromonomers. J Polym Sci Polym Chem 34:497-502, 1996.
Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.
Bruder et al., Monoclonal antibodies reactive with human osteogenic cell surface antigens. Bone. Sep. 1997;21 (3):225-235.
Burkoth et al., A review of photocrosslinked polyanhydrides: in situ forming degradable networks. Biomaterials. Dec. 2000; 21 (23): 2395-2404.
Cambridge Scientific News, FDA Approves Cambridge Scientific, Inc.'s Orthopedic WISORB (TM) Malleolar Screw [online], Jul. 30, 2002 [retrieved on Oct. 14, 2003]. Retrieved from the Internet <URL: http://www.cambridgescientificinc.com>.
Carrino, John A., Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.

(56) References Cited

OTHER PUBLICATIONS

Cheng, B.C., Ph.D., Biomechanical pullout strength and histology of Plasmapore Registered XP coated implants: Ovine multi time point survival study. Aesculap Implant Systems, LLC, 2013, 12 pages.
Domb, Biodegradable bone cement compositions based on acrylate and epoxide terminated poly(propylene fumarate) oligomers and calcium salt compositions, Biomaterials 17, 1996, 411-417.
Edeland, H.G., "Some Additional Suggestions for an Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998;212:119-132.
Ha et al. (Topographical characterization and microstructural interface analysis of vacuum-plasma-sprayed titanium and hydroxyapatite coatings on carbon fiber-reinforced poly(etheretherketone), Journal of Materials Science: Materials in Science 9 (1997), pp. 891-896.
Haas, Norbert P., New Products from AO Development [online], May 2002 [retrieved on Oct. 14, 2003]. Retrieved from the Internet <URL: http://www.ao.asif.ch/development/pdf_tk_news_02_pdf>.
Hao et al., Investigation of nanocomposites based on semi-interpenetrating network of [L-poly (epsilon-caprolactone)]/[net-poly (epsilon-caprolactone)] and hydroxyapatite nanocrystals. Biomaterials. Apr. 2003;24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
International Patent Application No. PCT /US2013/029014, International Search Report dated Jul. 1, 2013, 7 pages.
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kandziora, Frank, et al., "Biomechanical Analysis of Biodegradable Interbody Fusion Cages Augmented with Poly (propylene Glycol-co-Fumaric Acid)," Spine, 27(15): 1644-1651 (2002).
Kotsias, A., Clinical trial of titanium-coated PEEL cages anterior cervical discectomy and fusion. [Klinishe Untersuching zum Einsatz von titanbeschichteten Polyetheretherketon—Implantaten bei der cervikalen interkorporalen fusion]. Doctoral thesis. Department of Medicine, Charite, University of Medicine Berlin, 2014, 73 pages. (German language document/Engl. summary).
Kricheldorf et al., Polylactides—synthesis, characterization and medical applications. Macromol Symp 103:85-102, 1996.
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci USA. Jan. 30, 2001;98(3):842-7. Epub Jan. 23, 2001.
Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.
Massia et al, An RGD spacing of 440 nm is sufficient for integrin alpha V beta 3-mediated fibroblast spreading and 140 nm for focal contact and stress fiber formation. J Cell Biol 114:1089-1100, 1991.
McAfee et al., Minimally invasive anterior retroperitoneal approach to the lumbar spine: Emphasis on the lateral BAK. Spine. 1998;23(13):1476-84.

Mendez et al., Self-curing acrylic formulations containing PMMA/PCL composites: properties and antibiotic release behavior. J Biomed Mater Res. Jul. 2002;61 (1 ):66-74.
Nguyen et al., Poly(Aryl-Ether-Ether-Ketone) and its Advanced Composites: A Review, Polymer Composites, Apr. 1987, vol. 8, No. 2, pp. 57-73.
OSTEOSET Registered DBM Pellets (Important Medical Information) [online], Nov. 2002 [retrieved on Oct. 14, 2003]. Retrieved from the Internet <URL: http://www.wmt.com/Literature>.
POROCOAT(R) Porous Coating, 1 Page, https://emea.depuysynthese.com/hcp/hip/products/qs/porocoat-porous-coatingemea Accessed on Jul. 31, 2017.
Regan et al., Endoscopic thoracic fusion cage. Atlas of Endoscopic Spine Surgery. Quality Medical Publishing, Inc. 1995;350-354.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate)-diacrylate. Biomaterials. Feb. 2003;24(4 ):571-7.
United States Disctrict Court, Central District of California, Case No. 1 :10-CV-00849-LPS, *Nuvasive, Inc.*, vs., *Globus Medical, Inc.*, Videotaped Deposition of: Luiz Pimenta, M.D., May 9, 2012, 20 pages.
Walsh et al., Preparation of porous composite implant materials by in situ polymerization of porous apatite containing epsilon-caprolactone or methyl methacrylate. Biomaterials. Jun. 2001;22( 11):1205-12.
Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/600/600/620/S20/S045. html>, 2 pages.
CN Office Action dated Apr. 24, 2020 for CN Application No. 201780040910.
U.S. Appl. No. 09/558,057, filed Apr. 26, 2000, entitled Bone Fixation System.
Allcock, "Polyphosphazenes"; The Encyclopedia of Polymer Science; 1988; pp. 31-41; vol. 13; Wiley Intersciences, John Wiley & Sons.
Cohn, "Biodegradable PEO/PLA Block Copolymers"; Journal of Biomedical Materials Research; 1988; pp. 993-1009 vol. 22; John Wiley & Sons, Inc.
Cohn, "Polymer Preprints"; Journal of Biomaterials Research; 1989; p. 498; Biomaterials Research Labortory, Casal Institute of Applied Chemistry, Israel.
Heller, "Poly (Otrho Esters)"; Handbook of Biodegradable Polymers; edited by Domb; et al.; Hardwood Academic Press; 1997; pp. 99-118.
Japanese Office Action for Application No. 2013-542047, dated Sep. 8, 2015 (12 pages).
Japanese Office Action for Application No. 2016-135826, dated Jun. 6, 2017, (7 pages).
Kemnitzer, "Degradable Polymers Derived From the Amino Acid L-Tyrosine"; 1997; pp. 251-272; edited by Domb, et al., Hardwood Academic Press.
Khoo, "Minimally Invasive Correction of Grade I and II Isthmic Spondylolisthesis using AxiaLIF for L5/S1 Fusion", pp. 1-7, Rev B Sep. 15, 2008.
Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.

(56) References Cited

OTHER PUBLICATIONS

Vandorpe, "Biodegradable Polyphosphazenes for Biomedical Applications"; Handbook of Biodegradable Polymers 1997; pp. 161-182; Hardwood Academic Press.

* cited by examiner

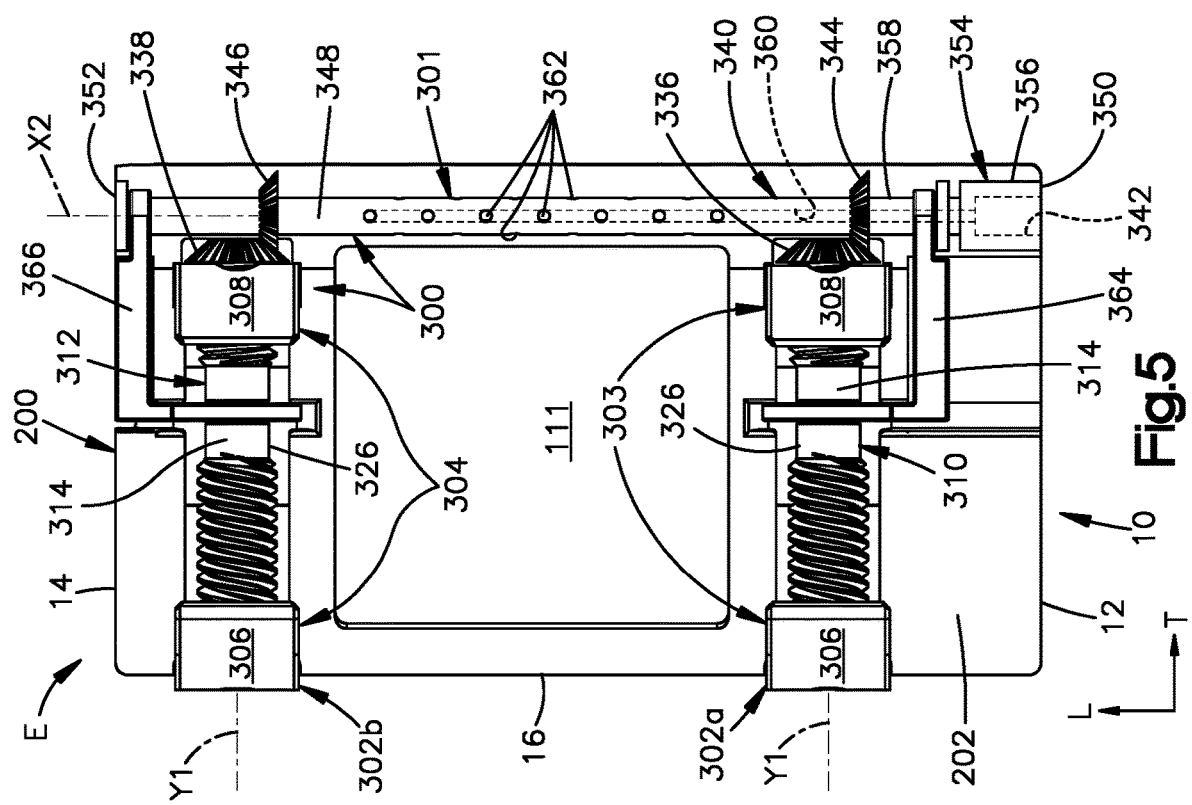
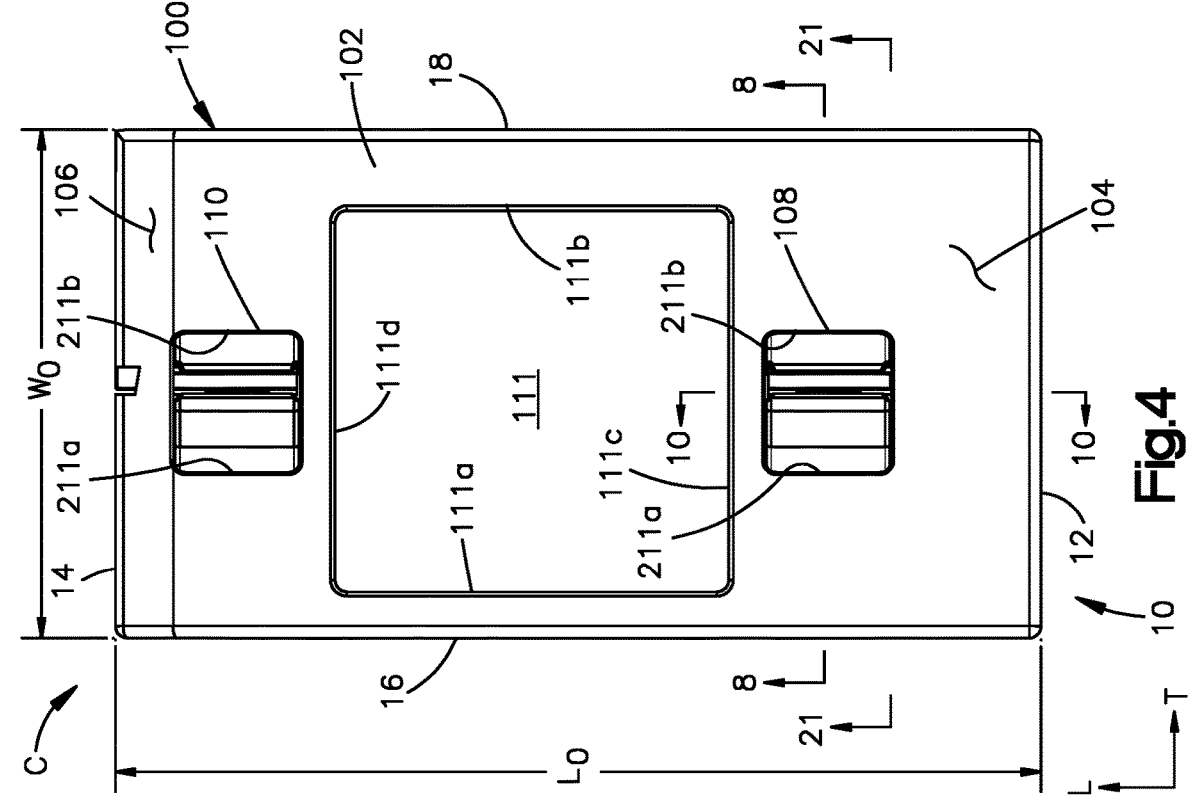

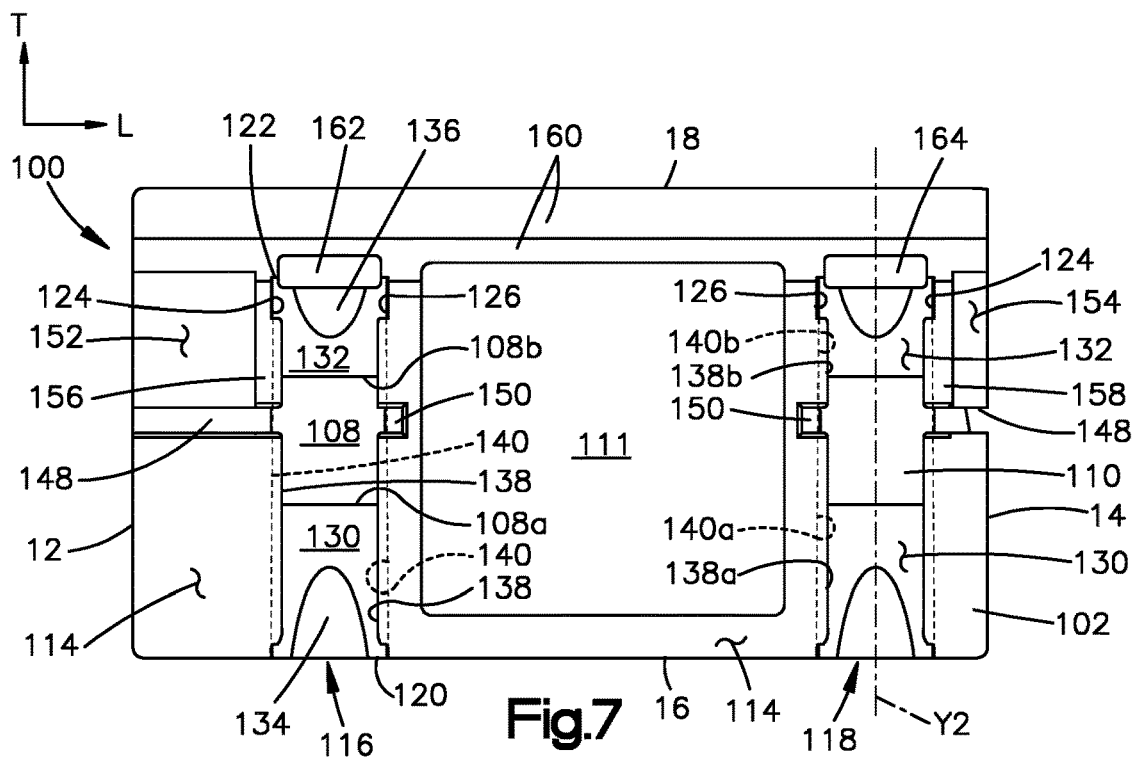
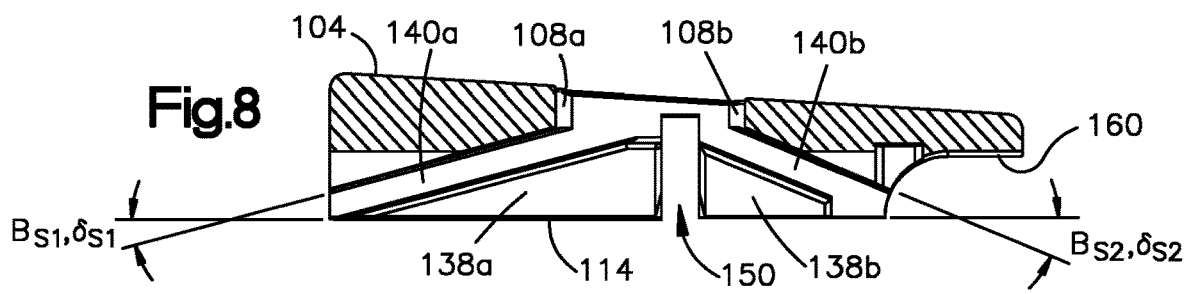
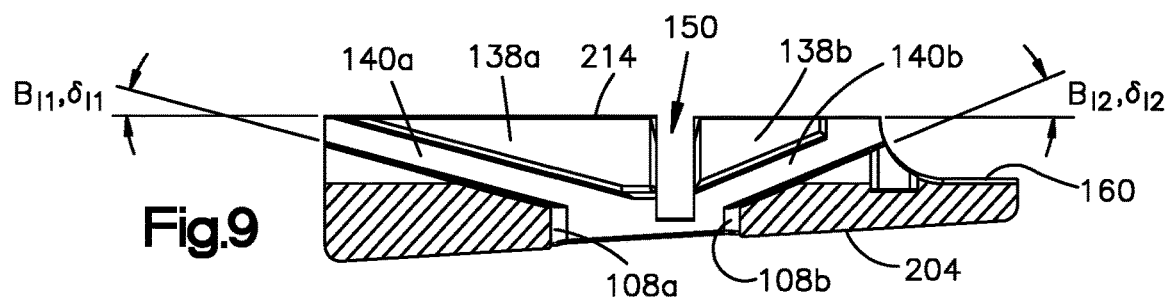
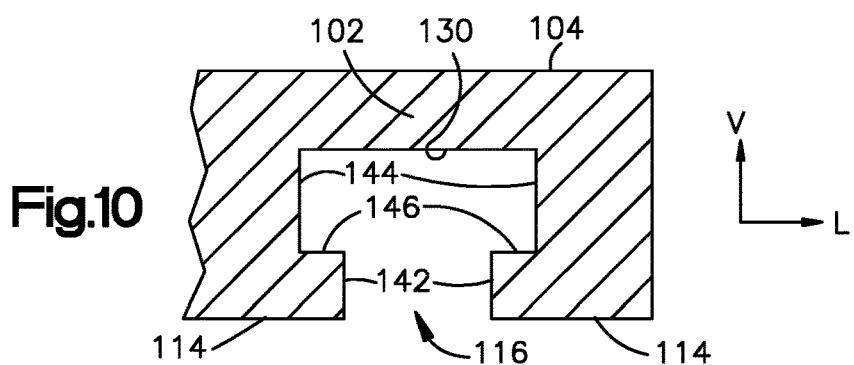

EXPANDABLE INTERVERTEBRAL IMPLANT AND RELATED METHODS

CROSS-REFERENCE TO RELATED APPLICATIONS

This application claims the benefit of U.S. Provisional Patent Application Ser. No. 62/519,470, filed Jun. 14, 2017, in the name of Luu, the entire disclosure of which is hereby incorporated by reference into this patent application.

TECHNICAL FIELD

The present invention relates to an expandable intervertebral implant and related methods.

BACKGROUND

Removal of an intervertebral disc is often desired if the disc degenerates. Spinal fusion may be used to treat such a condition and involves replacing a degenerative disc with a device such as a cage or other spacer that restores the height of the disc space and allows bone growth through the device to fuse the adjacent vertebrae. Spinal fusion attempts to restore normal spinal alignment, stabilize the spinal segment for proper fusion, create an optimal fusion environment, and allows for early active mobilization by minimizing damage to spinal vasculature, dura, and neural elements. When spinal fusion meets these objectives, healing quickens and patient function, comfort and mobility improve. Spacer devices that are impacted into the disc space and allow growth of bone from adjacent vertebral bodies through the upper and lower surfaces of the implant are known in the art. Yet there continues to be a need for devices that minimize procedural invasiveness yet stabilize the spinal segment and create an optimum space for spinal fusion. There also continues to be a need for devices that can be inserted laterally (i.e., along a medial-lateral direction) into the intervertebral space.

SUMMARY

According to an embodiment of the present disclosure, an expandable implant includes a first plate and a second plate spaced from each other along a first direction. The first plate defines a first bone-contacting surface configured to contact a superior vertebral body and the second plate defines a second bone-contacting surface opposed to the first bone contacting surface along the first direction. The second bone contacting surface is configured to contact an inferior vertebral body. The implant includes an actuation member at least partially disposed between the first and second plates with respect to the first direction. The actuation member defines a first axis, a first end and a second end spaced from the first end along a second direction along the first axis. The second direction is perpendicular to the first direction. The implant includes first and second wedge members carried by the actuation member and in engagement with the first and second plates, and also includes a drive member defining a second axis, a proximal end and a distal end spaced from the proximal end along a third direction along the second axis. The third direction is perpendicular to the first direction and offset from the second direction. The drive member is configured to communicate a driving force to the actuation member so as to cause the actuation member to rotate about the first axis, and at least one of the first and second wedge members is configured to translate along the second direction in response to rotation of the actuation member about the first axis so as to move at least one of the first and second plates with respect to the other of the first and second plates along the first direction.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 4 is a top view of the implant shown in FIG. 1 in the collapsed configuration;

FIG. 5 is a top view of the implant shown in FIG. 1 in the expanded configuration, with an upper plate of the implant removed illustrating an expansion mechanism of the implant;

FIG. 7 is a bottom plan view of the upper plate of the implant shown in FIG. 6B;

FIG. 8 is sectional end view of the upper plate of the implant shown in FIG. 7, taken along section line 8-8 in FIG. 4;

FIG. 9 is a sectional end view of the bottom plate of the implant shown in FIG. 7, taken along section line 8-8 in FIG. 4;

FIG. 10 is a sectional view of a portion of the upper plate of the implant, taken along section line 10-10 in FIG. 4;

DETAILED DESCRIPTION OF ILLUSTRATIVE EMBODIMENTS

Figure 1:
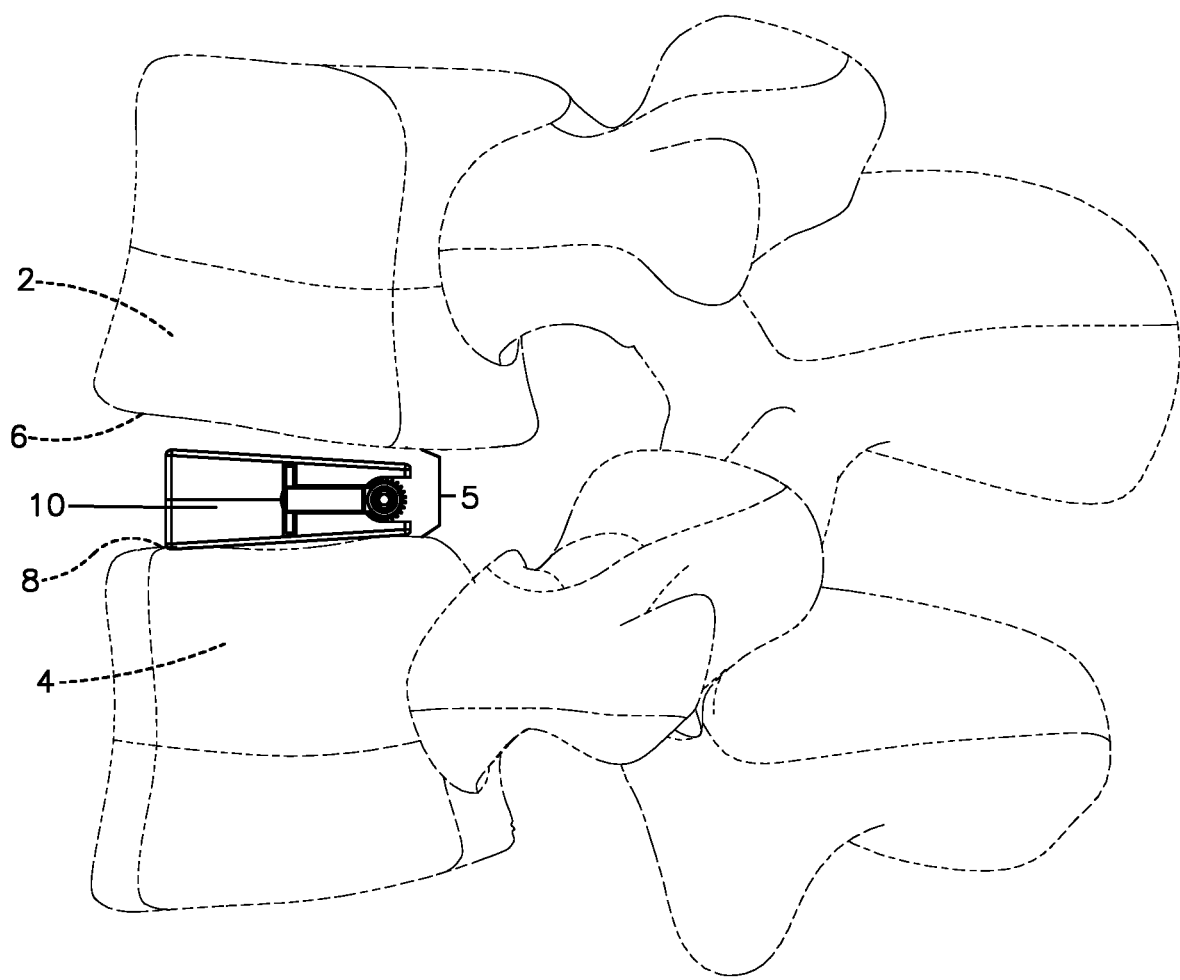
FIG. 1 illustrates an implant positioned between vertebral bodies, according to an embodiment of the present disclosure.

Referring to FIG. 1, a superior vertebral body 2 and an adjacent inferior vertebral body 4 define an intervertebral space 5 extending between the vertebral bodies 2, 4. The superior vertebral body 2 defines superior vertebral surface 6, and the adjacent inferior vertebral body 4 defines an inferior vertebral surface 8. The vertebral bodies 2, 4 can be anatomically adjacent, or can be remaining vertebral bodies after an intermediate vertebral body has been removed from a location between the vertebral bodies 2, 4. The intervertebral space 5 in FIG. 1 is illustrated after a discectomy, whereby the disc material has been removed or at least partially removed to prepare the intervertebral space 5 to receive an expandable intervertebral implant 10. The implant 10 can be configured for lateral insertion (i.e., along a medial-lateral trajectory) within the intervertebral space 5. Once inserted in the intervertebral space 5, the implant 10 can be expanded in a cranial-caudal direction to achieve appropriate height restoration and lordosis, as disclosed in more detail below. The intervertebral space 5 can be disposed anywhere along the spine as desired, including at the lumbar, thoracic, and cervical regions of the spine. It is to be appreciated that certain features of the implant 10 can be similar to those set forth in U.S. Patent Publication No. 2014/0243982 A1, published Aug. 28, 2014 in the name of Miller, the entire disclosure of which is incorporated herein by this reference.

Certain terminology is used in the following description for convenience only and is not limiting. The words "right", "left", "lower" and "upper" designate directions in the drawings to which reference is made. The words "inner", "internal", and "interior" refer to directions towards the geometric center of the implant, while the words "outer", "external", and "exterior" refer to directions away from the geometric center of the implant. The words, "anterior", "posterior", "superior," "inferior," "medial," "lateral," and related words and/or phrases are used to designate various positions and orientations in the human body to which reference is made. When these words are used in relation to the implant 10 or a component thereof, they are to be understood as referring to the relative positions of the implant 10 as implanted in the body as shown in FIG. 1. The terminology includes the above-listed words, derivatives thereof and words of similar import.

Figure 2:
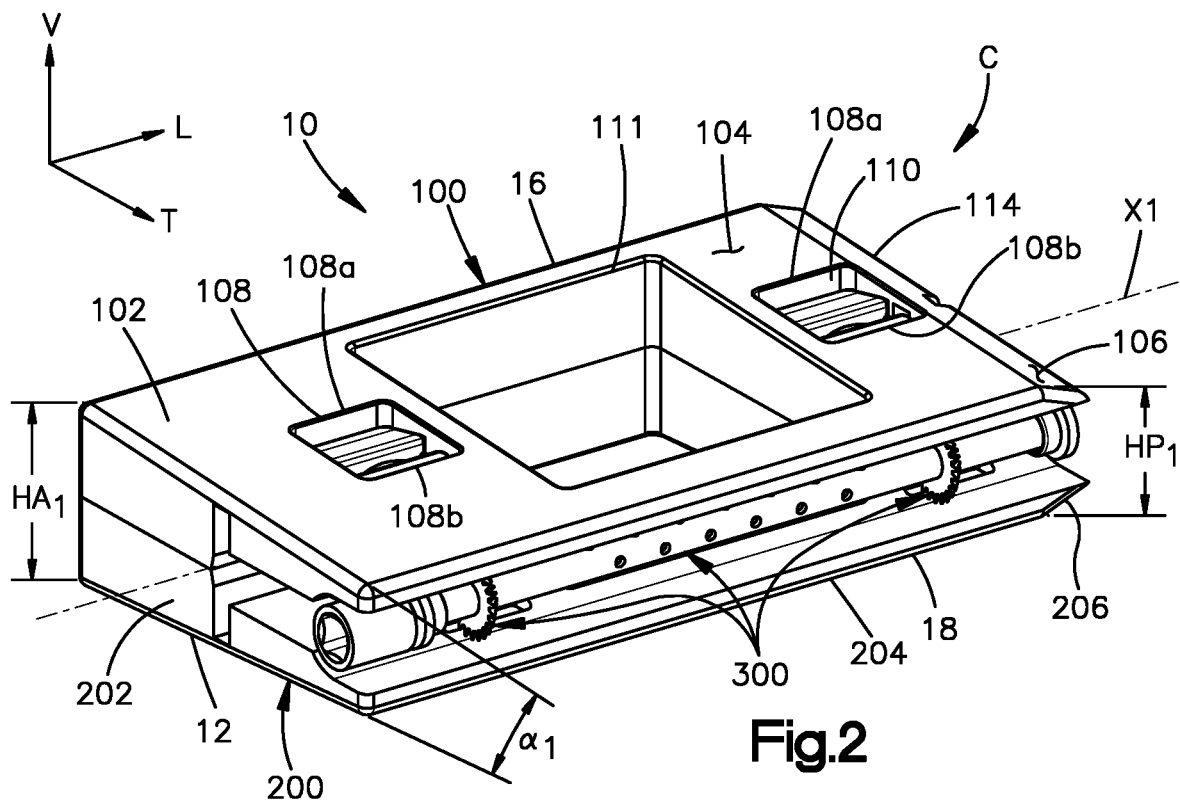
FIG. 2 is a perspective view of the implant shown in FIG. 1 in a collapsed configuration.

Referring now to FIG. 2, the implant 10 is described herein as extending horizontally along a longitudinal direction "L" and a transverse direction "T", and vertically along a vertical direction "V". Unless otherwise specified herein, the terms "longitudinal," "transverse," and "vertical" are used to describe the orthogonal directional components of various implant components and implant component axes. It should be appreciated that while the longitudinal and transverse directions L, T are illustrated as extending along and defining a horizontal plane (also referred to herein as a "longitudinal-transverse plane"), and that the vertical direction is illustrated as extending along a vertical plane (such as either a "vertical-longitudinal plane" or a "vertical-transverse plane," as respectively referred to herein), the planes that encompass the various directions may differ during use. For instance, when the implant 10 is inserted into the intervertebral space 5, the vertical direction V extends generally along the superior-inferior (or caudal-cranial) direction, while the horizontal plane lies generally in the anatomical plane defined by the anterior-posterior direction and the medial-lateral direction. Accordingly, the directional terms "vertical" and "horizontal" may be used to describe the implant 10 and its components as illustrated merely for the purposes of clarity and illustration.

In FIG. 2, the implant 10 is shown in the collapsed configuration C. The implant 10 can extend between a proximal or trailing end 12 and a distal or leading end 14 that is spaced from the leading end 14 along a longitudinal implant axis X1 that extends along the longitudinal direction L. The leading and trailing ends 12, 14 may be respectively termed as such because the implant 10 can be inserted leading-end-first into the intervertebral space 5. The trailing end 12 can be configured to couple with one or more insertion instruments, which are configured to support and carry the implant 10 into the intervertebral space 5. The implant 10 can also extend between an anterior side 16 and a posterior side 18 along the transverse direction T.

The implant 10 can include a first or superior plate 100 and a second or inferior plate 200 opposing the superior plate 100 along the vertical direction V. The superior plate 100 can define a superior plate body 102 that defines a superior or first bone-contacting surface 104 and the inferior plate 200 can define an inferior plate body 202 that defines an inferior or second bone-contacting surface 204 spaced from the first bone-contacting surface 104 along the vertical direction V. The superior and inferior bone-contacting surfaces 104, 204 can be configured to engage the opposing superior and inferior vertebral bodies 4 and 6, respectively. Each bone-contacting surface 104, 204 can extend in a substantially planar fashion, as shown. Additionally, the superior and inferior bone-contacting surfaces 104, 204 can be angled with respect to each other in a vertical-transverse plane so as to define a lordotic angle α of the implant 10. Additionally, to facilitate insertion, the superior and inferior plate bodies 102, 202 can each define a tapered surface 106, 206 adjacent the leading end 14 of the implant 10, wherein each tapered surface 106, 206 tapers inwardly generally toward the vertical midpoint of the implant 10 in a distal direction to facilitate insertion of the implant 10.

While the superior and inferior bone-contacting surfaces 104, 204 are each shown as being substantially planar, in other embodiments, each bone-contacting surface 104, 204 can be substantially convex or at least partially convex, for instance, or can define a portion that is convex and another portion that is planar. The bone-contacting surfaces 104, 204 can also at least partially define a texture (not shown), such as spikes, ridges, cones, barbs, indentations, or knurls, which are configured to engage the respective vertebral bodies 4 and 6 when the implant 10 is inserted into the intervertebral space 5.

As used herein, the term "distal" and derivatives thereof refer to a direction from the trailing end 12 toward the leading end 14. As used herein, the term "proximal" and derivatives thereof refer to a direction from the leading end 14 toward the trailing end 12. Thus, as used herein, the term "longitudinal direction L" is bi-directional and is defined by the mono-directional distal and opposed proximal directions.

As used herein, the term "anterior" and derivatives thereof refer to a direction from the posterior side 18 of the implant 10 toward the anterior side 16 of the implant. As used herein, the term "posterior" and derivatives thereof refer to a direction from the anterior side 16 toward the posterior side 18. Thus, as used herein, the term "transverse direction L"

is bi-directional and is defined by the mono-directional anterior and opposed posterior directions.

As used herein, the term "superior" and derivatives thereof refer to a direction from the second bone-contacting surface 204 toward the first bone-contacting surface 104. As used herein, the term "inferior" and derivatives thereof refer to a direction from the first bone-contacting surface 104 toward the second bone-contacting surface 204. Thus, as used herein, the term "vertical direction V" is bi-directional and is defined by the mono-directional superior and opposed inferior directions.

Figure 3:
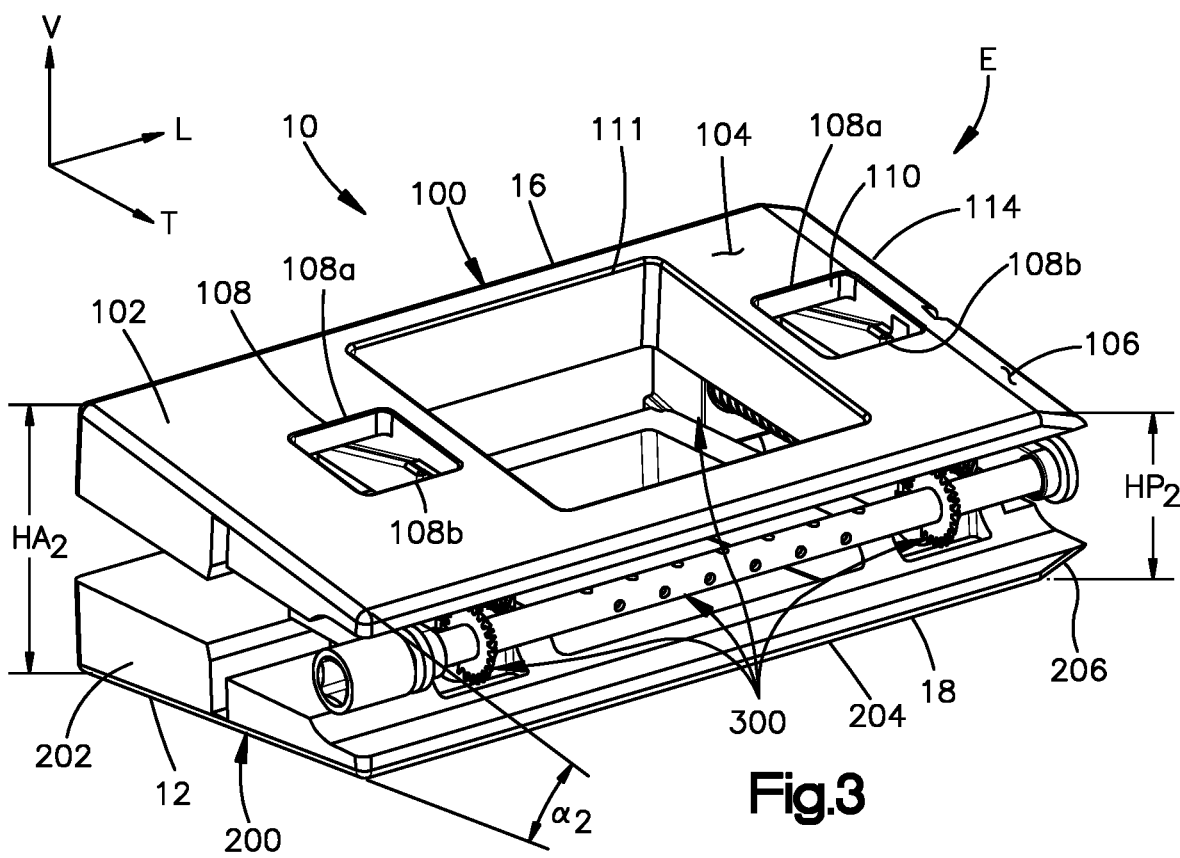
FIG. 3 is a perspective view of the implant shown in FIG. 1 in an expanded configuration.

Referring to FIGS. 2 and 3, the implant 10 can include an expansion mechanism 300 interposed between portions of the superior and inferior plates 100, 200 and configured to separate the superior and inferior plates 100, 200 relative to each other in the vertical direction V. For example, the expansion mechanism 300 can be configured to actuate the implant 10 from the collapsed configuration C, as shown in FIG. 2, into an expanded configuration E, as shown in FIG. 3. The implant 10 can be configured to expand the vertical height and the lordotic angle α of the implant 10, each measured between the superior and inferior bone-contacting surfaces 104, 204. For example, when the implant 10 is in the collapsed configuration (FIG. 2), a collapsed anterior height HA' of the implant 10 can be between about 4 mm and about 18 mm, a collapsed posterior height HP1 of the implant 10 can be between about 3 mm and about 17 mm, and a collapsed (i.e., "built-in") lordotic angle α1 of the implant 10 can be between 0 degrees and about 15 degrees. When the implant 10 is in the expanded configuration E (FIG. 3), an expanded anterior height HA2 can be between about 8 mm and about 24 mm, the expanded posterior height HP2 can be between about 7 mm and about 21 mm, and the expanded lordotic angle α2 can be between about 15 degrees and about 45 degrees. It is to be appreciated that, in some embodiments, the implant 10 can be configured such that the expanded anterior height HA2 can be greater than the collapsed anterior height HA' by a factor of about 3, and the expanded posterior height HP2 can also be greater than the collapsed posterior height HP1 by a factor of about 3.

The superior and inferior plates 100, 200 can each define features configured to house components of the expansion mechanism 300. For example, as shown in FIGS. 2 and 3, the superior plate body 102 can define a first lumen 108 and a second lumen 110 spaced from the first lumen 108 in the distal direction. Accordingly, the first lumen 108 may be termed a "proximal" lumen and the second lumen 210 may be termed a "distal" lumen. Additionally, while not visible in FIG. 2 or 3, the inferior plate body 202 can define a third lumen 208 and a fourth lumen 210 spaced from the third lumen 208 in the distal direction. Similarly, the third lumen 208 may be termed a "proximal" lumen and the fourth lumen 210 may be termed a "distal" lumen. The first and second lumens 108, 110 of the superior plate 100 can be respectively aligned with and opposite the third and fourth lumens 208, 210 of the inferior plate 200 along the vertical direction V. Each of the lumens 108, 110, 208, 210 can extend from a first or anterior lumen side 108a to a second or posterior lumen side 108b spaced from the first side 108a along the transverse direction T. The implant 10 is configured such that when the implant 10 is in the collapsed configuration C, various portions of the expansion mechanism 300 can be at least partially disposed within the lumens 108, 110, 208, 210, 210, as described in more detail below. For reference, the third and fourth lumens 208, 210 of the inferior plate 200 are both visible in FIGS. 5 and 6B, the third lumen 208 is also visible in FIGS. 21 and 22, and the fourth lumen 210 is also visible in FIG. 9.

With reference to FIG. 4, the implant 10 can define an implant length L0 between about 25 mm and about 70 mm, measured from the trailing end 12 to the leading end 14 of the implant 10 along the longitudinal direction L. The implant can also define an implant width W0 between about 20 mm and about 50 mm, measured from the anterior side 16 to the posterior side 18 of the implant 10 along the transverse direction T. The implant 10 can also define a central aperture 111 extending through the implant 10 (i.e., from the first to the second bone bone-contacting surface 104, 204) along the vertical direction V. With respect to the longitudinal direction L, the central aperture 111 can be located between the first and second lumens 108, 110 of the superior plate 100 and between the third and fourth lumens 208, 210 of the inferior plate 200. The central aperture 111 can define a first or anterior side 111a and a second or posterior side 111b spaced from the anterior side along the transverse direction T. The central aperture 111 can further define a third or proximal side 111c and a fourth or distal side 111d spaced from the proximal side along the longitudinal direction L. The central aperture 111 can extend substantially entirely un-occluded through the implant 10 along the vertical direction V. The central aperture 111 can occupy a significant volume of the implant 10 and can be pre-filled or packed with bone growth material prior to insertion of the implant 10 so as to enhance subsequent bone fusion between the superior and inferior vertebral bodies 2, 4.

Figure 6A:
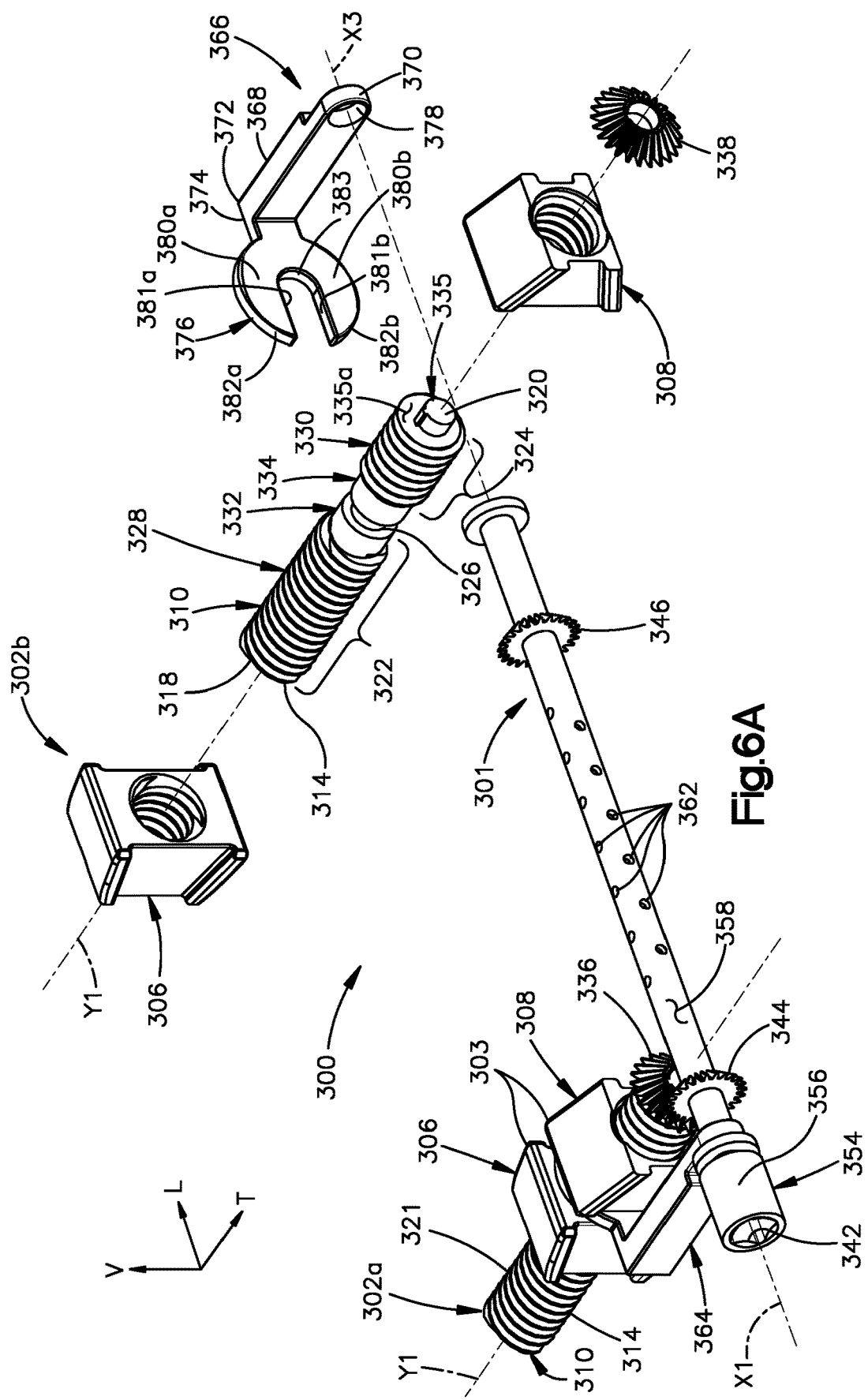
FIG. 6A is an exploded perspective view of the expansion mechanism shown in FIG. 5.

Referring now to FIGS. 5 and 6A, the expansion mechanism 300 can include a drive assembly 301 and one or more actuation assemblies, such as first and second actuation assemblies 302a, 302b, that are configured to be driven by the drive assembly 301 and actuate movement of at least one of the superior and inferior plates 100, 200 with respect to the other of the plates 100, 200 along the vertical direction V. The second actuation assembly 302b can be spaced from the first actuation assembly 302a in the distal direction. Thus, the first actuation assembly 302a can be termed a "proximal" actuation assembly and the second actuation assembly 302b can be termed a "distal" actuation assembly. The first actuation assembly 302a can include a first or proximal pair of wedge members 303 and the second actuation assembly 302b can include a second or distal pair of wedge members 304. Each pair of wedge members 303, 304 can include a first wedge member 306 and a second wedge member 308 spaced from each other along the transverse direction T. The first wedge member 306 may be located adjacent the anterior side 16 and remote from the posterior side 18 of the implant 10. The second wedge member 308 can be located adjacent the posterior side 18 and remote from the anterior side 16 of the implant 10. Thus, the first wedge member 306 of each pair may be termed an "anterior" wedge member and the second wedge member 308 of each pair may be termed a "posterior" wedge member. The first and second wedge members 306, 308 of each pair 303, 304 can be configured to translate relative to one another in the transverse direction T. In other embodiments, only one of the wedge members 306, 308 of each pair need translate relative to the other wedge member along the transverse direction T.

The first and second pairs 303, 304 of wedge members can be configured such that translation of the first wedge members 306 relative to the second wedge members 308 along the transverse direction T drives expansion of the superior and inferior plates 100, 200 away from each other in the vertical direction V. In this manner, the implant 10 can be actuated from the collapsed configuration C into the expanded configuration E. For illustrative purposes, FIG. 5 illustrates the wedge members 306, 308 of each pair in a separated configuration, while the proximal pair 303 of wedge members of FIG. 6A are shown in a contracted configuration. The superior and inferior plates 100, 200 and the first and second wedge members 306, 308 of each pair 303, 304 can be respectively shaped, oriented and otherwise configured such that the contracted configuration of the wedge members 306, 308 corresponds to the collapsed configuration C of the implant 10 and the separated configuration of the wedge members 306, 308 corresponds to the expanded configuration E of the implant 10. However, it is to be appreciated that, in other embodiments, the separated configuration of the wedge members 306, 308 can correspond to the collapsed configuration of the implant 10 and the contracted configuration of the wedge members 306, 308 can correspond to the expanded configuration of the implant 10.

With continued reference to FIGS. 5 and 6A, the first actuation assembly 302a can include a first or proximal actuation member 310 coupled to the first pair of wedge members 303 and the second actuation assembly 302b can include a second or distal actuation member 312 coupled to the second pair of wedge members 304. The first and second actuation members 310, 312 can be configured similarly or even substantially identically to one another. Thus, it is to be appreciated that the following description and reference numbers set forth below in reference to the first actuation member 310 can also be used with reference to the second actuation member 312.

Each actuation member 310 can include an actuation rod 314 defining a central rod axis Y1 extending along the transverse direction T and a first end 318 spaced from an opposed second end 320 along the central rod axis Y1. The actuation rod 314 can further define an outer surface 321 extending between the first and second ends 318, 320. Each actuation rod 314 can further define a first portion 322 extending from the first end 318 toward the second end 320 and a second portion 324 extending from the second end 320 toward the first end 318. The first and second portions 322, 324 can be separated and spaced from one another along the transverse direction T. The first end 318 and the first portion 322 can each be located adjacent the anterior side 16 and remote from the posterior side 18 of the implant 10. The second end 320 and the second portion 324 can each be located adjacent the posterior side 18 and remote from the anterior side 16 of the implant 10. Thus, the first end 318, the first portion 322, or any component associated therewith, may be termed a respective "anterior" end, portion, or component, and the second end 320, the second portion 324, or any component associated therewith, may be termed a "posterior" end, portion, or component. The actuation rod 310 can further define a retention feature, such as an annular recess 326 formed in the outer surface 321 of the rod 310, located between and separating the first and second portions 322, 324 along the transverse direction T. The first portion 322 can define a first or anterior threaded region 328 and the second portion 324 can define a second or posterior threaded region 330. The first portion 322 can also optionally define a first unthreaded region 332 interposed between the first threaded region 328 and the retaining feature 326 along the transverse direction T. The second portion 324 can also optionally define a second unthreaded 334 region interposed between the retaining feature 326 and the second threaded region 330 along the transverse direction T, and a third unthreaded region 335 extending from the second threaded region 330 to the second end 320 of the actuation rod 314 in the posterior direction. The actuation rod 314 can also define an abutment surface 335a interposed between the second threaded region 330 and the third unthreaded region 335 along the transverse direction T. The abutment surface 335a can face in the posterior direction. The first wedge member 306 of each pair 303, 304 can be configured to translate along the first threaded region 328 of the associated actuation rod 314 and the second wedge member 308 of each pair 303, 304 can be configured to translate along the second threaded region 330 of the rod 314 responsive to rotation of the rod 314 about central rod axis Y1, as described in more detail below.

The first actuation assembly 302a can include a first transmission member, such as a first gear 336, for converting at least a portion of a driving force, as applied by a driving tool operated by a physician, into a first rotational force of the first actuation member 310 about the central rod axis Y1 thereof. Similarly, the second actuation assembly 302b can include a second transmission member, such as a second gear 338, for converting an additional portion of the driving force into a second rotational force of the second actuation member 312 about the central rod axis Y1 thereof. For example, as shown, the first and second gears 336, 338 can be bevel gears positioned adjacent the posterior ends 320 of the actuation rods 314. However, other gear types, including worm gears and helical gear, by way of non-limiting example, are within the scope of the present embodiments.

The drive assembly 301 can include a drive member, such as a drive shaft 340, rotationally coupled to each of the first and second actuation members 310, 312. The drive shaft 340 can include an engagement feature, such as a socket 342, for receiving a driving tool operated by the physician. The drive shaft 340 can further include a third transmission member, such as a third gear 344, and a fourth transmission member, such as a fourth gear 346, for transmitting the drive force to the respective first and second transmission members 336, 338 of the actuation assemblies 302a, 302b. The third and fourth gears 344, 346 can be coupled to the drive shaft 340 by welding, brazing, mechanical fasteners, or any other technique. In other embodiments, either or both of the third and fourth gears 344, 346 can be formed monolithically with the drive shaft 340.

As shown, the drive shaft 340 can define a central shaft axis X2, a shaft proximal end 350, and a shaft distal end 352 spaced from the shaft proximal end 350 along the longitudinal direction L along the central shaft axis X2. The third and fourth gears 344, 346 can comprise bevel gears that are configured to mesh with the respective first and second gears 336, 338. The fourth gear 346 can be spaced from the third gear 344 in the distal direction; accordingly, the third gear 344 can be termed a "proximal" gear and the fourth gear 346 can be termed a "distal" gear. When the gears 344, 346 are bevel gears, as shown, the first and third gears 336, 344 may be oriented at 90 degrees relative to each other, and the second and fourth gears 338, 346 may be oriented at 90 degrees relative to each other, although other relative orientations are within the scope of the disclosed embodiments.

The socket 342 can be recessed into the drive shaft 340 from the shaft proximal end 350. The socket 342 can be defined by a head 354 of the drive shaft 340 that extends from the shaft proximal end 350 in the distal direction. The socket 342 can be any one of hexagonal, pentagonal, square, triangular, cross-shaped, plus sign-shaped, linear, star-shaped, or any other shape configured to engage a driving tool. The head 354 of the drive shaft 340 can define a first outer shaft surface 356 and a portion of the shaft located distally of the head 354 can define a second shaft outer surface 358 such that the first outer shaft surface 356 has a diameter greater than a diameter of the second outer shaft surface 358.

The drive shaft 340 can further define a central bore 360 in fluid communication with the socket 342, and a plurality of apertures 362 in fluid communication with the central bore 360. The plurality of apertures 362 can extend from the second outer surface 358 radially inward (i.e., in a radial direction that is perpendicular to the central shaft axis X2) to the central bore 360, such that the socket 342, the central bore 360, and the apertures 362 define a continuous fluid pathway. The plurality of apertures 362 can be positioned adjacent the central aperture 111 of the implant 10 such that additional bone growth material can be injected into the socket 342 (optionally with the use of a funnel), through the central bore 360 and out the plurality of apertures of the drive shaft 340 and into the central aperture 111 of the implant 10, particularly when the implant is in the expanded configuration E.

Once the implant 10 is inserted into the intervertebral space 5 as desired, the physician can actuate the implant 10 from the collapsed configuration C to the expanded configuration E by inserting the driving tool into the socket 342 of the drive shaft 340 and rotating the driving tool. Rotating the driving tool can rotate the drive shaft 340 and the third and fourth gears 344, 346 which, in turn, rotate the first and second gears 336, 338 and the actuation rods 314 coupled thereto. As the actuation rods 314 rotate, the first wedge members 306 and the second wedge members 308 of each pair 303, 304 translate away from each other along the respective first and second threaded regions 328, 330 of the actuation rods 310, 312 along the transverse direction T, forcing the superior and inferior plates 100, 200 to separate from one another in the vertical direction V. With the implant 10 in the expanded configuration E, the physician can inject additional bone growth material into the central aperture 111 in the manner described above.

The expansion mechanism 300 can include a first mounting element, such as a first or proximal bracket 364, and a second mounting element, such as a second or distal bracket 366, for coupling the drive shaft 340 to the first and second actuation members 310, 312, respectively. For example, the first and second brackets 364, 366 can each be a square (i.e., "right-angle") bracket in relation to the horizontal plane. In particular, each bracket 364, 366 can define a first bracket portion 368 configured to extend from a posterior bracket end 370 to a bend 372 spaced from the posterior bracket end 370 in the anterior direction. Each bracket 364, 366 can further define a second bracket portion 374 extending from the bend 372 to a holding element 376 spaced from the bend 372 in the longitudinal direction L. As shown more clearly in FIG. 6A, the first bracket portion 368 can define a bore coupling 378 adjacent the posterior bracket end 370 and sized and configured received the second outer surface 358 of the drive shaft 340. The bore coupling 378 can define a central coupling axis X3 that is configured to be coextensive with the central shaft axis X2 when the bracket 364, 366 is coupled to drive shaft 340. Each bore coupling 378 can be positioned adjacent an associated abutment flange of the drive shaft 340.

The holding element 376 of each bracket 364, 366 can be configured to engage the retention feature 326 of the associated actuation member 310, 312 in a manner at least partially retaining the actuation member 310, 312 in position relative to the drive shaft 340. The holding element 376 can define a pair of opposed arms 380a, 380b extending in the longitudinal direction L and spaced from one another in the vertical direction V so that inner surfaces 381a, 381b of the arms 380a, 380b can extend within the annular recess 326 of the associated actuation member 310, 312. The inner arm surfaces 381a, 381b can each be substantially linear and parallel with the longitudinal direction L. The arms 380a, 380b can further define outer arm surfaces 382a, 382b that are curved and convex so as to collectively define a C-shape in a vertical-longitudinal plane. The holding element 376 can further define a curved and concave intermediate surface 383 joining the inner arm surfaces 381a, 381b in the vertical direction V. The intermediate surface 383 can be contoured to match the contour of the outer surface 321 of the associated actuation rod 314 within the annular recess 326. When the brackets 364, 366 are coupled to their associated actuation members 310, 312, the inner arm surfaces 381a, 381b and the intermediate surface 383 of each holding element 376 can lightly abut or be in close proximity to the outer surface 321 of the associated actuation rod 314 within the annular recess 326 so as to substantially retain the actuation rod 314 in position relative to the drive shaft 340 in the transverse direction T, the vertical direction V, and at least one of the medial and lateral longitudinal directions. Stated differently, the holding element 376 of each bracket 364, 366 can be configured to act substantially as an axial bearing and at least partially as a journal bearing for the associated actuation rod 314.

As depicted, the proximal and distal brackets 364, 366 can be positioned on the drive shaft 340 such that first and second actuation members 310, 312 are positioned between the respective first bracket portions 368 with respect to the longitudinal direction L. In such embodiments, the arms 380a, 380b of the holding element 376 of the proximal bracket 364 can be open in the distal direction and the arms 380a, 380b of the holding element 376 of the distal bracket 366 can be open in the proximal direction. Thus, the arms 380a, 380b of each holding element 376 can be received on opposite vertical sides of the outer surface 321 of the rod 314 within the recess 326 during assembly of the implant 10. Alternatively, the proximal and distal brackets 364, 366 can be positioned on the drive shaft 340 such that respective first bracket portions 368 are positioned between the respective actuation members 310, 312 with respect to the longitudinal direction L. In such embodiments, the arms 380a, 380b of the proximal bracket 364 can be open in the proximal direction and the arms 380a, 380b of the distal bracket 366 can be open in the distal direction.

Figure 6B:
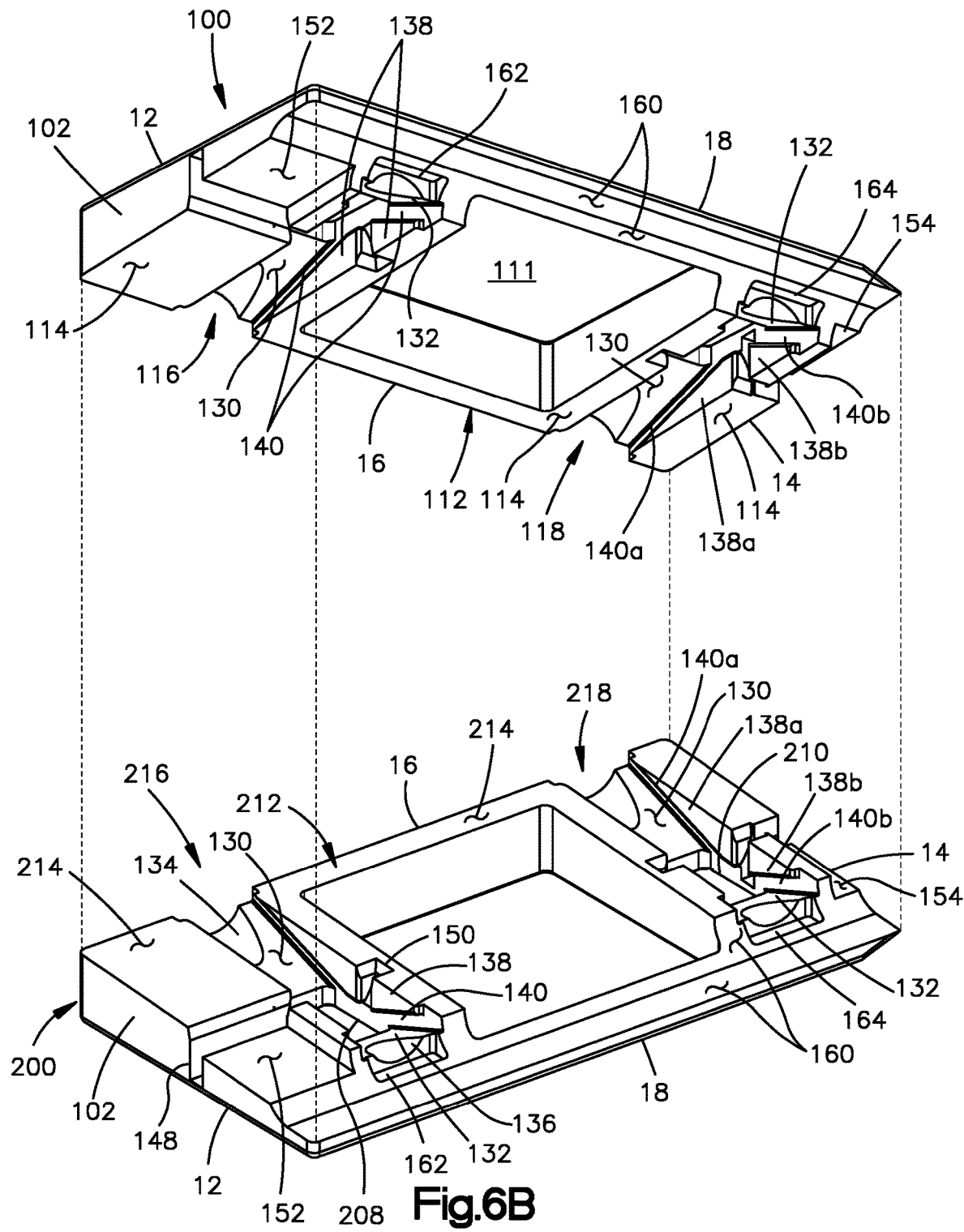
FIG. 6B is perspective views of upper and lower plates of the implant shown in FIG. 1, wherein the upper and lower plates are shown at different perspectives to illustrate interior surfaces of the plates.
Figure 11:
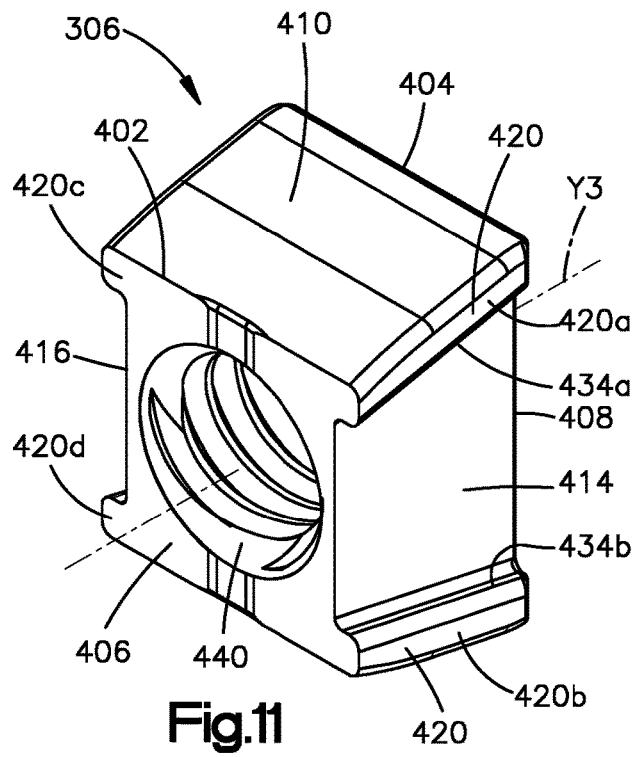
FIG. 11 is a perspective view of a wedge member of the expansion mechanism shown in FIGS. 5 and 6A.

Referring now to FIG. 6B, the superior plate body 102 can define a first interior face 112 spaced from and located opposite the first bone-contacting surface 104 along the vertical direction V, and the inferior plate body 202 can define a second interior face 212 spaced from and located opposite the second bone-contacting surface 204 along the vertical direction V. The first and second interior faces 112, 212 can be located opposite one another and can substantially face one another along the vertical direction V. The first and second interior faces 112, 212 can each extend from the trailing end 12 to the leading end 14 of the implant 10 and from the anterior side 16 to the posterior side 18 of the implant 10. The first and second interior faces 112, 212 can each be configured to couple with the wedge members 306, 308, as set forth in more detail below.

The first interior face 112 can define a first interior plate contact surface 114 and the second interior 212 face can define a second interior plate contact surface 214. The first and second interior plate contact surfaces 114, 214 can be configured to abut one another when the implant 10 is in the collapsed configuration C. Each of the first and second interior plate contact surfaces 114, 214 can include a plurality of contact surfaces that are separated from one another along the longitudinal and transverse directions L, T.

The first interior face 112 of the superior plate body 102 can define a first cavity 116 and a second cavity 118 spaced from the first cavity 116 in the distal direction. Thus, the first cavity 116 can be termed a "proximal" cavity and the second cavity 118 can be termed a "distal" cavity. The first and second cavities 116, 118 can each extend along the vertical direction V from the first interior plate contact surface 114 toward the first bone-contacting surface 104, and can each extend along the transverse direction T from a location adjacent, or contiguous with, the anterior side 16 of the implant 10 to a location adjacent the posterior side 18 of the implant 10. The first cavity 116 can be contiguous with the first lumen 108 and the second cavity 118 can be contiguous with the second lumen 110. The second interior face 212 of the inferior plate body 202 can define a third cavity 216 and a fourth cavity 218 spaced from the third cavity 216 in the distal direction. Thus, the third cavity 216 can be termed a "proximal" cavity and the fourth cavity 218 can be termed a "distal" cavity. The third and fourth cavities 216, 218 can each extend along the vertical direction V from the second interior plate contact surface 214 toward the second bone-contacting surface 204, and can each extend along the transverse direction T from a location adjacent, or contiguous with, the anterior side 16 of the implant 10 to a location adjacent the posterior side 18 of the implant 10. The third cavity 216 can be contiguous with the third lumen 208 and the fourth cavity 218 can be contiguous with the fourth lumen 210.

The first and third cavities 116, 216 can be opposed to one another and face one another along the vertical direction V so that the first and third cavities 116, 216 can collectively house the first pair of wedge members 303, the first actuation member 310, and at least a portion of the first bracket 364 at least when the implant 10 is in the collapsed configuration C. Similarly, the second and fourth cavities 118, 218 can be opposed and facing one another along the vertical direction V so as to collectively house the second pair of wedge members 304, the second actuation member 312, and at least a portion of the second bracket 366 at least when the implant 10 is in the collapsed position C.

With reference to FIGS. 6B and 7, the first and second cavities 116, 118 of the superior plate body 102 can be similarly shaped. The first and second cavities 116, 118 can be configured similarly or even substantially identically to one another. Furthermore, the third and fourth cavities 216, 218 can be configured within the inferior plate body 202 in a manner similar or substantially identical to the manner in which the first and second cavities 116, 118 are configured within the superior plate body 102. Thus, it is to be appreciated that the following description and reference numbers set forth below in reference to the first cavity 116 can also be used with respect to any one of the second, third, and fourth cavities 118, 216, 218.

With reference to FIG. 7, each cavity 116, 118 can extend from a first or anterior cavity end 120 to a second or posterior cavity end 122 along a central cavity axis Y2 that extends along the transverse direction T. The anterior cavity end 120 can be contiguous with the anterior side 16 of the implant 10, and the posterior cavity end 122 can be located adjacent the posterior side 18 of the implant 10. Each cavity 116, 118 can also define a first or external side 124 and an opposed second or internal side 126 spaced from the first side along the longitudinal direction L. The first and second sides of each cavity 116 can face one another along the longitudinal direction L.

Each of the superior and inferior plates 100, 200 can include one or more engagement elements configured to engage corresponding engagement elements of the expansion mechanism 300 in a manner allowing the expansion mechanism 300 to separate the plates 100, 200 along the vertical direction V. For example, within each of the cavities 116, the plate body 102 can define engagement elements, such as a pair of ramp surfaces that are configured to mate with and slide along portions of the first and second wedge members 306, 308. The pair of ramp surfaces can include a first or anterior ramp surface 130 and a second or posterior ramp surface 132 spaced from the first ramp surface 130 along the transverse direction T. The first and second ramp surfaces 130, 132 can be positioned, with respect to the transverse direction T, on the opposite sides 108a, 108b of the lumen 108, 110 that is in communication with the cavity 116. The first ramp surface 130 can extend from the anterior cavity end 120 to the anterior side 108a of the lumen, and the second ramp surface 132 can extend from the posterior side 108b of the lumen to the posterior cavity end 122.

The first ramp surface 130 is inclined to abut and slidingly receive a portion of the first wedge member 306, and the second ramp surface 132 is inclined to abut and slidingly receive a portion of the second wedge member 308. The first ramp surface 130 can be inclined such that a vertical distance, measured from the interior plate contact surface 114 of the associated plate body 102 to the first ramp surface 130, increases from the anterior ramp end to the posterior ramp end along the transverse direction T. The second ramp surface 132 can be inclined such that a vertical distance, measured from the interior plate contact surface of the associated plate body to the second ramp surface 132, decreases from the anterior ramp end to the posterior ramp end along the transverse direction T. As shown in FIG. 8 with respect to the superior plate body 102, the first ramp surface 130 can be inclined at a first acute ramp angle $\beta S1$ between about 10 degrees and about 40 degrees with respect to the interior plate contact surface 114. The second ramp surface 132 can be inclined at a second acute ramp angle $\beta S2$ between about 10 degrees and about 60 degrees with respect to the interior plate contact surface 114. Similarly, as shown in FIG. 9 with respect to the inferior plate body 202, the first ramp surface 130 within the associated cavity 216 of the inferior plate body 202 can be inclined at a first acute ramp angle $\beta I1$ between about 10 degrees and about 40 degrees with respect to the interior plate contact surface 214. The second ramp surface 132 within the associated cavity 216 of the inferior plate body 202 can be inclined at a second acute ramp angles $\beta I2$ between about 10 degrees and about 60 degrees with respect to the interior plate contact surface 214. It is to be appreciated that the first and second ramp angles $\beta S1$, $\beta S2$ $\beta I1$, $\beta I2$ of the ramp surface 130, 132 within each cavity 116, 118, 216, 218 can vary as needed.

The plate body 102 can also define, within each cavity 116, 118, a first curvilinear portion 134 disposed at the anterior side 16 of the implant 10 and in communication with the first ramp surface 130, and a second curvilinear portion 136 disposed at the posterior end 122 of the cavity 116 and in communication with the second ramp surface 132. The first and second curvilinear portions 134, 136 can be recessed from the first and second ramp surface 130, 132, respectively, toward the bone-contacting surface 104 of the plate body 102 along the vertical direction V. The first and second curvilinear portions 134, 136 can each define a curvilinear profile in a vertical-longitudinal plane. When the superior and inferior plates 100, 200 are in the collapsed configuration C, the vertically opposed first curvilinear portions 134 of the superior and inferior plate bodies 102, 202 can collectively define a first or anterior access opening for the first portion 322 of the associated actuation member 310, 312, and the vertically opposed second curvilinear portions 136 of the plates bodies 102, 202 can collectively define a second or posterior access opening for the second portion 324 of the associated actuation member 310, 312.

At each of the external and internal sides 124, 126 of the cavity 116, the plate body 102 can define one or more projections 138 protruding inwardly toward the central cavity axis Y2 along the longitudinal direction L. The projections 138 can at least partially define one or more channels 140 located vertically between the one or more projections 138 and the associated ramp surface 130, 132 within the cavity 116. The projections 138 and channels 140 can be defined by various surfaces within the cavity 116. For example, as shown in FIG. 10, at each of the external and internal sides 124, 126 of the cavity 116, the plate body 102 can define a first surface 142 and a second surface 144 each extending in the vertical and transverse directions V, T. The first surface can be contiguous with the interior contact surface 114 of the plate body 102. The second surface 144 can be contiguous with one or more of the first and second ramp surface 130, 132 within the cavity 116, and can be located between the first surface 142 and the associated ramp surface 130, 132 with respect to the vertical direction V. With respect to the longitudinal direction L, the first surface 142 can be located between the second surface 144 and the central cavity axis Y2. The plate body 102 can define a third or overhang surface 146 extending between the first and second surfaces 142, 144 in the longitudinal direction L. The overhang surface 146 can be contiguous with one or both of the first and second surfaces 142, 144. The first and second surfaces 142, 144 can be substantially parallel with one another. The overhang surface 146 can be substantially orthogonal with respect to one or both of the first and second surfaces 142, 144. The one or more projections 138 can be at least partially defined by the overhang surface 146 and the first surface 142. Similarly, the one or more channels 140 can be at least partially defined by the second surface 144 and the overhang surface 146. Thus, the one or more projections 130 can overlap at least portions of the first and second ramp surface 130, 132 in the longitudinal direction L.

On each side of the cavity 116, the one or more protrusions 138 can include a first or anterior protrusion 138a that partially overlaps the first 146 ramp surface 130 in the longitudinal direction L and a second or posterior protrusion 138b that partially overlaps the second ramp surface 132 in the longitudinal direction L. Additionally, the one or more channels 140 can include a first or anterior channel 140a positioned vertically between the first protrusion 138a and the first ramp surface 130, and a second or posterior channel 140b positioned vertically between the second protrusion 138b and the second ramp surface 132. In this manner, the first and second channels 140a, 140b may be characterized as being positioned "underneath" the first and second protrusions 138a, 138b, respectively. The first channel 140a can be inclined so as to be parallel with the first ramp surface 130, and the second channel 140b can be inclined so as to be parallel with the second ramp surface 132. Thus, as shown in FIGS. 8 and 9, the first channels 140a within the associated cavities 116, 118, 216, 218 of the superior and inferior plate bodies 102, 202 can each be inclined at a first acute channel angle δS1, δI1 between about 10 degrees and about 40 degrees with respect to their interior plate contact surface 114, 214, and the second channels 140b can each be inclined at a second acute channel angle δS2, δI2 between about 10 degrees and about 60 degrees with respect to their interior plate contact surface 114, 214.

It is to be appreciated that the protrusions 138 and channels 140 on the interior side 126 of the cavity 116 can be sized, shaped and oriented similarly to those on the exterior 124 side of the cavity 116. Stated differently, the features on the external and internal sides 124, 126 of the cavity 116 can virtually be mirror images of each other about a vertical plane that extends along the central cavity axis Y2.

In association with each cavity 116, 118, the plate body 102 can also define a first or external longitudinal slot 148 and a second or internal longitudinal slot 150 aligned with each other on the opposite sides 124, 126 of the cavity. The first slot 148 can extend from the exterior of the plate body 102 to the cavity along the longitudinal direction L, and the second slot 150 can extend from the cavity toward the interior of the plate body 102 along the longitudinal direction L. The anterior and posterior protrusions 138a, 138b on the exterior side 124 of each cavity 116 can be separated from one another along the transverse direction T by the first slot 148, and the anterior and posterior protrusions 138a, 138b on the interior side 126 of each cavity 116 can be separated from one another along the transverse direction T by the second slot 150. Additionally, the anterior and posterior channels 140a, 140b on each side 124, 126 of each cavity 116 can also be located on opposite sides of the respective slots 148, 150 with respect to the transverse direction T.

The plate body can also define a first or proximal landing surface 152 associated with the first cavity 116, and a second or distal landing surface 154 associated with the second cavity 118. The first and second landing surfaces 152, 154 can each be recessed into the plate body 102 from the interior plate contact surface 114 thereof in the vertical direction V. The second landing surface 154 can be spaced from the first landing surface 152 in the distal direction, such that the first and second cavities 116, 118 are both positioned between the first and second landing surfaces 152, 154 along the longitudinal direction L. The first landing surface 152 can be adjacent to and optionally contiguous with the trailing end 12 of the implant 10, and the second landing surface 154 can be adjacent to and optionally contiguous with the leading end 14 of the implant 10. The first and second landing surfaces 152, 154 can each be adjacent the posterior side 18 and remote from the anterior side 16 of the implant 10. The first and second landing surfaces 152, 154 can each extend in the posterior direction from the external slot 148 of the associated cavity 116, 118.

With respect to the longitudinal direction L, the first landing surface 152 can be separated from the external side 124 of the first cavity 116 by a first wall 156 defined by the plate body 102, and the second landing surface 154 can be separated from the external side 124 of the second cavity 118 by a second wall 158 defined by the plate body 102.

Each cavity 116, 118 and its associated first and second slots 148, 150 and associated landing surface 152, 154 is configured to receive the associated bracket 364, 366. For example, with respect to the first cavity 116, the first portion 368 of the first bracket 364 can extend across the first landing surface 152 in the transverse direction T, and the second portion 374 of the bracket 364 can extend along the longitudinal direction L across the first cavity 116 and within the external and internal slots 148, 150 associated therewith.

Similarly, the first portion 368 of the second bracket 366 can extend across the second landing surface 154 in the transverse direction T, and the second portion 374 of the bracket 366 can extend along the longitudinal direction L across the second cavity 118 and within the external and internal slots 148, 150 associated therewith. In this manner, the brackets 364, 366 can be at least partially retained in position relative to the associated plate body 102, as shown in FIG. 5, for example. The internal slots 150 can optionally each have a curved and concave profile in a vertical-longitudinal plane so as to correspond to the curved and convex profile of the outer arm surfaces 382a, 382b of the holding element 378 of the associated bracket 364, 366. The external and internal slots 148, 150 can each have a width in the transverse direction T that is greater than a transverse width of the second portions 374 of the brackets 364, 366 so that the brackets 364, 366 can adjust their position relative to the superior and inferior plate bodies 102, 202 along the transverse direction T during expansion of the implant 10 from the collapsed configuration C to the expanded configuration E.

The interior face 112 of the plate body 102 can also define a third landing surface 160 adjacent to and optionally contiguous with the posterior side 18 of the implant 10. The third landing surface 160 can extend from the proximal end 12 to the distal end 14 of the implant 10 along the longitudinal direction L, and can extend from the first and second cavities 116, 118 to the posterior side 18 of the implant 10 in the posterior direction. The third landing surface 160 can be contiguous with one or more of the first and second cavities 116, 118, the first and second landing surfaces 152, 154, and the first and second walls 156, 158 of the plate body 102. The third landing surface 160 can be configured to at least partially house the drive shaft 340 and the first and second transmission members 336, 338 of the expansion mechanism 300. Accordingly, the third landing surface 160 can be sloped so that a vertical distance measured from the third landing surface 160 to the bone-contacting surface 104 of the plate body 102 decreases along the posterior direction. A portion of the third landing surface 160 that is contiguous with the first and second cavities 116, 118 can define a curved and concave slope profile in the vertical-transverse plane. The interior face 112 of the plate body 102 can further define first and second recesses 162, 164 adjacent to, or optionally contiguous with, the posterior ends 122 of the first and second cavities 116, 118, respectively, so as to at least partially house the first and second transmission members 336, 338.

The inferior plate 200 can be configured similarly to the superior plate 100. For example, as shown in the illustrated embodiments, the superior and inferior plate bodies 102, 202 can be mirror images of each other about a horizontal plane extending through the geometric center of the implant 10. Accordingly, the inferior plate 200 can include structural features that correspond to those described above with respect to the superior plate 100. Thus, reference numbers of features of the superior plate body 102 can be used with reference to the corresponding features of the inferior plate body 202. For example, the third and fourth cavities 216, 218 defined by the inferior plate body 202 can be configured similarly to the first and second cavities 116, 118 of the superior plate body 102. Therefore, while certain features of the third and fourth cavities 216, 218 may not have been explicitly discussed herein, such as the posterior and anterior ramp surface 130, 132, protrusions 138 and channels 140, by way of non-limiting example, it is to be appreciated that such features of the third and fourth cavities 216, 218 can be configured substantially the same as those of the first and second cavities 116, 118, and the reference numbers of those features can be used interchangeably.

Referring now to FIGS. 11 through 14, various view of the first or anterior wedge member 306 are illustrated. The first wedge members 306 of each of the proximal and distal pairs 303, 304 can be configured similarly. The first wedge member 306 can define a first wedge body 400 extending along a first central wedge axis Y3 between an outer end 402 and an inner end 404 spaced from the outer end 402 with respect to the first central wedge axis Y3. The outer end 402 can define an outer face 406, and the inner 404 and can define an inner face 408, and each face 406, 408 can optionally be planar and oriented normal to the first central wedge axis Y3. The first central wedge axis Y3 is generally aligned with the central rod axis Y2 of the actuation rod 314 that carries the first wedge member 306. Thus, the first central wedge axis Y3 and the central rod axis Y2 can each extend along the transverse direction T. As show in FIGS. 5 and 6A, the outer end 402 of the first wedge body 400 is positioned to face in the anterior direction, and the inner end 404 is positioned to face in the posterior direction. The first wedge body 400 can define a first wedge length L1 between about 1.5 mm and about 10 mm measured from the outer end 402 to the inner end 404 of the first wedge body 400.

The first wedge body 400 can define one or more engagement elements configured to engage the corresponding engagement elements of the superior and inferior plates 100, 200 in a manner driving separation between the plates 100, 200 in the vertical direction V. The one or more engagement elements of the first wedge body 400 can include a first or superior inclined surface 410 and a second or inferior inclined surface 412 opposite and spaced from one another along the vertical direction V. The superior and inferior inclined surfaces 410, 412 can extend along the transverse direction T from the outer end 402 to the inner end 404 of the first wedge body 400. The superior and inferior inclined surfaces 410, 412 can each be inclined relative to the first central wedge axis Y3 such that the outer end is narrower than the inner end in the vertical direction V, thus providing the first wedge body 400 with its wedge shape. A height H1 of the outer end 402 of the first wedge body 400 in the vertical direction V can be in the range of about 2 mm and about 15 mm, and a height H2 of the inner end 404 of the first wedge body 400 in the vertical direction V can be in the range of about 3.5 mm and about 17.5 mm. The superior inclined surface 410 can slidably mate with the first ramp surface 130 within the associated cavity 116, 118 of the superior plate body 102, and the second inferior inclined surface 78 can slidably mate with the first ramp surface 130 within the associated cavity 216, 218 of the inferior plate body 202.

The first wedge body 400 can further define a first side surface 414 and an opposed second side surface 416 spaced from one another along the longitudinal direction L. The first and second side surfaces 414, 416 can extend from the outer end 402 to the inner end 404 of the first wedge body 400 along the transverse direction T and between the superior and inferior inclined surfaces 410, 412 along the vertical direction V. The first and second side surfaces 414, 416 can each be planar and parallel with one another, although other orientations are within the scope of the present disclosure.

The first wedge body 400 can also define one or more ridges 420 protruding from the first and second side surfaces 414, 416 along the longitudinal direction L. The ridges 420 are configured to interlock the first wedge member 306 with one or both of the superior and inferior plates 100, 200 so as to couple the superior and inferior plates 100, 200 together. For instance, the one or more ridges 420 are configured to be slidably received within one or more of the anterior channels 140a within the associated cavity 116. Accordingly, each of the ridges 420 of the first wedge body 400 can generally be parallel with the associated channels 140a in which they are received.

The one or more ridges 420 can include a first ridge 420a and a second ridge 420b protruding outwardly from the first side surface 414 of the first wedge body 400 along the longitudinal direction L, and can further include a third ridge 420c and a fourth ridge 420d protruding outwardly from the second side surface 416 of the first wedge body 400 along the longitudinal direction L. The first and third ridges 420a, 420 may each be located adjacent to or optionally contiguous with the superior inclined surface 410 of the first wedge body 400. Thus, the first and third ridges 420a, 420c may each be termed a superior ridge. The second and fourth ridges 420b, 420d may each be located adjacent to or optionally contiguous with the inferior inclined surface 412 of the first wedge body 400, and can thus each be termed an inferior ridge. One or both of the first and third ridges 420a, 420c can extend from the inner end 404 to the outer end 402 of the first wedge body 400 and can be parallel with the superior inclined surface 410 of the wedge body 400. Similarly, one or both of the second and fourth ridges 420b, 420d can extend from the inner end 404 to the outer end 402 of the first wedge body 400 and can be parallel with the inferior inclined surface 412 of the wedge body 400. However, in other embodiments, any one of the ridges 420 can extend less than the full distance between the outer and inner ends 402, 404 of the first wedge body 400.

Each of the ridges 420a, 420b, 420c, 420d can define a superior ridge surface 422, an opposed inferior ridge surface 424, and an outer ridge surface 426 extending between the superior and inferior ridge surfaces 422, 424 in the vertical direction V. The superior ridge surfaces 422 of the first and third ridges 420a, 420c can be adjacent to, contiguous with, or, as shown in the illustrated embodiments, can define a part of, the superior inclined surface 410 of the first wedge body 400. Similarly, the inferior ridge surfaces 424 of the second and fourth ridges 420b, 420d can be adjacent to, contiguous with, or, as shown, can define a part of, the inferior inclined surface 412 of the first wedge body 400. It is to be appreciated that the superior and inferior inclined surfaces 410, 412 of the first wedge body 400 can be planar, or, as depicted in FIGS. 6A and 11 through 14, can define one or more curved profiles in a vertical-transverse plane. For example, the superior and inferior inclined surfaces 410, 412 can each define a first region 428 adjacent or contiguous with the outer end 402, a second region 430 adjacent or contiguous with the inner end 404, and a third, intermediate region 432 located between the first and second regions 428, 430 with respect to the transverse direction T. As shown, the first and second regions 428, 430 can define first and second curved convex profiles, respectively, and the intermediate region 432 can define a linear profile, in the vertical-transverse plane. The curved profiles of the first and second regions 428, 430 can define the same radius of curvature or different radii of curvature, as needed. It is to be appreciated that the foregoing first, second and intermediate profiles can also be present on the superior ridge surfaces 422 of the first and third ridges 420a, 420c and the inferior ridges surfaces 424 of the second and fourth ridges 420b, 420d, particularly when the superior and inferior ridge surfaces 422, 424 define a part of the superior and inferior inclined surfaces 410, 412 of the first wedge body 400.

The curved profiles of the first and second regions 428, 430 of each of the superior and inferior inclined surfaces 410, 412 can reduce friction between the first wedge body 400 and the superior and inferior plate bodies 102, 202 during translation of the first wedge body 400 along the transverse direction T. The curved profiles can also provide for a smoother transition between the various lordotic angles α of the superior and inferior bone-contacting surfaces 104, 204, as well as reduce internal stresses imparted to the first wedge body 400 and the plate bodies 102, 202, respectively, during expansion of the implant 10.

Figure 13:
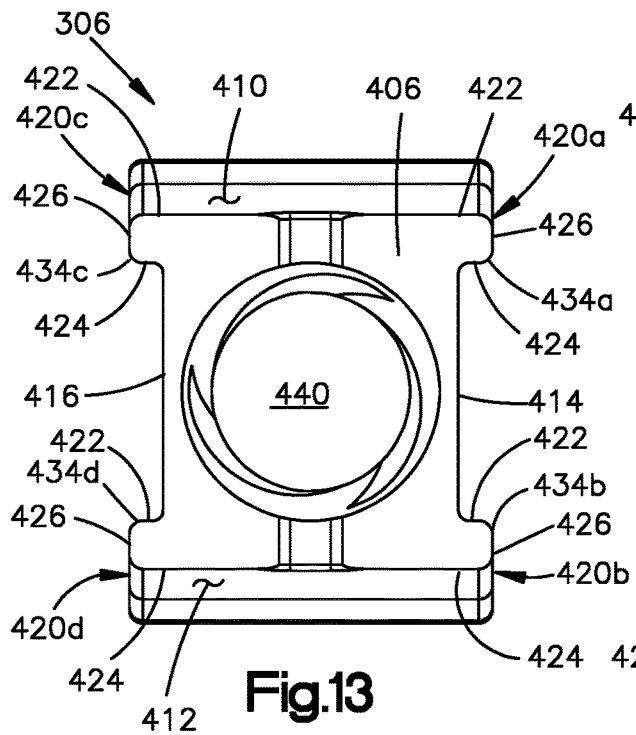
FIGS. 13 and 14 are opposing ends views of the wedge member shown in FIG. 11.
Figure 14:
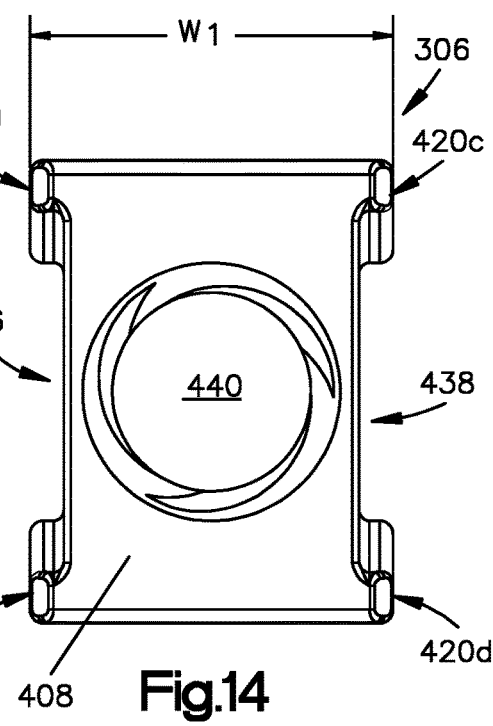
Figure 15:
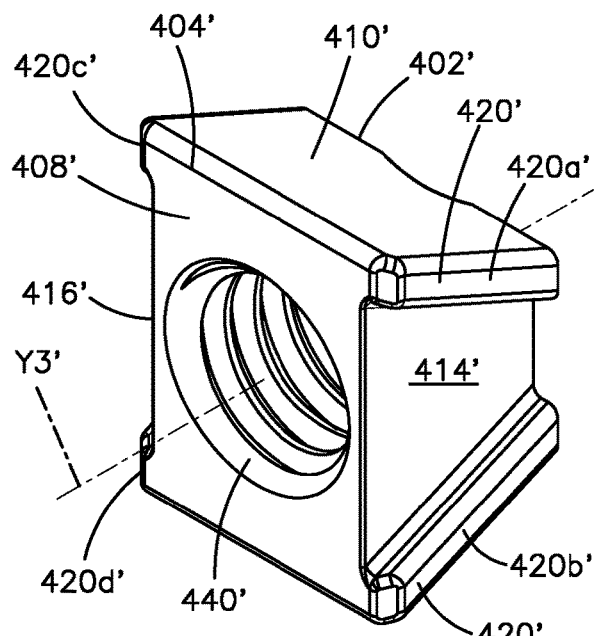
FIG. 15 is a perspective view of another wedge member of the expansion mechanism shown in FIGS. 5 and 6A.
Figure 16:
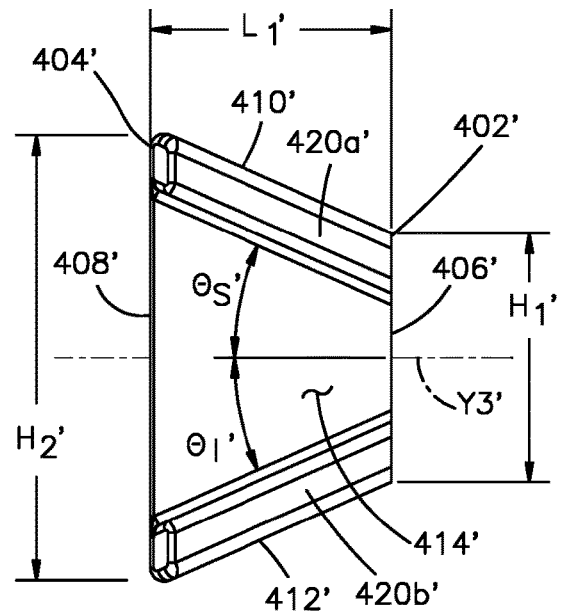
FIG. 16 is a side view of the wedge member shown in FIG. 15.
Figure 17:
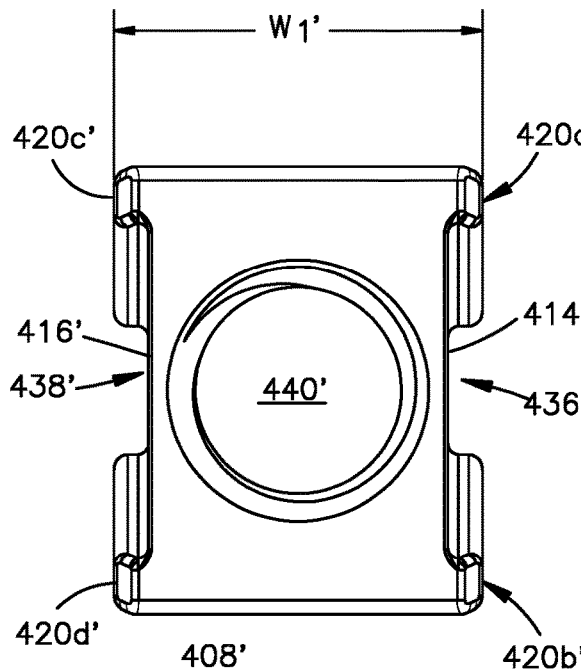
FIGS. 17 and 18 are opposing ends views of the wedge member shown in FIG. 15.
Figure 18:
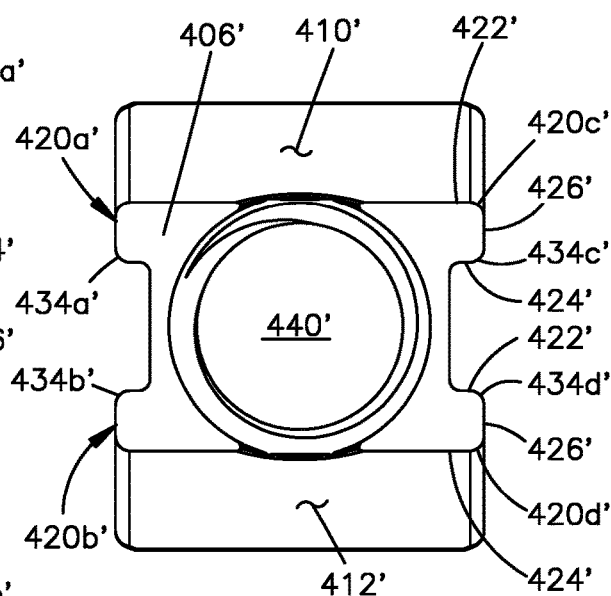

As best shown in FIGS. 13 and 14, the first wedge body 400 can define a first maximum wedge width W1 between about 4 mm and about 7 mm measured from the outer surfaces 426 of the first and third ridges 420a, 420c (or the second and fourth ridges 420b, 420d) along the longitudinal direction L. Additionally, the superior inclined surface 410 can define a linear profile in a vertical-longitudinal plane, optionally with respect to each location along the first central wedge axis Y3.

Figure 12:
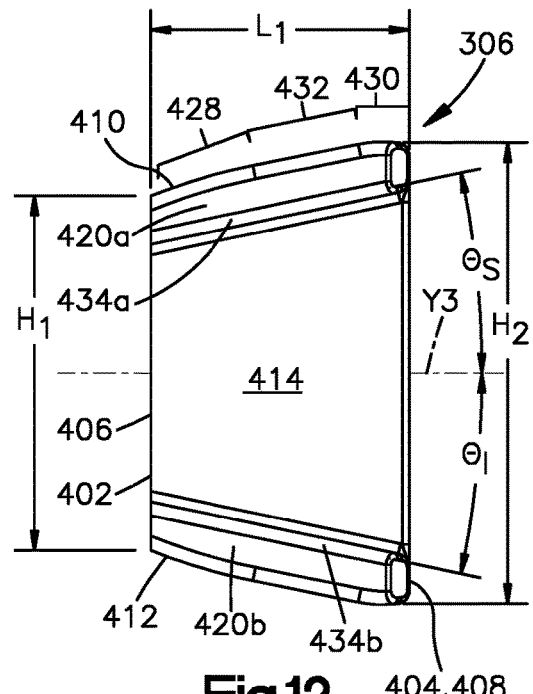
FIG. 12 is a side view of the wedge member shown in FIG. 11.

With particular reference to FIG. 12, a first edge 434a between the outer and inferior ridge surfaces 426, 424 of the first ridge 420a and a second edge 434b between the outer and superior surfaces 426, 422 of the second ridge 420b can each define a linear profile in a vertical-transverse plane. Similarly, respective third and fourth edges 434c, 434d between the outer and inferior ridge surfaces 426, 424 of the third ridge 420c and between the outer and superior surfaces 426, 422 of the fourth ridge 420d, respectively, can each define a linear profile in a vertical-transverse plane. Each of these edges 434a, 434b, 434c, 434d can extend parallel with the respective channel 140a in which it is received. It is to be appreciated that the first, second, third, and fourth edges 434a, 434b, 434c, 434d can be considered as defining the incline angles θ of the first, second, third, and fourth ridges 420a, 420b, 420c, 420d, respectively. This is so even considering that the superior surfaces 422 of the first and third ridges 420a, 420c and the inferior surfaces 424 of the second and fourth ridges 420b, 420d can each define one or more curved profiles in the vertical-transverse plane. Accordingly, the first and third edges 434a, 434c can be parallel with one another and with the anterior channels 140a on opposite sides of the associated cavity 116, 118 of the superior plate body 102, and can each be inclined at a first or superior ridge incline angle θS between about 10 and 40 degrees with respect to the first central wedge axis Y3 (or with respect to the central rod axis Y1 of the actuation member 310 on which the first wedge body 400 is received). Similarly, the second and fourth edges 434b, 434d can be parallel with one another and with the anterior channels 140a on opposite sides of the associated cavity 216, 218 of the inferior plate body 202, and can each be inclined at a second or inferior ridge incline angle θI between about 10 and 40 degrees with respect to the first central wedge axis Y3 (or with respect to the central rod axis Y1 of the actuation member 310 on which the first wedge body 400 is received). The first and second ridge incline angles θS, θI can vary as needed. It is to be appreciated that, while the superior and inferior inclined surfaces 410, 412 of the first wedge body 400 can define one or more curved profiles in a vertical-transverse plane, the general incline angles of the superior and inferior surfaces 410, 412 can be defined or at least approximated by the superior and inferior ridge incline angles θS, θI, respectively.

The inferior ridge surface 424 of the first ridge 420a and the superior ridge surface 422 of the second ridge 420b can each be adjacent to or contiguous with the first side surface 414 of the first wedge body 400, and the inferior ridge surface 424 of the third ridge 420c and the superior ridge surface 422 of the fourth ridge 420d can each be adjacent to or contiguous with the second side surface 416 of the first wedge body 400. The outer ridge surfaces 426 of the first and third ridges 420a, 420c can be opposite one another along the longitudinal direction L, and outer ridge surfaces 426 of the second and fourth ridges 420b, 420d can be opposite one another along the longitudinal direction L. The inferior ridge surface 424 of the first ridge 420a and the superior ridge surface 422 of the second ridge 420b can be opposite and facing one another with respect to the vertical direction V such that the first central wedge axis Y3 is positioned between the inferior ridge surface 424 of the first ridge 420a and the superior ridge surface 422 of the second ridge 420b with respect to the vertical direction V. Similarly, the inferior ridge surface 424 of the third ridge 420c and the superior ridge surface 422 of the fourth ridge 420d can be opposite and facing one another with respect to the vertical direction V such that the first central wedge axis Y3 is positioned between the inferior ridge surface 424 of the third ridge 420c and the superior ridge surface 422 of the fourth ridge 420d with respect to the vertical direction V.

The inferior ridge surface 424 of the first ridge 420a, the superior ridge surface 422 of the second ridge 420b, and the first side surface 424 can collectively define a first recess portion 436 of the first wedge body 400, which can receive the anterior protrusions 138a defined on the associated side 124, 126 of the associated cavities 116, 216 of the superior and inferior plate bodies 102, 202, respectively. Similarly, the inferior ridge surface 424 of the third ridge 420c, the superior ridge surface 422 of the fourth ridge 420d, and the second side surface 416 can collectively define a second recess portion 438 of the first wedge body 400 which can receive the anterior protrusions 138a defined on the associated opposite side 126, 124 of the associated cavities 116, 216 of the superior and inferior plate bodies 102, 202, respectively. Simultaneously, the first and third ridges 420a, 420c can be received within the anterior channels 140a of the superior plate body 102, and the second and fourth ridges 420b, 420d can be received within the anterior channels 140a of the inferior plate body 202. Accordingly, the protrusions 138 of the plate bodies 102, 202 can overlap with the associated ridges 420 in the longitudinal direction L. Stated differently, the overhang surface 146 of each protrusion 138 can extend between the edge 434 of the associated ridge 420 and the associated side surface 414, 416 of the first wedge body 400 in the longitudinal direction L in manner providing mechanical interference resisting separation between the first wedge body 400 and the superior and inferior plate bodies 102, 202 along the vertical direction V. In this manner, the ridges 420 can interlock the first wedge body 400 to each of the superior and inferior plates 100, 200 so as to couple the superior and inferior plates 100, 200 together.

The first wedge body 400 can also define a first bore 440 extending therethrough from the outer end 402 to the inner end 404 along the first central wedge axis Y3. The first bore 440 can be configured to receive at least a portion of the associated actuation member 310. For example, the first bore 440 can be internally threaded to mate with the first or anterior threaded region 328 of the actuation member 310.

Referring now to FIGS. 15 through 18, various view of the second or posterior wedge member 308 are illustrated. The second wedge members 308 of the proximal and distal pairs 303, 304 of wedge members can be configured similarly. Furthermore, it is also to be appreciated that the second wedge member 308 can be configured substantially similarly, or optionally virtually identically, to the first wedge member 306. Accordingly, it is to be appreciated that each of the features and reference numbers described above in relation to the first wedge member 306 can be replicated in relation to the second wedge member 308, indicated herein with a "prime" notation when used in reference to the second wedge member 308. Thus, the second wedge body 400' can define one or more engagement elements, such as the superior and inferior inclined surfaces 410', 412', that are configured to engage the corresponding engagement elements of the superior and inferior plates 100, 200 in a manner driving separation between the plates 100, 200 along the vertical direction V. For the sake of brevity, the following description of the second wedge body 400' will focus on the differences between the first and second wedge members 306, 308 of the illustrated embodiment.

The superior and inferior inclined surfaces 410', 412' of the second wedge body 400' can each define a linear profile in a vertical-transverse plane from the outer end 402' to the inner end 404'. The superior and inferior inclined surfaces 410', 412' of the second wedge body 400' can each be oriented at an incline angle $\theta S'$, $\theta I'$ between about 10 degrees and about 60 degrees from the second central wedge axis Y3' (or from the central rod axis Y1 of the actuation member 310 on which the second wedge body 400' is received) to the respective superior and inferior inclined surface 410', 412'. The second wedge body 400' can define a second wedge length L1' between about 1.5 mm and about 10 mm, a second maximum wedge width W1' between about 4 mm and about 7 mm, an outer end height H1' between about 2 mm and about 15 mm, and an inner end height H2' between about 3.5 mm and about 17.5 mm. The superior inclined surface 410' can slidably mate with the second or posterior ramp surface 132 within the associated cavity 116, 118 of the superior plate body 102, and the second inferior inclined surface 412' can slidably mate with the second or posterior ramp surface 132 within the associated cavity 216, 218 of the inferior plate body 202.

The one or more ridges 420' of the second wedge body 400' are configured to be slidably received within, and generally parallel with, the corresponding posterior channels 140b within the associated cavities 116, 118, 216, 218 of the superior and inferior plate bodies 102, 202. On the second wedge body 400', the superior inclined surface 410' can be parallel with each of the superior and inferior surfaces 422', 424' and the edges 434a', 434c' of the first and third (superior) ridges 420a', 420c, while the inferior inclined surface 412' can be parallel with each of the superior and inferior surfaces 422', 424' and the edges 434a', 434c' of the second and fourth (inferior) ridges 420b', 420d.

The first recess portion 436' of the second wedge body 400' can receive the posterior protrusions 138b defined on the associated side 124, 126 of the associated cavities 116, 118, 216, 218 of the superior and inferior plate bodies 102, 202, and the second recess portion 438' of the second wedge body 400' can receive the posterior protrusions 138b defined on the associated opposite side 126, 124 of the associated cavities 116, 118, 216, 218 of the superior and inferior plate bodies 102, 202, respectively. Simultaneously, the ridges 420' of the second wedge body 400' can be received within the posterior channels 140b of the associated cavity 116, 118, 216, 218. Thus, the protrusions 138 of the plate bodies 102, 202 can overlap in the longitudinal direction L with the associated ridges 420' of the second wedge body 400' so as to interlock the second wedge body 400' to each of the superior and inferior plates 100, 200. The second bore 440' defined by the second wedge body 400' can be internally threaded to mate with the second or posterior threaded region 330 of the associated actuation member 310. Further, one or both of the first and second wedge bodies 400, 400' can include a radiographic marker embedded therein (not shown).

Figure 19:
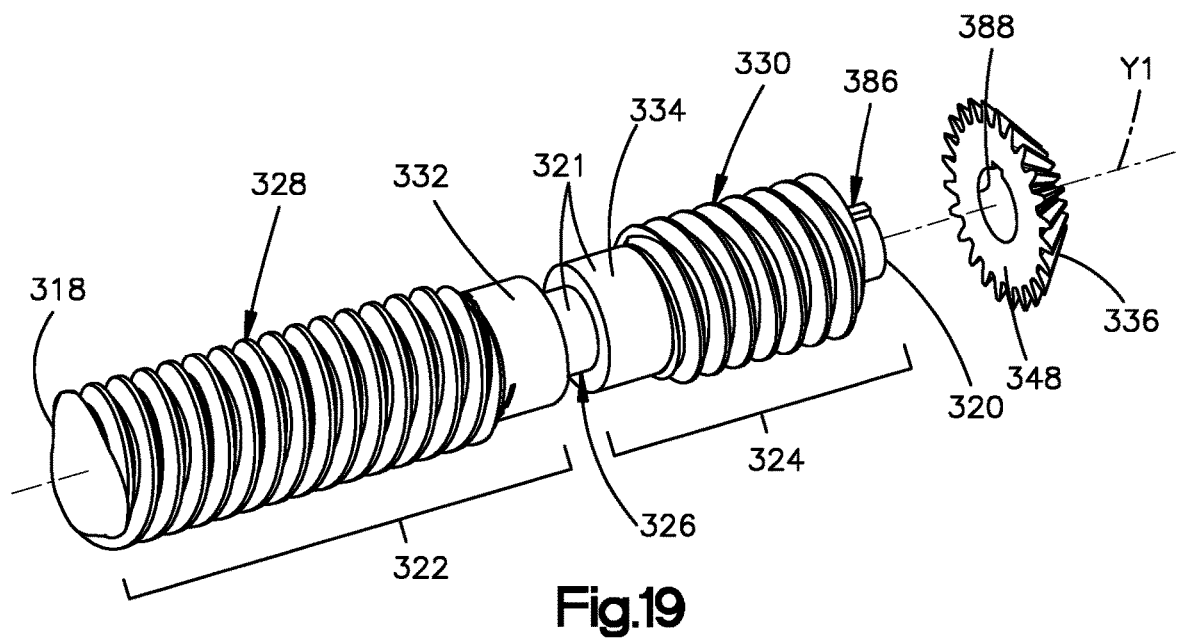
FIG. 19 is an exploded perspective view of an actuation member of the expansion mechanism shown in FIGS. 5 and 6A.
Figure 20:
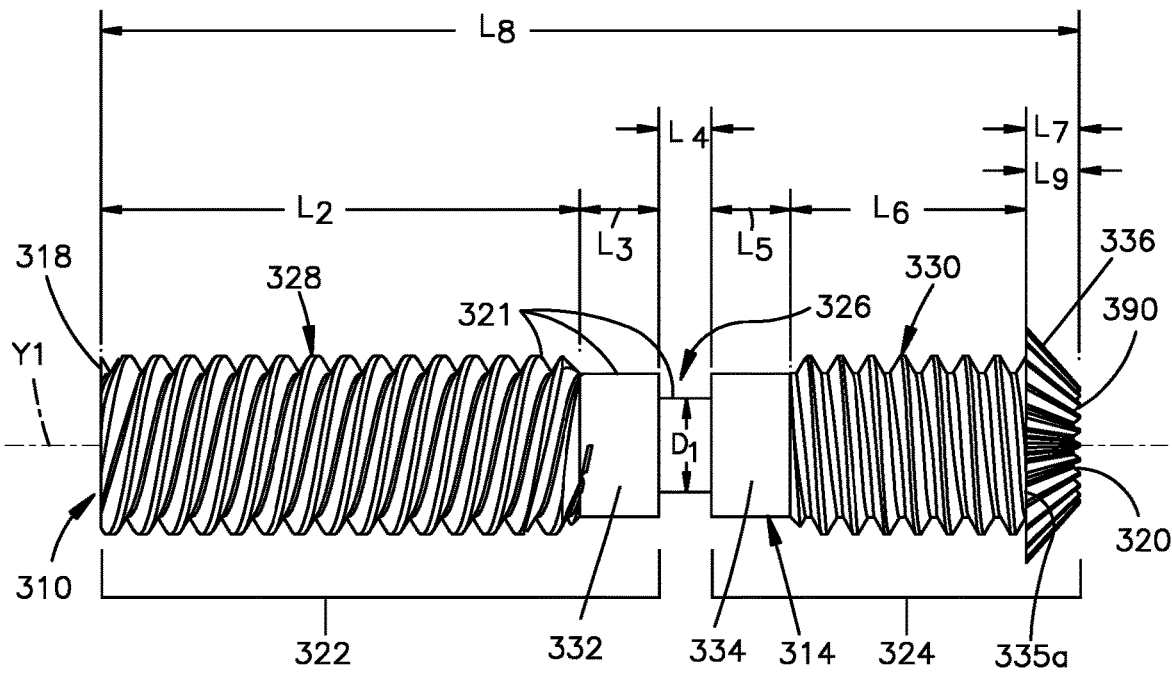
FIG. 20 is a side view of the actuation member shown in FIG. 19.

Referring now to FIGS. 19 and 20, the first and second (i.e., proximal and distal) actuation members 310, 312 are configured to couple the first and second wedge members 306, 308 of each pair 303, 304 together while also providing stability to the superior plate 100 and inferior plate 200 during expansion of the implant 10. The first and second actuation members 310, 312 can be configured substantially similarly, or even optionally virtually identically, to each other. Accordingly, while only the first actuation member 310 is shown in FIGS. 19 and 20, it is to be understood that the following description and reference numbers can also be used with reference to the second actuation member 312.

The first or anterior threaded region 328 can have a length L2 that is greater than a length L6 of the second or posterior threaded region 330 by a factor between about 1.5 to 4. The first or anterior unthreaded region 332 can have a length L3 that is less than the length L1 of the anterior wedge 306. Similarly, the second or posterior unthreaded region 334 can have a length L5 that is less than the length L1' of the second or posterior wedge 308. In some embodiments, the lengths L3, L5 of the first and second unthreaded regions 332, 334 can each be as small as zero. The annular recess 326 can have a length L4 of in the range of about 0.25 mm and about 2 mm. The third unthreaded region 335 can have a length L7 of at least about 3 mm. The actuation rod 314 can have a total length L8 of between about 18 mm and about 48 mm. Each of the foregoing lengths L2-L8 are measured along the central rod axis Y1. The outer surface 321 of the actuation rod 314 within the annular recess 326 can define a diameter D1 greater than about 1 mm.

The posterior threaded region 330 can be located adjacent to the associated first or second transmission member 336, 338. For example, in the illustrated embodiments, the posterior threaded region 330 can be contiguous with a rear face 384 of the associated bevel gear 336. Additionally, the third unthreaded region 335 of the actuation rod 310 can define a mounting formation, such as a keyed connector 386, that is configured to be matingly received within a central keyed slot 388 defined in the rear face 384 of the bevel gear 336. In this manner, to assemble at least the second or posterior wedge member 308 on the actuation rod 314, a technician can insert the second threaded region 330 into the second bore 440' of the second wedge member 308 and rotate the actuation rod 314 with respect to the second wedge member 308 until the second wedge member 308 translates along the second threaded portion 330 until the outer face 402' of the second wedge body 400' is positioned remote from, or at least spaced from, the abutment surface 335a in the anterior direction. Once the second wedge member 308 is so positioned on the actuation rod 314, the technician can insert the keyed connector 386 into the central keyed slot 388 of the bevel gear 336 until the rear face 384 of the bevel gear 336 abuts the abutment surface 335a. The central keyed slot 388 can extend from the rear face 384 to a front face 390 of the bevel gear 336 along the transverse direction T. The bevel gear 336 and the central keyed slot 388 can each have a length L9 that is substantially equivalent to the length L7 of the third unthreaded region 335 so that the posterior end 320 of the actuation rod 314 is at least substantially flush with the front face 390 of the bevel gear 336 when the rear face 384 of the gear 336 abuts the abutment surface 355a. Thus, once the rear face 384 of the bevel gear 336 abuts the abutment surface 355a, the technician can weld the bevel gear 336 to the actuation rod 314. For example, a weld can be formed at a joint between the posterior end 320 of the actuation rod 314 and the front face 390 of the bevel gear 336. It is to be appreciated, however, that other methods or techniques of affixing the bevel gear 336 to the actuation rod 314 are within the scope of the present disclosure.

Each actuation rod 314 is configured to extend through the first and second bores 440, 440' of the first and second wedge bodies 400, 400', respectively, and into the first and second curvilinear portions 134, 136 of the associated, vertically opposed cavities 116, 216 and 118, 218 of the superior and inferior plates 100, 200 when the implant 10 is in the collapsed configuration C.

The first threaded region 328 of the actuation rod 314 can have a thread pattern that is oriented in the opposite direction of a thread pattern formed on the second threaded region 330. Accordingly, the internal threads of the first and second bores 440, 440' can be in opposing orientations such that when the actuation rod 314 rotates, the first and second wedge members 306, 308 translate along the actuation rod 314 toward each other or away from each depending on the rotation direction of the actuation rod 314. The thread pattern on each threaded region 328, 330 can have a different thread pitch so that the first and second wedge members 306, 308 translate along the first and second threaded regions 328, 330 at different respective rates. For example, in the illustrated embodiments, the thread pitch of the first threaded region 328 may be greater than the thread pitch of the second threaded region 330 so that the first wedge member 306 translates a greater transverse distance along the first threaded region 328 than a distance by which the second wedge member 308 translates along the second threaded region 330 responsive to rotation of the actuation rod 314 about the central rod axis Y1. In this manner, the lordotic angle α of the implant 10 can be increased as the implant 10 expands from the collapsed configuration C to the expanded configuration E. The actuation rod 314 can define a pitch ratio of about 3:1 between the first and second threaded regions 328, 330. In other embodiments, the pitch ratio can range from about 1:1 to about 6:1.

It is to be appreciated, however, that the lordotic angle of the implant 10 can also be increased during expansion of the implant 10 by adjusting any one or a combination of additional factors, such as: the respective incline angles θS, θI, θS', θI' of the superior and inferior inclined surfaces 410, 412 of the first and second wedge bodies 400, 400'; the ramp angles βS1, βI1, βS2, βI2 of the anterior and posterior ramps 130, β2 within the vertically opposed cavities 116, 216 and 118, 218 of the superior and inferior plate bodies 102, 202; the relative heights H1, H2, H1', H2' of the outer and inner ends 402, 404 of the first and second wedge bodies 400, 400', by way of non-limiting example. Any of the foregoing factors, alone or in combination, can be adjusted or tailored as desired to provide a predetermined lordotic distraction profile when the implant 10 is in the expanded configuration E. It is also to be appreciated that the physician can achieve a kyphotic distraction profile by rotating the implant 10 by 180 degrees about the longitudinal implant axis X1 (i.e., flipping the implant 10 upside down) prior to insertion within the intervertebral space 5. Thus, the simple design of the implant 10 disclosed herein provides the benefit of allowing lordotic or kyphotic distraction of adjacent vertebral bodies 2, 4 as needed.

Figure 21:
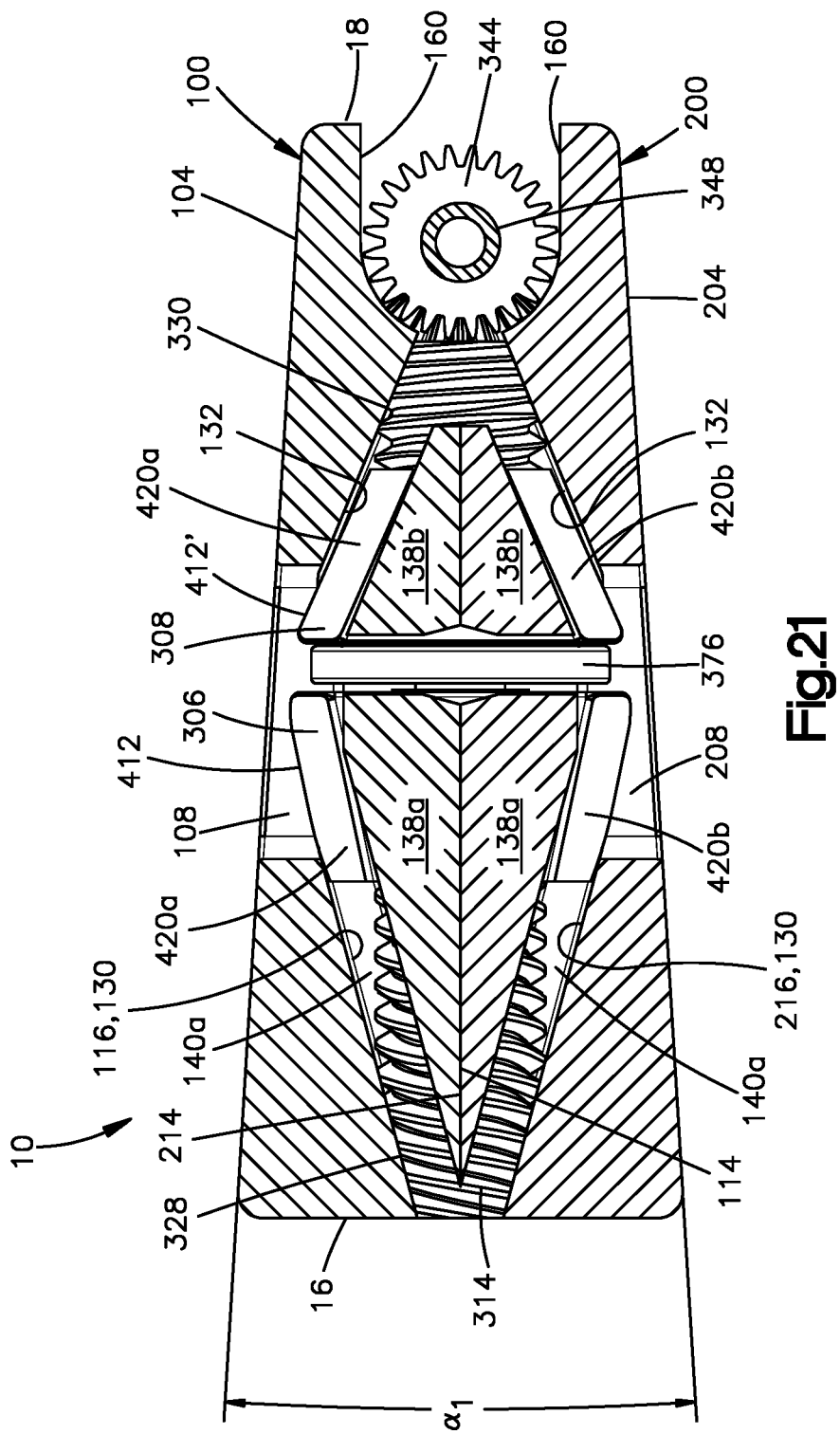
FIG. 21 is a sectional end view of the implant taken along section line 21-21 in FIG. 4, illustrating the implant in the collapsed configuration.
Figure 22:
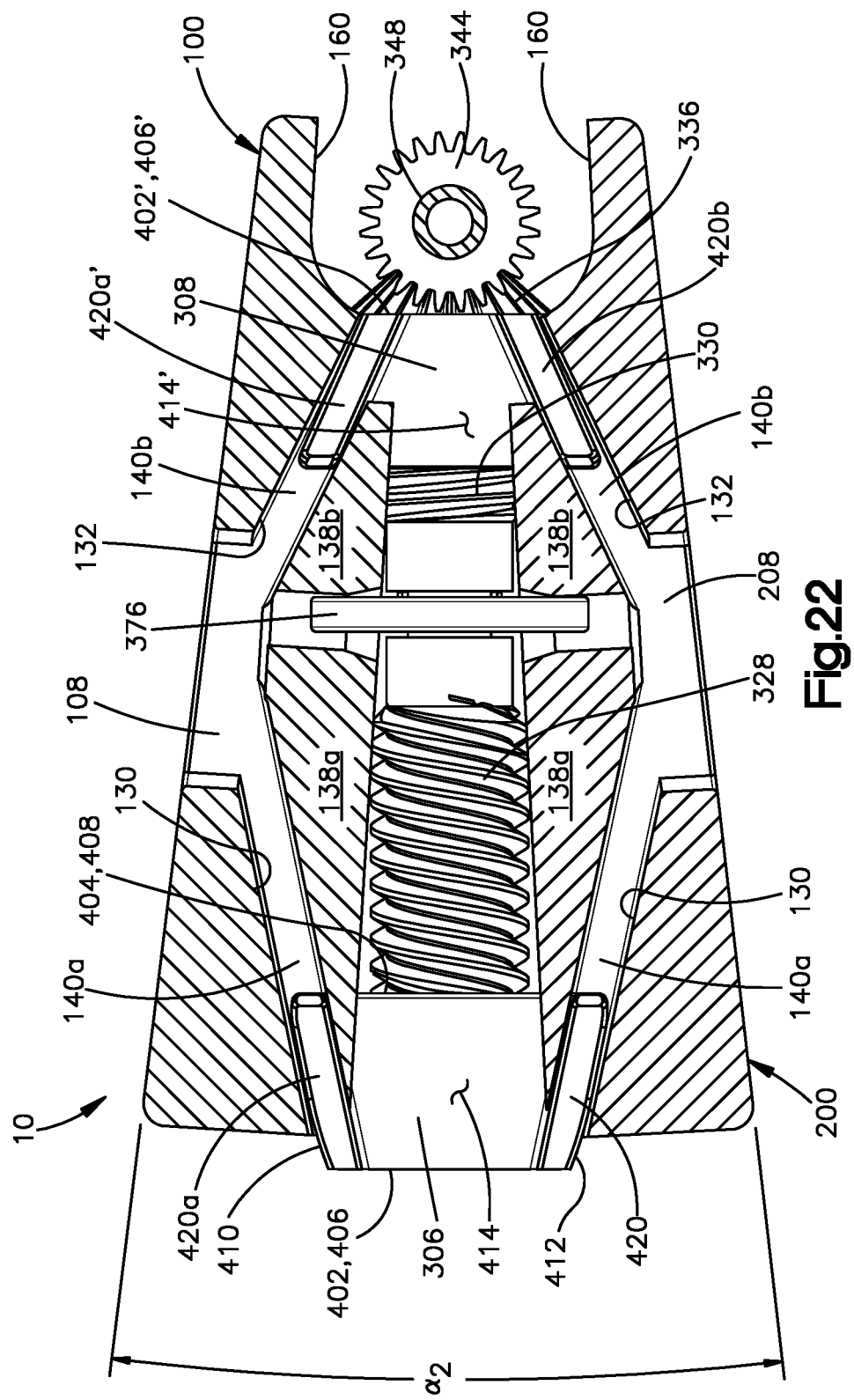
FIG. 22 is a sectional end view of the implant shown in the expanded configuration.

Referring to FIGS. 21 and 22, a sectional end view of the implant 10 is provide for both the collapsed configuration C (FIG. 21) and the expanded configuration E (FIG. 22), each view taken along the external side 124 of the first and third (i.e., proximal) cavities 116, 216 of the bone plates 100, 200 and facing the distal direction. While FIGS. 21 and 22 depict various aspects, features, and relative positions of each of the first and third cavities 116, 216, the first actuation member 310, the first pair 303 of wedge members, and the first bracket 364, it is to be appreciated that the following descriptions thereof can also be consistent with the second and fourth cavities 118, 218, the second actuation member 312, the second pair 304 of wedge members, and the second bracket 366.

Referring now to FIG. 21, in the collapsed configuration C, the interior plate contact surfaces 114, 214 of the superior and inferior plates 100, 200 can abut one another. The first and third cavities 116, 216 can provide space sufficient to house the first actuation member 310, the first pair 303 of wedge members, and at least a portion of the holding element 376 of the first bracket 364. The inner ends 404, 404' of the first and second wedge members 306, 308 face one another and are spaced apart from each other to define a gap therebetween. The holding element 376 of the first bracket 364 can be positioned between the inner ends 404, 404' of the first and second wedge members 306, 308 along the transverse direction T. At least one of the inner ends 404, 404' can be adjacent to, or can optionally abut, the holding element 376. While not visible in FIG. 21, the first threaded region 328 of the actuation rod 314 can be disposed within the first bore 440 of the first wedge member 306 and the second threaded region 330 of the rod 314 can be disposed within the second bore 440' of the second wedge member 308. The third landing surfaces 160 of the superior and inferior plate bodies 102, 202 can at least partially conform to an outer radius of the third gear 344.

Additionally, when the implant 10 is in the collapsed configuration C, the superior inclined surfaces 410, 410' of the wedge members 306, 308 can be adjacent to or abut the respective first and second ramp surface 130, β2 within the first cavity 116 while the inferior inclined surfaces 412, 412' of the wedge members 306, 308 can be adjacent to or abut the respective first and second ramp surface 130, β2 within the third cavity 216. The first ridges 420a, 420a' of the wedges can be disposed in the respective anterior and posterior channels 140a, 140b within the first cavity 116, and the second ridges 420b, 420b' can be disposed in the respective anterior and posterior channels 140a, 140b within the third cavity 216. While not visible in FIG. 21, it is to be appreciated that the third 420c, 420c' and fourth ridges 420d, 420d' of the wedge members 306, 308 can also be disposed within the channels 140a, 140b associated therewith. With continued reference to FIG. 21, portions of the first and second wedge members 306, 308 can extend into the first lumen 108 in communication with the first cavity 116 and into the third lumen 208 in communication with the third cavity 216, which enhances the compactness and reduces the overall transverse width W0 of the implant 10. The lumens 108, 208 have the additional benefit of promoting bone growth after the implant 10 is implanted in the intervertebral space 5.

During expansion of the implant 10 (i.e., between the respective configurations shown in FIGS. 21 and 22), the drive shaft 340 can be rotated about the central shaft axis X2, which rotates the third and fourth gears 344, 346, which, in turn, rotate the first and second gears 336, 338 and the actuation rods 314 about their central rod axes Y1. Rotation of the actuation rods 314 causes the first wedge member 306 of each pair 302, 304 to translate in the anterior direction (i.e., toward the anterior side 16 of the implant 10) along the first threaded region 328 and the second wedge member 308 of each pair 302, 304 to translate in the posterior direction (i.e., toward the posterior side 18 of the implant 10) along the second threaded region 330. The superior and inferior inclined surfaces 410, 412, 410', 412' of the first and second wedge members 306, 308 bear against the associated ramp surfaces 130, β2 of the plate bodies 102, 202 to separate the superior plate body 102 from the inferior plate body 202 along the vertical direction V. The ridges 420a, 420c, 420a', 420c' slide along the associated channels 140a, 140b. The holding element 376 of the bracket 364 can remain disposed within the annular recess 326 of the actuation rod 214 and can also remain within the exterior and interior slots 148, 150. As shown in FIG. 22, in the expanded configuration E, the outer end 404' of the second wedge member 308 can abut the rear face 384 of the first bevel gear 336, which affectively causes a braking action of the expansion mechanism 300. Additionally, in the expanded configuration E, the outer ends 404 of the first wedge members 306 of each pair 303, 304 can protrude marginally from the anterior side 16 of the implant 10. However, in other embodiments, the outer ends 404 of the first wedge members 306 can be spaced from the anterior side 16 of the implant 10 in the posterior direction when the implant 10 is in the expanded configuration E. It is to be appreciated that the actuation rod 314, the first and second bevel gears 336, 338, and the first and second wedge members 306, 308 can be collectively configured such that a stop surface or feature is not required for the first wedge member 306.

The embodiments set forth herein prove the implant 10 with numerous benefits. For example, the longitudinal length L0 of the implant 10 can be consistent regardless of whether the implant 10 is in the collapsed configuration C or the expanded configuration E. In embodiments wherein the first wedge members 306 do not protrude from the anterior side 16 of the implant 10 in the expanded configuration E, the width W0 of the implant 10 can also be consistent regardless of whether the implant 10 is in the collapsed or expanded configuration C, E.

It is to be appreciated that portions of any of the superior and inferior plate bodies 102, 202 and/or any component of the expansion mechanism 300 can include features configured to engage one or more tools for inserting, positioning, and/or expanding the implant 10. The superior and inferior plate bodies 102, 202 can each include one or more radiographic markers (not shown) aligned with one another along the vertical direction so that, with image analysis, the extent of plate separation can be determined or indicated by observing the relative vertical positions of the aligned radiographic markers.

It is also to be appreciated that the relative orientations of the actuation members 310, 312 and the drive shaft 340 in relation to each other and in relation to the superior and inferior plates 100, 200 can be altered. For example, the central rod axis Y1 of each actuation member 310, 312 could be oriented at an obtuse angle with respect to the central shaft axis X2 of the drive shaft 340. Additionally, in other embodiments, the implant can include only one actuation member 310 and one associated pair of wedge members 303.

It is yet also to be appreciated that the features of the implant 10 disclosed herein can be modified such that, for example, only one of the wedge members 306, 308 translates along the transverse direction in response to rotation of the drive shaft 340, or that only one of the superior and inferior plates 100, 200 moves along the vertical direction during expansion of the implant 10.

It is further to be appreciated that the dimensions set forth above in regards to various components of the implant 10 represent mere examples of the sizes of the foregoing components. The dimensions of the foregoing components can be adjusted as needed. Furthermore, the implant 10, and its various components, can also be scaled larger or smaller than the sizes disclosed herein.

Each of the components described herein can be formed of a biocompatible metal, such as titanium, steel, or any alloy thereof, such as a titanium-molybdenum alloy, for example, or any biocompatible polymeric material, such as polyether ether ketone (PEEK), or any other suitable biocompatible material.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An expandable implant, comprising:
    a first plate and a second plate spaced from each other along a first direction, the first plate defining a first bone-contacting surface configured to contact a superior vertebral body, the second plate defining a second bone-contacting surface opposed to the first bone contacting surface along the first direction, the second bone contacting surface configured to contact an inferior vertebral body;
    an actuation member at least partially disposed between the first and second plates with respect to the first direction, the actuation member defining a first axis, a first end and a second end spaced from the first end along a second direction along the first axis, wherein the second direction is perpendicular to the first direction;
    first and second wedge members carried by the actuation member and in engagement with the first and second plates;
    a first transmission member carried by the actuation member;
    a drive member defining a second axis, a proximal end and a distal end spaced from the proximal end along a third direction along the second axis, the third direction perpendicular to the first direction and offset from the second direction; and
    a second transmission member carried by the drive member,
    wherein the drive member is configured to communicate a driving force to the actuation member so as to cause the actuation member to rotate about the first axis, and at least one of first and second wedge members is configured to translate along the second direction in response to rotation of the actuation member about the first axis so as to move at least one of the first and second plates with respect to the other of the first and second plates along the first direction,
    wherein the first and second transmission members are configured to engage one another so as to transfer at least a portion of the driving force to the actuation member so as to rotate the actuation member about the first axis, and
    wherein the first transmission member is a first gear, and the second transmission member is a second gear.

2. The implant of claim 1, wherein first gear is configured to rotate about the first axis and the second gear is configured to rotate about the second axis.

3. The implant of claim 2, wherein the first and second gears are both bevel gears.

4. The implant of claim 2, wherein the first and second axes are perpendicular to one another.

5. The implant of claim 4, wherein the first and second axes are each perpendicular to the first direction.

6. An expandable implant, comprising:
    a first plate and a second plate spaced from each other along a first direction, the first plate defining a first bone-contacting surface configured to contact a superior vertebral body, the second plate defining a second bone-contacting surface opposed to the first bone contacting surface along the first direction, the second bone contacting surface configured to contact an inferior vertebral body,
    a first actuation member at least partially disposed between the first and second plates with respect to the first direction, the actuation member defining a first axis, a first end and a second end spaced from the first end along a second direction along the first axis, wherein the second direction is perpendicular to the first direction;
    first and second wedge members carried by the actuation member and in engagement with the first and second plates;
    a first transmission member carried by the actuation member;
    a drive member defining a second axis, a proximal end and a distal end spaced from the proximal end along a third direction along the second axis, the third direction perpendicular to the first direction and offset from the second direction; and
    a second transmission member carried by the drive member,
    wherein the drive member is configured to communicate a driving force to the actuation member so as to cause the actuation member to rotate about the first axis, and at least one of first and second wedge members is configured to translate along the second direction in response to rotation of the actuation member about the first axis so as to move at least one of the first and second plates with respect to the other of the first and second plates along the first direction,
    wherein the first and second transmission members are configured to engage one another so as to transfer at least a portion of the driving force to the actuation member so as to rotate the actuation member about the first axis, and
    wherein the implant further comprises a second actuation member that is spaced from the first actuation member along the third direction.

7. The implant of claim 6, wherein the second actuation member defines a third axis extending along the second direction, the second actuation member further defining a first end and a second end spaced from the first end along the second direction.

8. The implant of claim 7, further comprising third and fourth wedge members carried by the second actuation member, wherein the third and fourth wedge members are in engagement with the first and second plates, the third and fourth wedge members are configured to translate at least one of toward and away from each other along the third axis responsive to rotation of the second actuation member about the third axis so as to at least partially move the first and second plates away from one another in the first direction.

9. The implant of claim 8, further comprising:
a third transmission member carried by the second actuation member;
a fourth transmission member carried by the drive member, wherein the third and fourth transmission members are configured to engage one another so as to transfer at least a second portion of the driving force to the second actuation member so as to rotate the second actuation member about the third axis.

10. The implant of claim 9, wherein the first transmission member is a first gear, the second transmission member is a second gear, the third transmission member is a third gear, and the fourth transmission member is a fourth gear.

11. The implant of claim 10, wherein each of the first, second, third, and fourth gears is a bevel gear.

12. The implant of claim 11, wherein the first bevel gear is configured to rotate about the first axis, the third bevel gear configured to rotate about the third axis, and the second and fourth bevel gears are each configured to rotate about the second axis.

* * * * *